United States Patent
Jewett

(10) Patent No.: US 12,156,893 B2
(45) Date of Patent: Dec. 3, 2024

(54) ORAL COMPOSITION COMPRISING LACTIC ACID BACTERIA FOR REGULATING IMMUNE RESPONSES AND METHODS RELATED THERETO

(71) Applicant: The Regents of the University of California, Oakland, CA (US)

(72) Inventor: Anahid Jewett, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/130,118

(22) Filed: Apr. 3, 2023

(65) Prior Publication Data

US 2023/0372415 A1 Nov. 23, 2023

Related U.S. Application Data

(63) Continuation of application No. 16/470,040, filed as application No. PCT/US2017/066714 on Dec. 15, 2017, now Pat. No. 11,617,771.
(Continued)

(51) Int. Cl.
*A61K 35/744* (2015.01)
*A61K 31/198* (2006.01)
(Continued)

(52) U.S. Cl.
CPC .......... *A61K 35/744* (2013.01); *A61K 31/198* (2013.01); *A61K 31/337* (2013.01); *A61K 33/243* (2019.01); *A61K 35/17* (2013.01); *A61K 35/32* (2013.01); *A61K 35/745* (2013.01); *A61K 35/747* (2013.01); *A61K 45/06* (2013.01); *A61P 35/00* (2018.01); *C12N 5/0646* (2013.01); *C12N 5/0654* (2013.01); *C12N 5/0693* (2013.01); *A61K 2035/115* (2013.01); *C12N 2502/1164* (2013.01); *C12N 2502/1311* (2013.01)

(58) Field of Classification Search
CPC .................................................... A61K 35/744
See application file for complete search history.

(56) References Cited

U.S. PATENT DOCUMENTS

| 11,617,771 B2 | 4/2023 | Jewett |
| 2012/0135036 A1 | 5/2012 | Dennin et al. |

(Continued)

FOREIGN PATENT DOCUMENTS

| CN | 105663650 A | 6/2016 |
| JP | H10167972 A | 6/1998 |

(Continued)

OTHER PUBLICATIONS

English machine translation of Hu, CN 104207139 A, 2014.*
(Continued)

*Primary Examiner* — Rosanne Kosson
(74) *Attorney, Agent, or Firm* — Foley Hoag LLP; David P. Halstead

(57) ABSTRACT

The present application relates to probiotic compositions, e.g., comprising at least one bacterial strain selected from: *Streptococcus thermophilus*, *Bifidobacterium longum*, *Bifidobacterium breve*, *Bifidobacterium infantis*, *Lactobacillus acidophilus*, *Lactobacillus plantarum*, *Lactobacillus paracasei*, KE99, and *Lactobacillus bulgaricus*, optionally wherein the at least one bacterial strain is either alive or sonicated.

18 Claims, 39 Drawing Sheets

A

B

Related U.S. Application Data

(60) Provisional application No. 62/434,837, filed on Dec. 15, 2016.

(51) Int. Cl.

| | |
|---|---|
| *A61K 31/337* | (2006.01) |
| *A61K 33/243* | (2019.01) |
| *A61K 35/17* | (2015.01) |
| *A61K 35/32* | (2015.01) |
| *A61K 35/745* | (2015.01) |
| *A61K 35/747* | (2015.01) |
| *A61K 45/06* | (2006.01) |
| *A61P 35/00* | (2006.01) |
| *C12N 5/077* | (2010.01) |
| *C12N 5/0783* | (2010.01) |
| *C12N 5/09* | (2010.01) |
| *A61K 35/00* | (2006.01) |

(56) References Cited

U.S. PATENT DOCUMENTS

| | | |
|---|---|---|
| 2013/0295066 A1 | 11/2013 | Naidu et al. |
| 2019/0183942 A1 | 6/2019 | Gajewski et al. |
| 2020/0009201 A1 | 1/2020 | Jewett |
| 2023/0372415 A1 | 11/2023 | Jewett |

FOREIGN PATENT DOCUMENTS

| | | |
|---|---|---|
| JP | 2005/194259 A | 7/2005 |
| WO | WO-2012/133827 A1 | 10/2012 |
| WO | WO-2018/112366 A1 | 6/2018 |
| WO | WO-2018/180728 A1 | 10/2018 |
| WO | WO-2019/169179 A1 | 9/2019 |
| WO | WO-2021/022110 A1 | 2/2021 |
| WO | WO-2023/141119 A1 | 7/2023 |

OTHER PUBLICATIONS

Appleyard et al., "Pretreatment with the probiotic VSL#3 delays transition from inflammation to dysplasia in a rat model of colitis-associated cancer," Am J Physiol Gastrointest Liver Physiol, 301:G1004-G1013 (2011).

Bui et al. "Augmented IFN-γ and TNF-α induced by probiotic bacteria in NK cells mediate differentiation of stem-like tumors leading to inhibition of tumor growth and reduction in inflammatory cytokine release; regulation by IL-10." Frontiers in Immunology, 6:576 (2015).

Database WPI Week 199835 AN 1998-408599 Abstractof JP H10167972 A (1998).

Database WPI Week 200551 AN 2005-502133 Abstract of JP 2005/194529 A (2005).

Database WPI Week 201665 An 2016-40005K Abstract of CN 105663650 A (2016).

English translation of Iwabuchi et al. WO 2012/133827 A1, 2012.

English translation of Meiji Milk Products Co. Ltd., JP 2005-194259 A, 2005.

Extended European Search Report for EP Application No. 17881118.8 mailed Aug. 14, 2020.

Gui et al., "Well-balanced commensal microbiota contributes to anti-cancer response in a lung cancer mouse model," Genet Mol Res, 14(2):5642-5651 (2015).

International Search Report and Written Opinion for Application No. PCT/US2023/010989 dated May 8, 2023.

International Search Report and Written Opinion for International Application No. PCT/US2017/066714 dated Mar. 19, 2018.

Kaur et al., "Probiotics in Health and Disease: Distinct Roles of Different Strains in Natural Killer Cell Activation and Regulation," Crit Rev Immunol, 41(2): 1-19 (2021).

Kawaljit, et al. "Probiotic-treated super-charged NK cells efficiently clear poorly differentiated pancreatic tumors in Hu-BLT mice." Cancers, 12.1: 63 (2019).

Kozlowska et al., "Adoptive transfer of osteoclast-expanded natural killer cells for immunotherapy targeting cancer stem-like cells in humanized mice," Cancer Immunol Immunother, 65(7):835-845 (2016).

Kumar et al., "Colon cancer prevention through probiotics: an overview," J Cancer Sci Ther, 7(2):081-092 (2015).

Kwilasz, A. J., et al. "The therapeutic potential of interleukin-10 in neuroimmune diseases." Neuropharmacology,, 96: 55-69. (2015).

Li et al., "Lubricants in pharmaceutical solid dosage forms," Lubricants 2:21-43 (2014).

Tejada-Simon et al., "Ex vivo effects of lactobacilli, streptococci, and bifidobacteria ingestion on cytokine and nitric oxide production in a murine model," J Food Prot, 62(2): 162-169 (1999).

\* cited by examiner

Fig. 27 (cont')
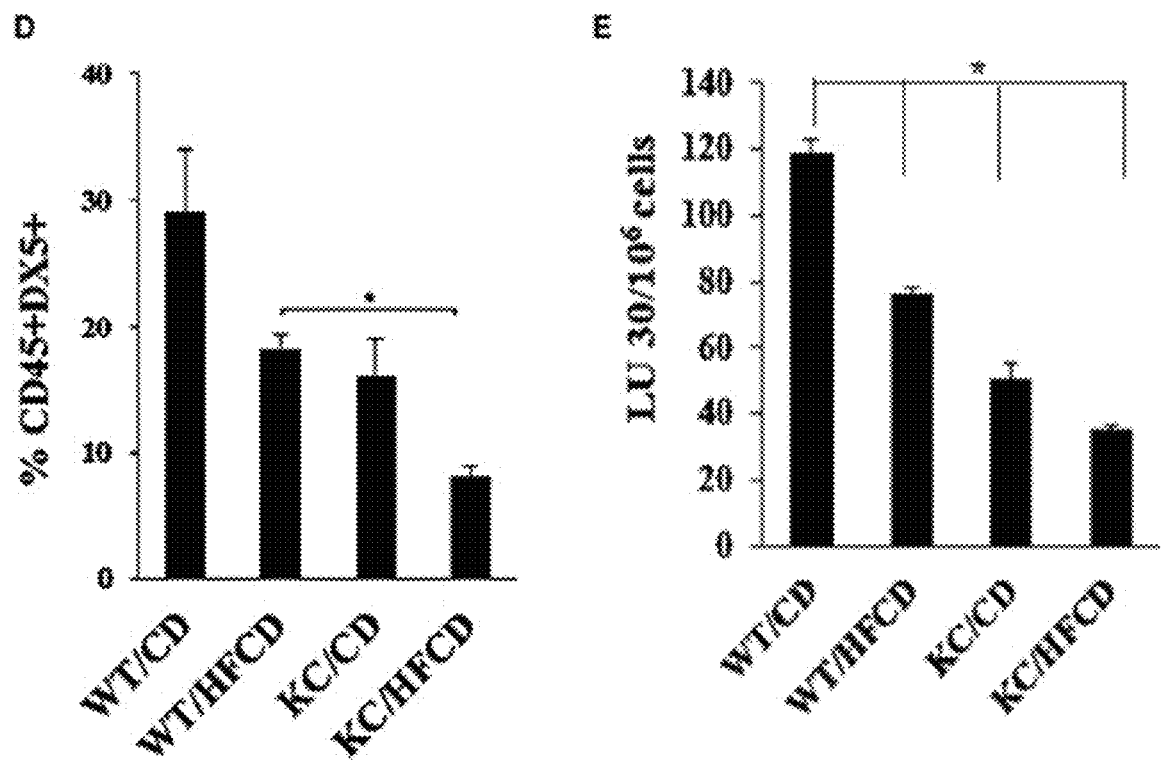

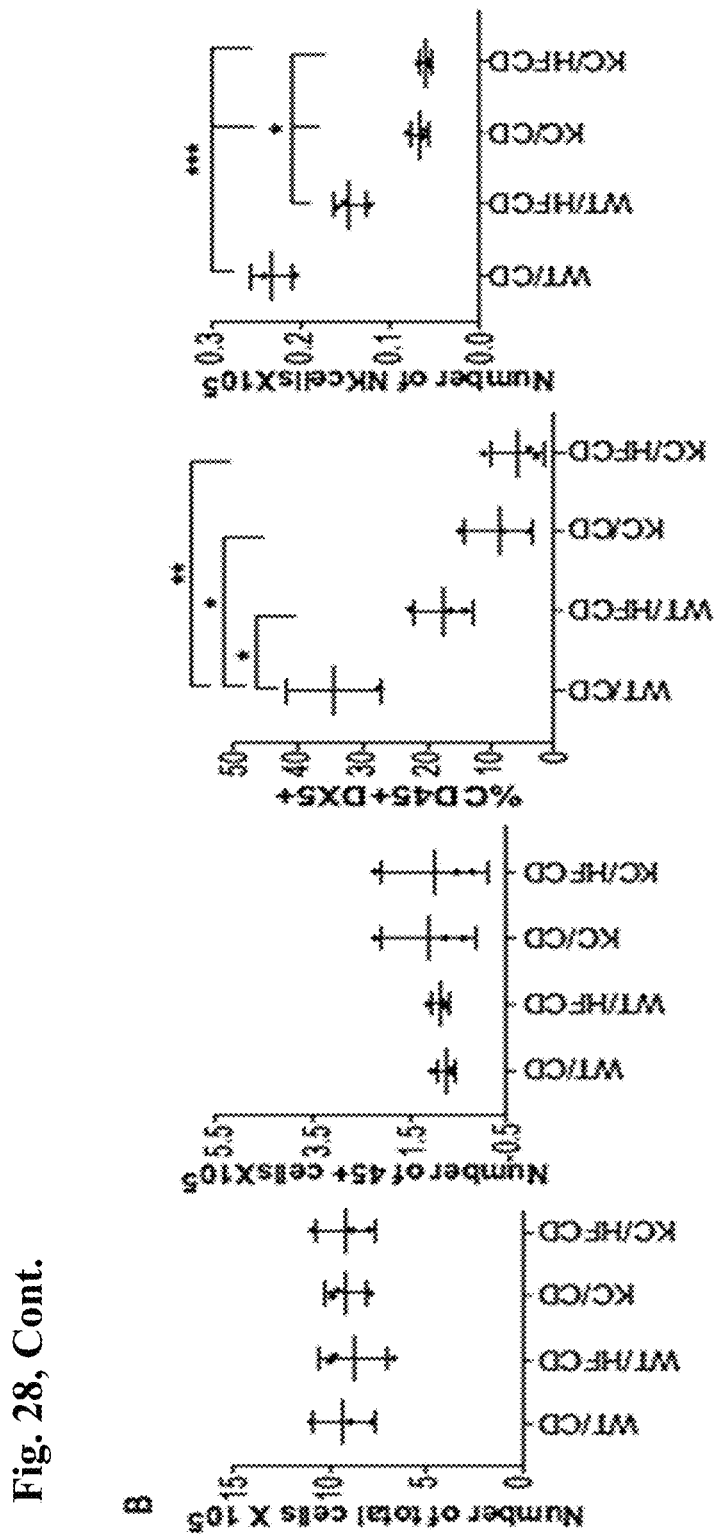
Fig. 28, Cont.

Fig. 28 (cont')
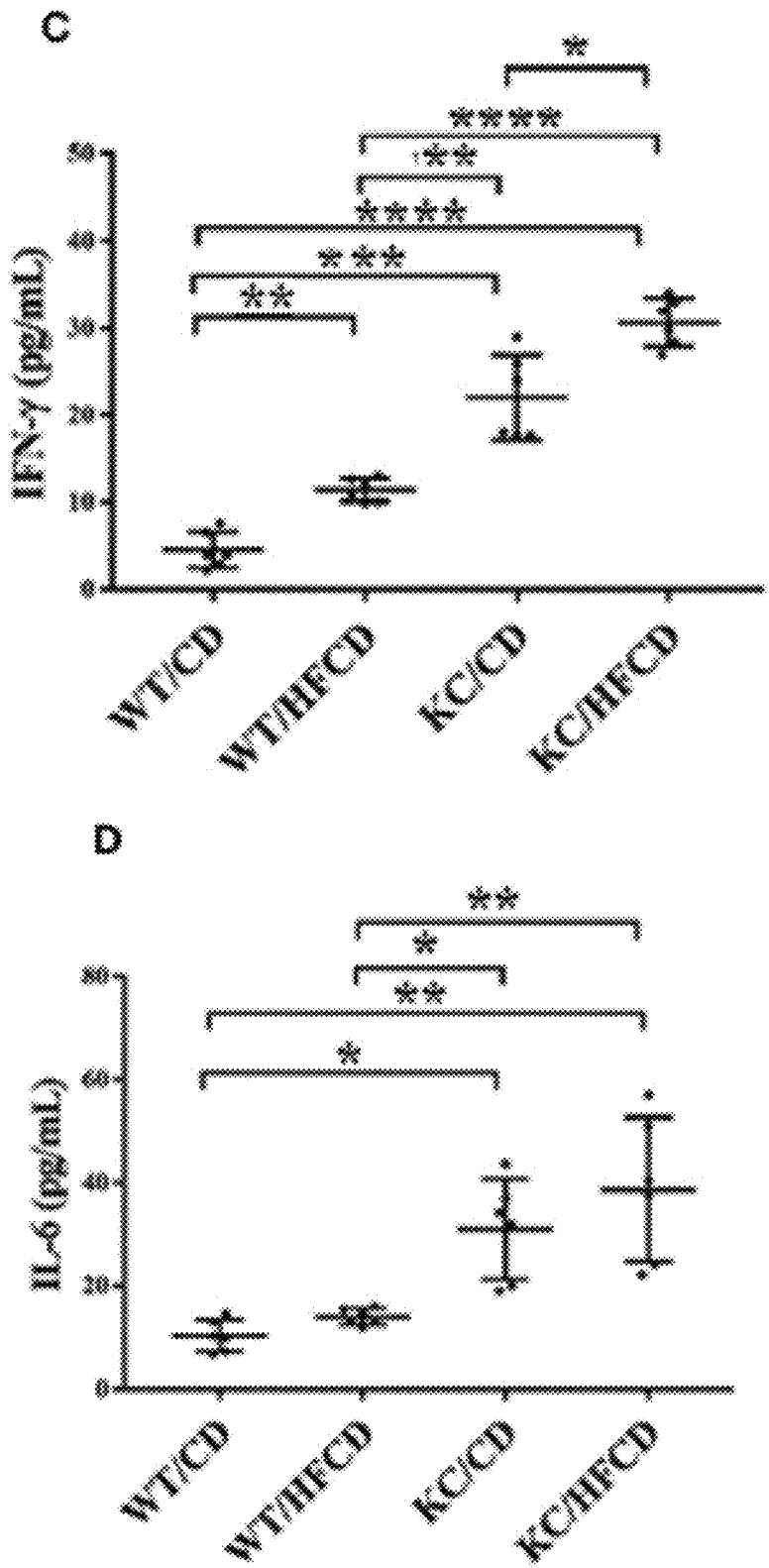

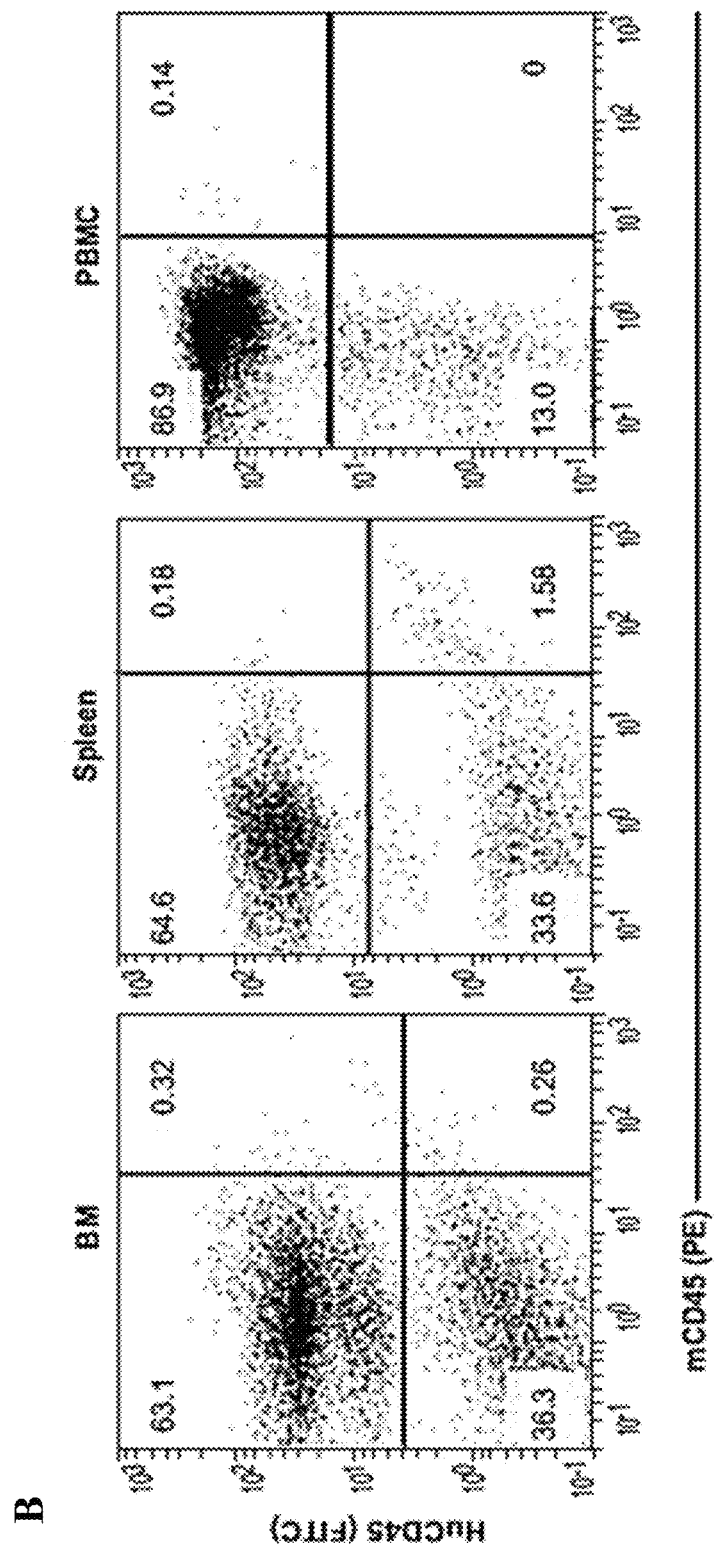
Fig. 29, Cont.

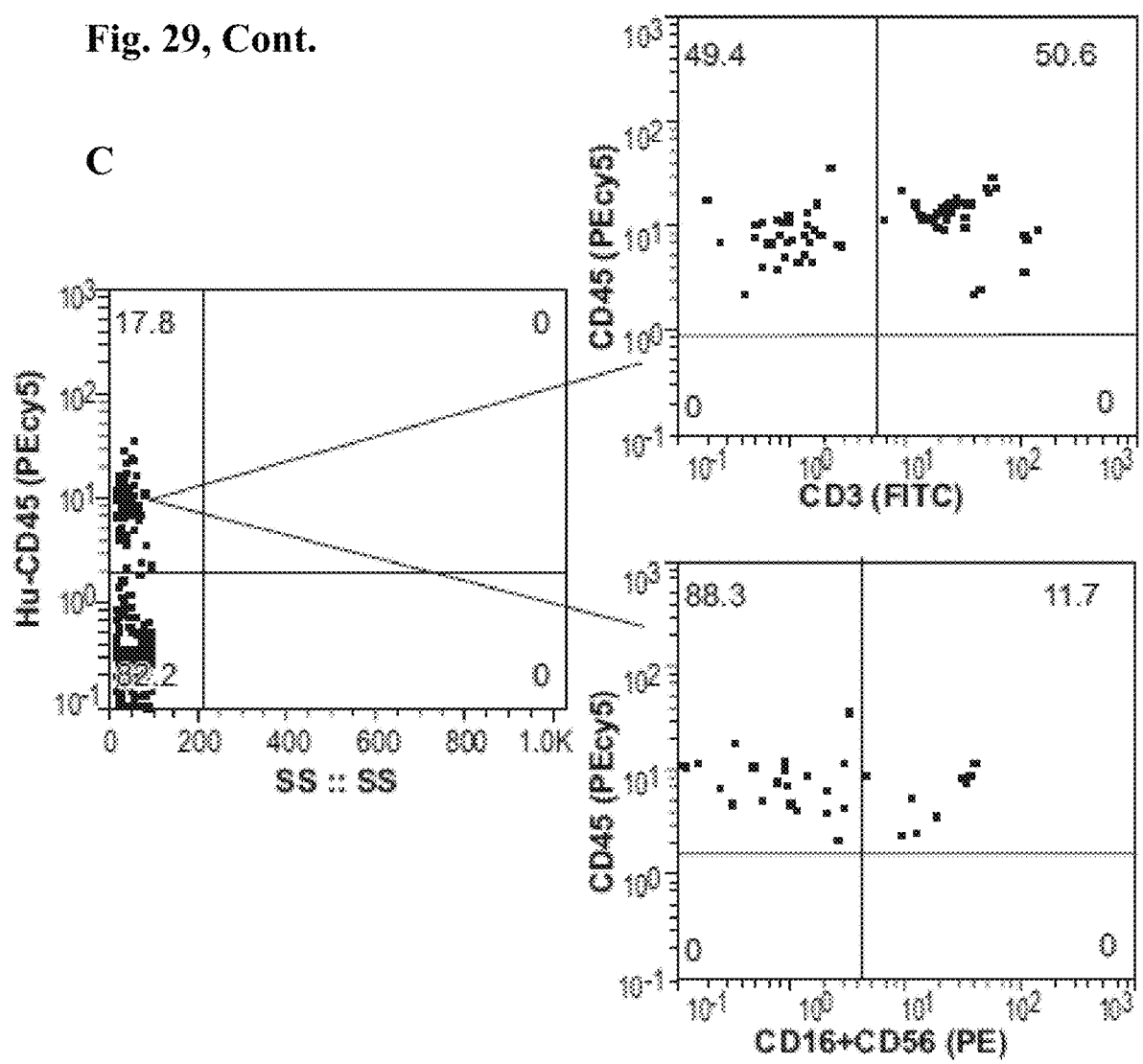
Fig. 29, Cont.
C

Fig. 29, Cont.
D
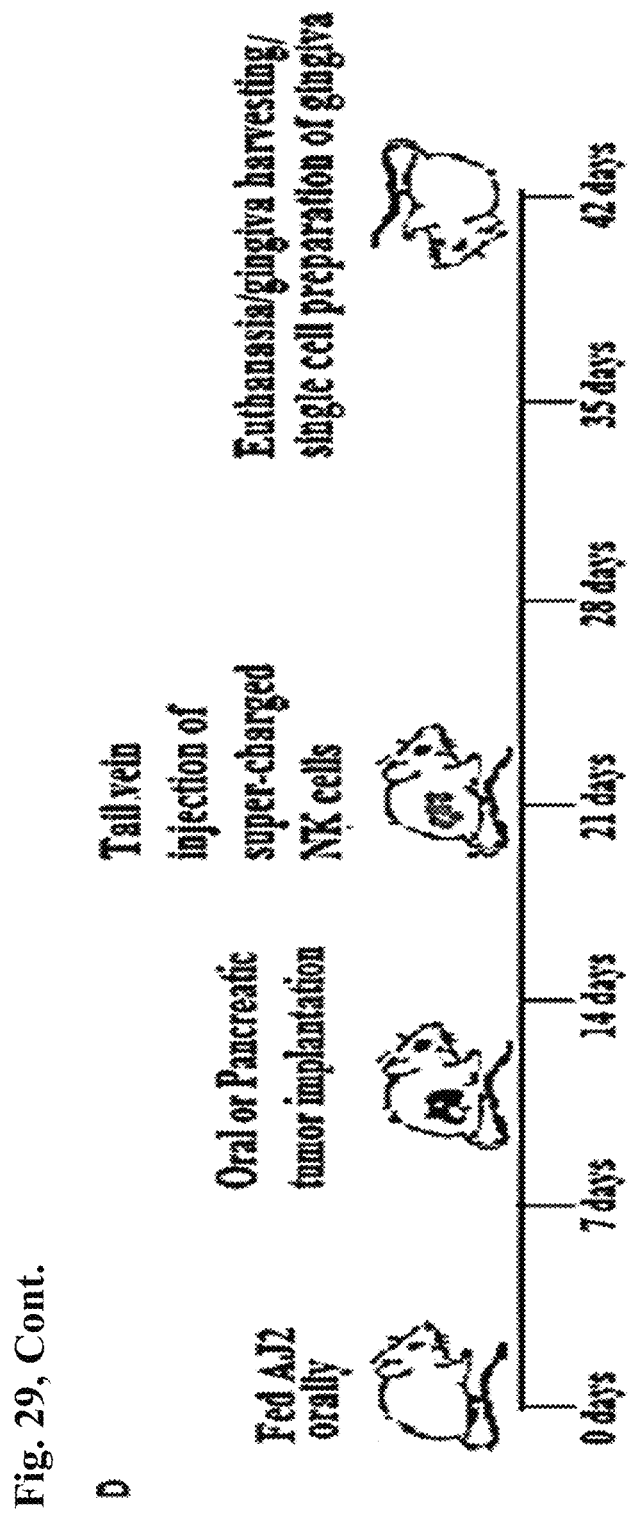

Fig. 29 (cont')
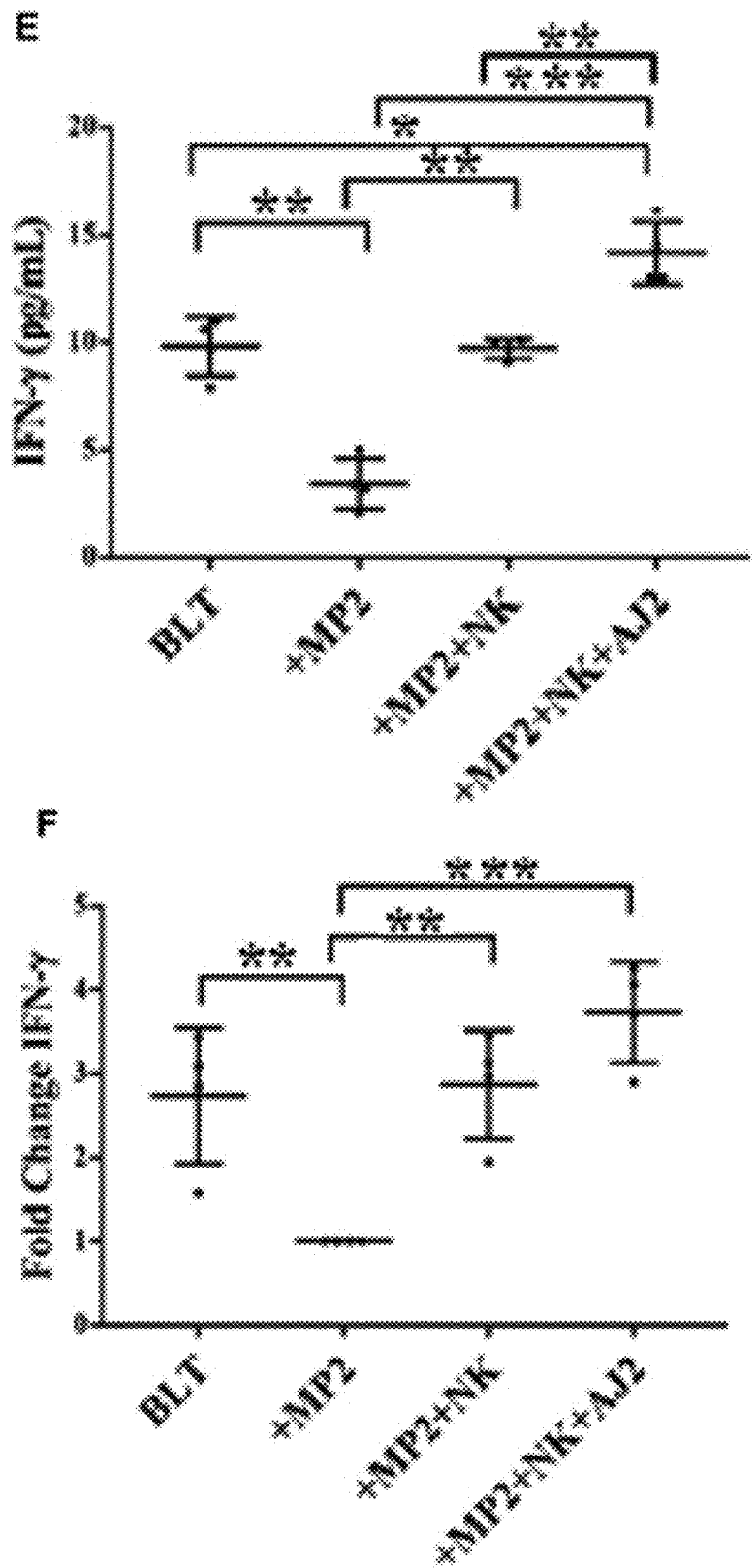

Fig. 29 (cont')
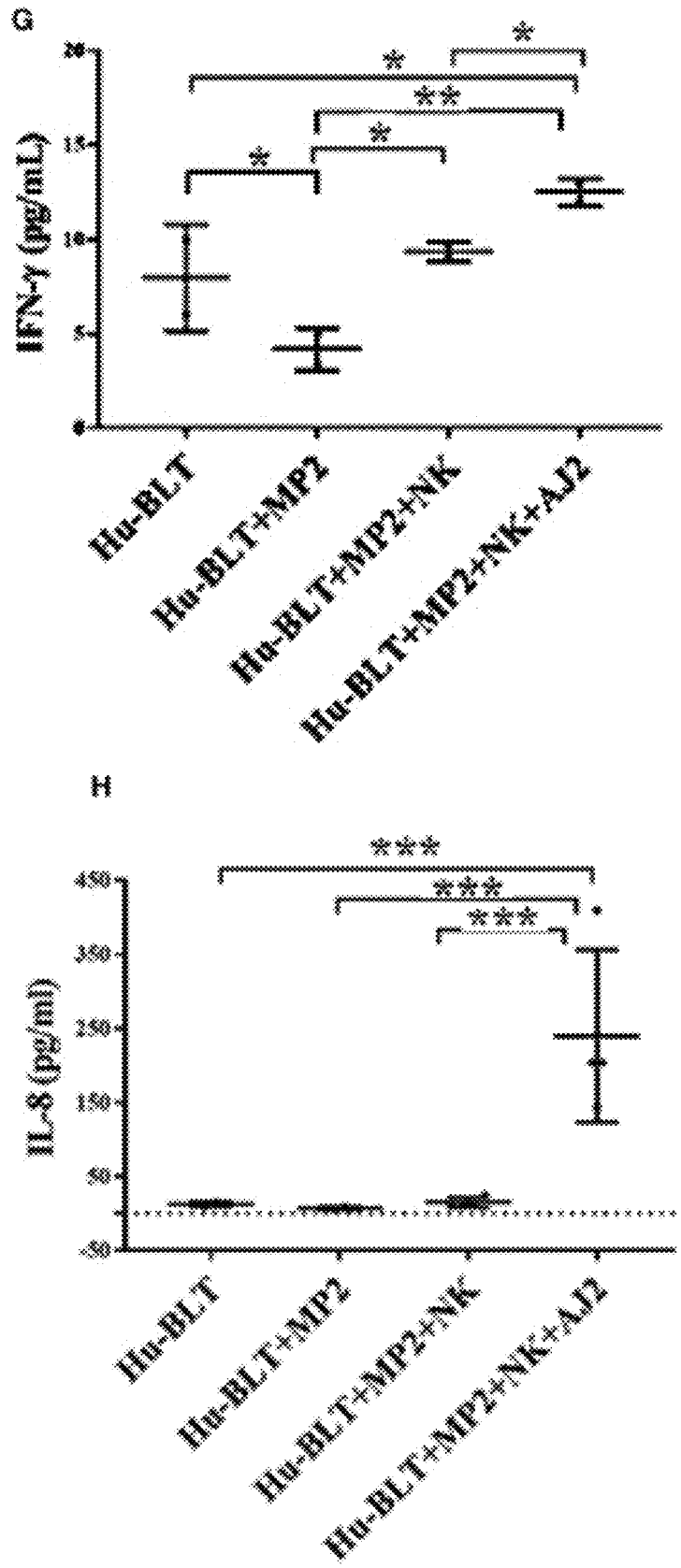

Fig. 29 (cont')
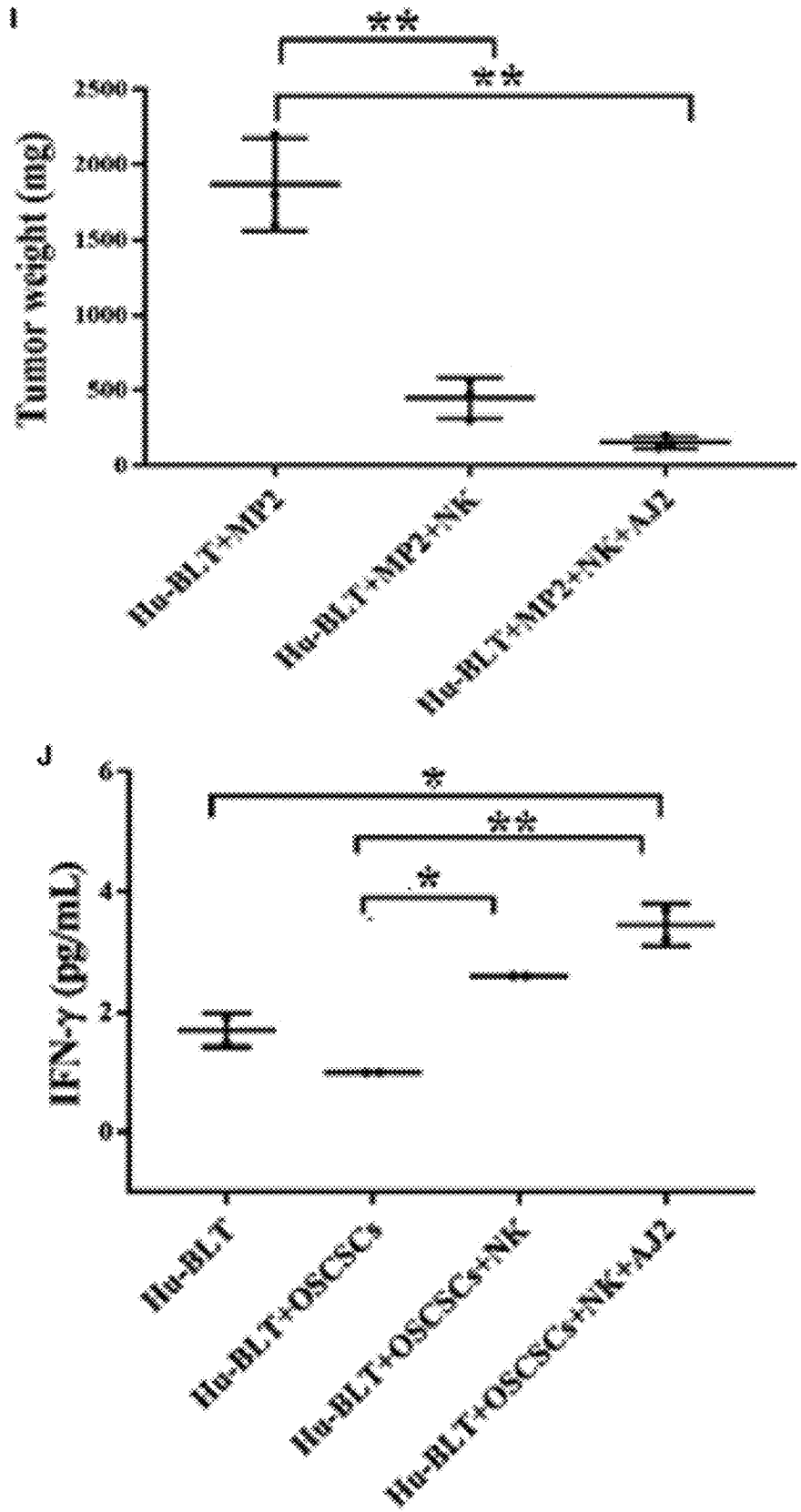

ORAL COMPOSITION COMPRISING LACTIC ACID BACTERIA FOR REGULATING IMMUNE RESPONSES AND METHODS RELATED THERETO

CROSS-REFERENCE TO RELATED APPLICATIONS

This application is a continuation of U.S. application Ser. No. 16/470,040, filed on Jun. 14, 2019, now U.S. Pat. No. 11,617,771, which is a U.S. national-stage filing under 35 U.S.C. § 371 of PCT Application No. PCT/US2017/066714, filed on Dec. 15, 2017, which claims the benefit of priority to U.S. Provisional Application No. 62/434,837, filed on Dec. 15, 2016. The entire contents of each of said applications are incorporated herein in their entirety by this reference.

BACKGROUND OF THE INVENTION

Natural killer (NK) cells are immune cells that develop in the bone marrow and constitute about 5-10% of lymphocytes in the peripheral blood and secondary lymphoid organs. NK cell effector functions include direct cytotoxicity, antibody-dependent cellular cytotoxicity (ADCC), and inflammatory cytokines and chemokines secretion. These secreted factors indirectly regulate other immune cells' functions. NK cells mediate cytotoxicity against both transformed cells and healthy cells by releasing perforin and granzyme B, pre-formed granules of proteins. These proteins can induce apoptosis of target cells. NK cells target and kill cancer stem cells (CSCs)/undifferentiated tumors, as well as healthy, non-transformed stem cells, which express low levels of major histocompatibility complex class I (MHC-I), CD54 and B7H1, and high levels of CD44.

Following selection (NK cell-mediated lysis) of stem-like tumors, NK cells differentiate CSCs, otherwise known as undifferentiated or poorly differentiated tumors, via secreted and membrane-bound IFN-γ and TNF-α. This leads to tumor growth prevention and tumor microenvironment remodeling. Activating receptors and co-receptors that recognize ligands expressed on tumors or virus-infected cells are responsible for mediating NK cell activation. Medium/high cytotoxic activity of lymphocytes in the peripheral blood is associated with a reduced cancer risk, and a high level of NK cell infiltration within the tumor is associated with better prognosis. On the other hand, low cytotoxic activity is associated with increased cancer risk. The number of NK cells, along with their cytotoxic and cytokine secreting functions, is significantly diminished in cancer patients.

The split anergy in NK cells indicates reduced NK cell cytotoxicity in the presence of significant secretion of cytokines (Tseng et al. (2014) Front Immunol, 5: 269; Magister et al (2012) Eur J Cell Biol, 91(5):391-401; Tseng et al. (2015) Oncotarget 6(11):8947-59). Induction of split anergy in NK cells promotes differentiation of target cells via secreted and membrane-bound factors, increases key differentiation receptors on tumor cells, induces tumor cell resistance to NK cell-mediated cytotoxicity, and inhibits inflammation due to a decrease or shutdown of cytokine and chemokine production after tumor differentiation.

The underlying mechanism of NK cell immunomodulation is not understood. A great need exists to identify therapeutic compositions and methods for improved NK immunotherapy.

SUMMARY OF THE INVENTION

The present invention is based, at least in part, on the discovery that specific combinations of probiotic bacteria induce significant split anergy in activated NK cells, leading to a significant induction of IFN-γ and TNF-α. In addition, such compositions of probiotic bacteria induce significant expansion of NK cells. The compositions of probiotic bacteria described herein can be used to inhibit or prevent inflammation, and/or to highly activate NK cells when they are needed (e.g., under inflammation, infections, or malignancies scenarios). To compare different combinations, a novel activation index for the NK cells which evaluated ratios of several important cytokines and chemokines that can attenuate auto-immunity while enhancing significant activation of NK cells under pathologic conditions was used. In this way, strains were selected to: 1) provide regulated activation of NK cells when no activation of NK cells is desired; 2) promote heightened activation of NK cells when activated by cytokines and/or cross-linking of receptors, as occurs during functional activation of NK cells in cancer; and/or 3) foster diversity in gut microflora. In these various compositions and methods, bacteria regulate the gut mucosal immunity in such a way that NK activation is increased only when needed during infections or malignancies. When there is no need for activated NK cells, bacteria can regulate NK function to suppress inflammation. Such coordinated regulation of NK cell function can mediate NK activity to reduce unwanted inflammation while fostering immunity during disease.

Figure 30:
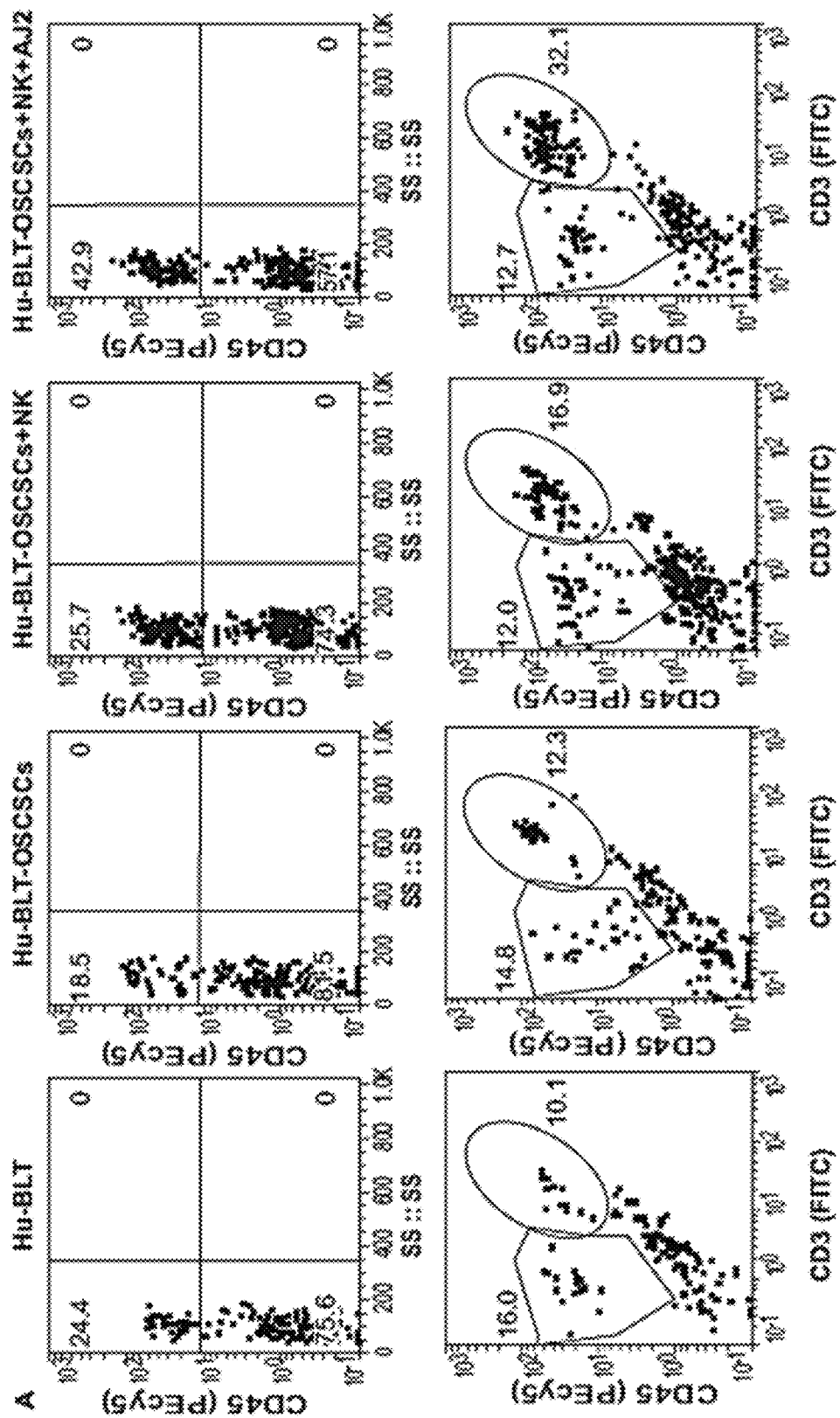

FIG. 30 shows percentages of CD45+ and CD3+ T cells in gingiva of tumor-bearing mice injected with the NK cells and fed with AJ2. Gingiva from oral tumor-bearing mice injected with NK cells and fed with and without AJ2 were harvested and single-cell suspensions were prepared as described in the Examples. Percentages of CD45+ and CD3+ T cells in gingiva in four groups of mice were determined using flow cytometric analysis after staining with the respective PEcy5-conjugated and FITC-conjugated antibodies. Isotype control antibodies were used as controls.

DETAILED DESCRIPTION OF THE INVENTION

Based on immunologic, pharmacologic, and molecular analyses, specific combinations of probiotic bacteria induce significant split anergy in activated NK cells, leading to a significant induction of IFN-γ and TNF-α. In addition, such compositions of probiotic bacteria induce significant expansion of NK cells.

For example, probiotic bacterial compositions described herein may be administered alone, or in combination with other NK immunotherapy. Without wishing to be limited by theory, it is that NK immunotherapy increases cytokine production in immune tissue of subjects, while probiotic supplementation further enhances these effects, resulting in more differentiated tumors in vivo.

Accordingly, the present invention relates, in part, to compositions of probiotic bacteria and methods for treating inflammation or other immune diseases or disorders (including cancers (e.g., oral cancer, colon cancer, pancreatic cancer, or other cancers in the Gastrointestinal (GI) tract) with a composition comprising at least one probiotic bacterial strain, alone or in combination with other NK immunotherapies. In another aspect, the present invention provides diagnostic, prognostic, and prophylactic methods of stratifying patients and predicting responses of the target disease (e.g., inflammatory and/or immune diseases, cancers, etc.) to treatment with a composition comprising at least one probiotic bacterial strain, alone or in combination with other NK immunotherapies based upon a determination and analysis of biomarkers (e.g., cytokines and/or chemokines such as those listed in Table 1) described herein.

I. Definitions

The articles "a" and "an" are used herein to refer to one or to more than one (i.e. to at least one) of the grammatical object of the article. By way of example, "an element" means one element or more than one element.

The term "administering" is intended to include routes of administration which allow an agent to perform its intended function. Examples of routes of administration for treatment of a body which can be used include injection (subcutaneous, intravenous, parenterally, intraperitoneally, intrathecal, etc.), oral, inhalation, and transdermal routes. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. The agent also may be administered as a prodrug, which is converted to its active form in vivo.

The term "altered amount" or "altered level" refers to increased or decreased copy number (e.g., germline and/or somatic) of a biomarker (e.g., cytokines and/or chemokines such as those listed in Table 1) nucleic acid, e.g., increased or decreased expression level in a cancer sample, as compared to the expression level or copy number of the biomarker nucleic acid in a control sample. The term "altered amount" of a biomarker also includes an increased or decreased protein level of a biomarker protein in a sample, e.g., a cancer sample, as compared to the corresponding protein level in a normal, control sample. Furthermore, an altered amount of a biomarker protein may be determined by detecting posttranslational modification such as methylation status of the marker, which may affect the expression or activity of the biomarker protein.

The amount of a biomarker (e.g., cytokines and/or chemokines such as those listed in Table 1) in a subject is "significantly" higher or lower than the normal amount of the biomarker, if the amount of the biomarker is greater or less, respectively, than the normal level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternately, the amount of the biomarker in the subject can be considered "significantly" higher or lower than the normal amount if the amount is at least about two, and preferably at least about three, four, or five times, higher or lower, respectively, than the normal amount of the biomarker. Such "significance" can also be applied to any other measured parameter described herein, such as for expression, inhibition, cytotoxicity, cell growth, and the like.

The term "altered level of expression" of a biomarker (e.g., cytokines and/or chemokines such as those listed in Table 1) refers to an expression level or copy number of the biomarker in a test sample, e.g., a sample derived from a patient suffering from a disease or disorder (e.g., inflammation and/or other immune diseases or disorders, including cancers), that is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples. The altered level of expression is greater or less than the standard error of the assay employed to assess expression or copy number, and is preferably at least 20%, 30%, 40%, 50%, 60%, 70%, 80%, 90%, 100%, 150%, 200%, 300%, 350%, 400%, 500%, 600%, 700%, 800%, 900%, 1000% or more times the expression level or copy number of the biomarker in a control sample (e.g., sample from a healthy subjects not having the associated disease) and preferably, the average expression level or copy number of the biomarker in several control samples. In some embodiments, the level of the biomarker refers to the level of the biomarker itself, the level of a modified biomarker (e.g., phosphorylated biomarker), or to the level of a biomarker relative to another measured variable, such as a control (e.g., phosphorylated biomarker relative to an unphosphorylated biomarker).

The term "altered activity" of a biomarker (e.g., cytokines and/or chemokines such as those listed in Table 1) refers to an activity of the biomarker which is increased or decreased in a disease state, e.g., in a cancer sample, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker (e.g., cytokines and/or chemokines such as those listed in Table 1) refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a biomarker polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Antibodies may be polyclonal or monoclonal; xenogeneic, allogeneic, or syngeneic; or modified forms thereof (e.g. humanized, chimeric, etc.). Antibodies may also be fully human. Preferably, antibodies of the present invention bind specifically or substantially specifically to a biomarker polypeptide or fragment thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The term "assigned score" refers to the numerical value designated for each of the biomarkers after being measured in a patient sample. The assigned score correlates to the absence, presence or inferred amount of the biomarker in the sample. The assigned score can be generated manually (e.g., by visual inspection) or with the aid of instrumentation for image acquisition and analysis. In certain embodiments, the assigned score is determined by a qualitative assessment, for example, detection of a fluorescent readout on a graded scale, or quantitative assessment. In certain embodiments, an "aggregate score," which refers to the combination of assigned scores from a plurality of measured biomarkers, is determined. For example, the aggregate score may be a summation of assigned scores. Alternatively, combination of assigned scores may involve performing mathematical operations on the assigned scores before combining them into an aggregate score. In certain embodiments, the aggregate score is also referred to herein as the "predictive score."

The term "biomarker" refers to a measurable entity of the present invention that has been determined to be predictive of the effects of the probiotic bacteria therapy described herein, either alone or in combination with at least one other NK cell-related immunotherapies, on a target disease or disorder (e.g., one of inflammatory and/or immune diseases or disorders, such as cancers). Biomarkers can include, without limitation, nucleic acids and proteins, including those shown in the Tables (e.g., Table 1), the Examples, the Figures, and otherwise described herein. As described herein, any relevant characteristic of a biomarker can be used, such as the copy number, amount, activity, location, modification (e.g., phosphorylation), and the like.

The term "body fluid" refers to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features. Unless otherwise stated, the terms include metaplasias. In some embodiments, such characteristics include at least one of silencing, decreasing, and/or avoiding host immune response, and/or being resistant to host cell (e.g., NK cells) lysis and/or differentiations. In some embodiments, such cancer-causing cells are cancer stem cells (e.g, oral squamous carcinoma stem cells (OSCSCs)). In some embodiments, such cells exhibit such characteristics in part or in full due to at least one genetic mutations. Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is oral cancer, breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

In some embodiments, the cancer is "triple negative breast cancer" or "TNBC," which refers to breast cancers that are estrogen receptor (ER) negative, progesterone receptor (PR) negative, and human epidermal growth factor receptor 2 (HER-2) negative (Pegram et al. (1998) *J. Clin. Oncol.* 16:2659-2671; Wiggans et al. (1979) *Cancer Chemother. Pharmacol.* 3:45-48; Carey et al. (2007) *Clin. Cancer Res.* 13:2329-2334).

In certain embodiments, the cancer is a "PI3Kbeta-dependent cancer," which can refer to a cancer that is functionally dependent on PI3Kbeta. For instance, even if the expression level of PI3Kbeta (e.g., PI3Kbeta mRNA, PI3Kbeta protein, newly synthesized PI3Kbeta protein, etc.) in a tumor tissue is comparable to its expression level in normal tissue, a cancer is PI3Kbeta-dependent if inhibition of the PI3Kbeta mRNA and/or protein, directly or indirectly such as by using RNAi or any other means, or deletion of the PI3Kbeta gene (e.g., by knock-out or clustered regularly interspaced short palindromic repeats (CRISPR) technology) leads to inhibition of oncogenesis, tumor cell proliferation, tumor metastasis or induces tumor cell differentiation. The term "PI3Kbeta-dependent cancer" also refers to a cancer in which PI3Kbeta is expressed (e.g., PI3Kbeta mRNA, PI3Kbeta protein, newly synthesized PI3Kbeta protein, etc.) at a significantly higher level than the normal amount of PI3Kbeta expressed in a non-cancerous cell of the same cell type as the PI3Kbeta-dependent cancer.

The term "micrometastasis" as used herein is preferably defined as a group of confluent cancer cells measuring from greater than 0.2 mm and/or having greater than 200 cells to 2 mm in maximum width. More preferably "micrometastasis" is defined as a group of confluent cancer cells from 0.2 mm to 2 mm in maximum width (see Edge et al. (2010) *ADCC Cancer Staging Manual and Handbook* (7th ed.)). An alternative preferred definition of "micrometastasis" is a confluent group of at least 1000 cancer cells and at least 0.1 mm in widest dimension up to 1 mm in widest dimension. Micrometastasis is generally not visible in standard contrast MRI imaging or other clinical imaging techniques. However, in certain cancers, radioactive antibodies directed to tumor selective antigens (e.g., Her2 for breast cancer metastasis) allows for visualization of micrometastasis. Other indirect detection methods include contrast media leakage at brain micrometastasis sites due to VEGF induced vascular leakage (Yano et al. (2000) *Cancer Res.* 60:4959-49067; U.S. Pat. Publ. 2015/0352113). More sensitive imaging techniques may also be applied to detect micrometastases. For example, blood volume may be imaged by MRI using the alternative contrast agent, USPIO (Molday Iron, Biopal, Worcester, Mass.) to detect micrometastasis (Yin et al. (2009) *Clin. Exp. Metastasis.* 26:403-414).

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In certain embodiments, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In other preferred embodiments, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention. In certain embodiments, the control may comprise normal or non-cancerous cell/tissue sample. In other preferred embodiments, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In other preferred embodiments, the control may comprise normal cells, cells from patients treated with combination chemotherapy, and cells from patients having benign cancer. In other embodiments, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In other preferred embodiments, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In other embodiments, the control may comprise expression product levels grouped as percentiles within or based on a set of patient samples, such as all patients with cancer. In certain embodiments, a control expression product level is established wherein higher or lower levels of expression product relative to, for instance, a particular percentile, are used as the basis for predicting outcome. In other preferred embodiments, a control expression product level is established using expression product levels from cancer control patients with a known outcome, and the expression product levels from the test sample are compared to the control expression product level as the basis for predicting outcome. As demonstrated by the data below, the methods of the present invention are not limited to use of a specific cut-point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of a biomarker nucleic acid or "normal" level of expression of a biomarker nucleic acid or protein is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human, not afflicted with cancer, or from a corresponding non-cancerous tissue in the same subject who has cancer.

As used herein, the term "costimulate" with reference to activated immune cells includes the ability of a costimulatory molecule to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells."

The term "determining a suitable treatment regimen for the subject" is taken to mean the determination of a treatment regimen (i.e., a single therapy or a combination of different therapies that are used for the prevention and/or treatment of the cancer in the subject) for a subject that is started, modified and/or ended based or essentially based or at least partially based on the results of the analysis according to the present invention. One example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

The term "diagnosing cancer" includes the use of the methods, systems, and code of the present invention to determine the presence or absence of a cancer or subtype thereof in an individual. The term also includes methods, systems, and code for assessing the level of disease activity in an individual.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

The term "expression signature" or "signature" refers to a group of one or more coordinately expressed biomarkers related to a measured phenotype. For example, the genes, proteins, metabolites, and the like making up this signature may be expressed in a specific cell lineage, stage of differentiation, or during a particular biological response. The biomarkers can reflect biological aspects of the tumors in which they are expressed, such as the cell of origin of the cancer, the nature of the non-malignant cells in the biopsy, and the oncogenic mechanisms responsible for the cancer. Expression data and gene expression levels can be stored on computer readable media, e.g., the computer readable medium used in conjunction with a microarray or chip reading device. Such expression data can be manipulated to generate expression signatures.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

The term "immune checkpoint" refers to a group of molecules on the cell surface of CD4+ and/or CD8+ T cells that fine-tune immune responses by down-modulating or inhibiting an anti-tumor immune response. Immune checkpoint proteins are well-known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, and A2aR (see, for example, WO 2012/177624). The term further encompasses biologically active protein fragment, as well as nucleic acids encoding full-length immune checkpoint proteins and biologically active protein fragments thereof. In some embodiments, the term further encompasses any fragment according to homology descriptions provided herein.

The term "cytokine" refers to a broad and loose category of small proteins (~5-20 kDa) that are important in cell signaling. Their release has an effect on the behaviour of cells around them. cytokines are involved in autocrine signalling, paracrine signalling and endocrine signalling as immunomodulating agents. Cytokines include chemokines, interferons, interleukins, lymphokines, and tumour necrosis factors, and may additionally include hormones or growth factors in the instant disclosure. Cytokines are produced by a broad range of cells, including immune cells like macrophages, B lymphocytes, T lymphocytes and mast cells, as well as endothelial cells, fibroblasts, and various stromal cells. Preferred cytokines are exemplified in the specification and the Figures of the instant disclosure, for example, in Table 1.

The term "cytokine/chemokine activity," includes the ability of a cytokine or a chemokine to modulate at least on of cellular functions. Generally, cytokines or chemokines modulate the balance between humoral and cell-based immune responses, and they regulate the maturation, growth, and responsiveness of particular cell populations. Thus, the term "cytokine/chemokine activity" includes the ability of a cytokine or chemokine to bind its natural cellular receptor(s), the ability to modulate cellular signals, and the ability to modulate the immune response.

The term "immune response" includes T cell mediated and/or B cell mediated immune responses. Exemplary immune responses include T cell responses, e.g., cytokine production and cellular cytotoxicity. In addition, the term immune response includes immune responses that are indirectly affected by T cell activation, e.g., antibody production (humoral responses) and activation of cytokine responsive cells, e.g., macrophages.

The term "immunotherapeutic agent" can include any molecule, peptide, antibody or other agent which can stimulate a host immune system to generate an immune response to a tumor or cancer in the subject. Various immunotherapeutic agents are useful in the compositions and methods described herein.

The term "inhibit" includes the decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented. Similarly, a biological function, such as the function of a protein, is inhibited if it is decreased as compared to a reference state, such as a control like a wild-type state. For example, kinase activity of a mutant PI3 kinase or a PI3 kinase that is contacted with a PI3 kinase inhibitor is inhibited if the kinase activity is decreased due to the mutation and/or contact with the inhibitor, in comparison to the wild-type PI3 kinase and/or the PI3 kinase not contacted with the inhibitor. Such inhibition can be induced, such as by application of agent at a particular time and/or place, or can be constitutive, such as by a heritable mutation. Such inhibition can also be partial or complete (e.g., essentially no measurable activity in comparison to a reference state, such as a control like a wild-type state). Essentially complete inhibition is referred to as blocked.

The term "interaction", when referring to an interaction between two molecules, refers to the physical contact (e.g., binding) of the molecules with one another. Generally, such an interaction results in an activity (which produces a biological effect) of one or both of said molecules.

A "kit" is any manufacture (e.g. a package or container) comprising at least one reagent, e.g. a probe or small molecule, for specifically detecting and/or affecting the expression of a marker of the present invention. The kit may be promoted, distributed, or sold as a unit for performing the methods of the present invention. The kit may comprise one or more reagents necessary to express a composition useful in the methods of the present invention. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The term "neoadjuvant therapy" refers to a treatment given before the primary treatment. Examples of neoadjuvant therapy can include chemotherapy, radiation therapy, and hormone therapy. For example, in treating breast cancer, neoadjuvant therapy can allows patients with large breast cancer to undergo breast-conserving surgery.

The "normal" level of expression and/or activity of a biomarker is the level of expression and/or activity of the biomarker in cells of a subject, e.g., a human patient, not afflicted with a cancer. An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples. The same determination can be made to determine overactivity or underactivity.

Probiotic Bacteria

In some embodiments, the instant invention is drawn to a composition comprising at least one probiotic bacterial strain, capable of regulating NK cell function. Such probiotic bacteria induce significant split anergy in activated NK cells, leading to a significant induction of IFN-γ and TNF-α. In addition, such probiotic bacteria induce significant expansion of NK cells.

Many commercial probiotics are available, having various effects of reducing gastrointestinal discomfort or strengthening of the immune system. Preferred probiotic bacteria species for use in the compositions and methods described herein include those commercially available strains of probiotic bacteria, especially those from the *Streptococcus* (e.g., *S. thermophilus*), *Bifidobacterium* (e.g., *B. longum, B. breve, B. infantis, B. breve, B. infantis*), and *Lactobacillus* genera (e.g., *L. acidophilus, L. helveticus, L. bulgaricus, L. rhamnosus, L. plantarum*, and *L. casei*). The instant disclosure comprising methods of administering at least one probiotic bacterial strain, preferably a combination of two or more different bacterial strains, to a subject, preferably a mammal (e.g., a human). Such administration may be systemically or locally (e.g., directly to intestines) performed. A preferably administration route is oral administration. Other routes (e.g., rectal) may be also used. For administration, either the bacteria (e.g., in a wet, sonicated, grounded, or dried form or formula), the bacterial culture medium containing the bacteria, or the bacterial culture medium supernatant (not containing the bacteria), may be administered.

Osteoclasts

Osteoclasts are a type of bone cell, derived from hematopoietic stem cells. Their function, resorbing bone tissue, is critical for the maintenance, repair, and remodeling of bones. Bone homeostasis is achieved when there is a balance between osteoblast bone formation and osteoclast bone resorption. Osteoclasts mature through stimulation from osteoblasts expressing RANKL, and their interaction, mediated by firm adhesion via ICAM-1. Osteoclasts also express many ligands for receptors present on activated NK cells. They reported that osteoclasts express ULBP-1, ULBP-2/5/6 and ULBP-3, but little or no MIC-A, MIC-B, or MHC class I-like ligands for NKG2D, the activating receptor of NK cells.

Osteoclasts (OCs), in comparison to dendritic cells (DCs) and monocytes, are significant activators of NK cell expansion and function (Tseng et al. (2015) Oncotarget 6(24): 20002-25). Additionally, osteoclasts secrete significant amounts of IL-12, IL-15, IFN-γ and IL-18, which are known to activate NK cells; osteoclasts also express important NK-activating ligands. The instant disclosure provides a novel strategy on how to expand highly functional, supercharged, osteoclast-expanded NK cells to levels that are significantly higher than those established by other methodologies. Several in vitro NK expansion techniques have been developed to establish a higher therapeutic cell dosage, while boosting activity and in vivo proliferative potential of NK cells. Some of these techniques include the stimulation of peripheral blood mononuclear cells (PBMCs), PBMC-purified populations of NK cells, or the use of human cord blood, sometimes in combination with various feeder cells such as K562 cells expressing membrane-bound IL-15 and 41BB ligand (K562-mb15-41BBL), EBV-TM-LCL, Wilm's tumor or irradiated PBMCs. These studies have generated clinically relevant NK cell numbers that have good function.

The instant disclosure provides a novel method to expand NK cells using osteoclasts, resulting in enhanced sensitization of tumor target cells to NK cell-mediated apoptosis, as well as cytokine production.

The term "pre-determined" biomarker amount and/or activity measurement(s) may be a biomarker amount and/or activity measurement(s) used to, by way of example only, evaluate a subject that may be selected for a particular treatment, evaluate a response to a treatment such as using a composition comprising at least one probiotic bacterial strain, alone or in combination with other NK immunotherapies, and/or evaluate the disease state. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary to reflect differences among specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In certain embodiments, the amounts determined and/or compared in a method described herein are based on absolute measurements. In other embodiments, the amounts determined and/or compared in a method described herein are based on relative measurements, such as ratios (e.g., serum biomarker normalized to the expression of housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In some embodiments, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

The term "predictive" includes the use of a biomarker nucleic acid and/or protein status, e.g., over- or under-activity, emergence, expression, growth, remission, recurrence or resistance of tumors before, during or after therapy, for determining the likelihood of response of a cancer to a therapy with a composition comprising at least one of probiotic bacteria, alone or in combination with other NK immunotherapies. Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC), or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its absolute or relatively modulated presence or absence in clinical subset of patients with cancer (e.g., those responding to a composition comprising at least one of probiotic bacteria, alone or in combination with other NK immunotherapies or those developing resistance thereto).

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of cancer (e.g., solid tumors, such as esophageal cancer and gastric cancer), development of one or more clinical factors, or recovery from the disease.

The term "response to anti-cancer therapy" or "response to a therapy with a composition comprising at least one of probiotic bacteria, alone or in combination with other NK immunotherapies" relates to any response of the hyperproliferative disorder (e.g., cancer) to an anti-cancer agent(s) such as treatment with a composition comprising at least one of probiotic bacteria, alone or in combination with other NK immunotherapies, preferably to a change in tumor mass and/or volume after initiation of neoadjuvant or adjuvant therapy.

Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for which biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a cancer therapy can be determined using well-known methods in the art, such as those described in the Examples section.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal that is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., p<0.05) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The terms "response" or "responsiveness" refers to an anti-cancer response, such as in the sense of reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit a favorable response (i.e., will exhibit a lack of response or be non-responsive).

The term "sample" used for detecting or determining the presence or level of at least one biomarker is typically brain tissue, cerebrospinal fluid, whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "sensitize" means to alter cancer cells or tumor cells in a way that allows for more effective treatment of the associated cancer with a cancer therapy (e.g., by treating with the compositions described herein). In some embodiments, normal cells are not affected to an extent that causes the normal cells to be unduly injured. An increased sensitivity or a reduced sensitivity to a therapeutic treatment is measured according to a known method in the art for the particular treatment and methods described herein below, including, but not limited to, cell proliferative assays (Tanigawa et al. (1982) *Cancer Res.* 42:2159-2164), cell death assays (Weisenthal et al. (1984) *Cancer Res.* 94:161-173; Weisenthal et al. (1985) *Cancer Treat. Rep.* 69:615-632; Weisenthal L M, In: Kaspers et al. eds. Drug Resistance in Leukemia and Lymphoma. Langhorne, P A: Harwood Academic Publishers, 1993: 415-432; Weisenthal et al. (1994) *Contrib. Gynecol. Obstet.* 19:82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

The term "specific binding" refers to an agent, such as an antibody, binding to a pre-determined target, such as an antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE® assay instrument using an antigen of interest as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen." Selective binding is a relative term referring to the ability of an antibody to discriminate the binding of one antigen over another.

The term "synergistic effect" refers to the combined effect of two or more anti-cancer agents (e.g., treatment with a combination of a composition comprising at least one of probiotic bacteria, alone or in combination with other NK immunotherapies) can be greater than the sum of the separate effects of the anti-cancer agents alone.

The term "subject" refers to any healthy animal, mammal or human, or any animal, mammal or human afflicted with a cancer, e.g., brain metastasis, lung, ovarian, pancreatic, liver, breast, prostate, colon carcinomas, melanoma, multiple myeloma, and the like. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

A "transcribed polynucleotide" or "nucleotide transcript" is a polynucleotide (e.g., an mRNA, hnRNA, a cDNA, or an analog of such RNA or cDNA) which is complementary to or homologous with (or identical to) all or a portion of a mature mRNA made by transcription of a biomarker nucleic acid and normal post-transcriptional processing (e.g., splicing), if any, of the RNA transcript, and reverse transcription of the RNA transcript.

As used herein, the term "unresponsiveness" includes refractivity of cancer cells to therapy or refractivity of therapeutic cells, such as immune cells, to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134).

There is a known and definite correspondence between the amino acid sequence of a particular protein and the nucleotide sequences that can code for the protein, as defined by the genetic code. Likewise, there is a known and definite correspondence between the nucleotide sequence of a particular nucleic acid and the amino acid sequence encoded by that nucleic acid, as defined by the genetic code.

An important and well-known feature of the genetic code is its redundancy, whereby, for most of the amino acids used to make proteins, more than one coding nucleotide triplet may be employed. Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence.

Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for the loci and biomarkers of the present invention are well-known in the art and readily available on publicly available databases, such as the National Center for Biotechnology Information (NCBI).

II. Subjects

In certain embodiments, the subject suitable for the compositions and methods disclosed herein is a mammal (e.g., mouse, rat, primate, non-human mammal, domestic animal, such as a dog, cat, cow, horse, and the like), and is preferably a human. In other embodiments, the subject is an animal model of a cancer. For example, the animal model can be an orthotopic xenograft animal model of human oral squamous carcinoma, or comprising cancer stem cells (CSCs)/undifferentiated tumors.

In other embodiments of the methods of the present invention, the subject has not undergone treatment, such as chemotherapy, radiation therapy, targeted therapy, and/or anti-immune therapy (such as NK cell-related immunotherapies). In still other embodiments, the subject has undergone treatment, such as chemotherapy, radiation therapy, targeted therapy, and/or anti-immune therapy (such as NK cell-related immunotherapies).

In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

The methods of the present invention can be used to treat and/or determine the responsiveness to a composition comprising at least one of probiotic bacteria, alone or in combination with other NK immunotherapies, of many different cancers in subjects such as those described herein.

III. Anti-Cancer Therapies

In one aspect, other anti-cancer therapies and/or immunotherapies combination or combinations of therapies (e.g., one or more PI3Kbeta-selective inhibitors, such as KIN193, in combination with one or more immune checkpoint inhibitors, such as an anti-PD-1 antibody, either alone or in combination with yet additional anti-cancer therapies, such as targeted therapy) can be administered, particularly if a subject has first been indicated as being a likely responder to a composition as disclosed herein. In other embodiments, such therapy can be avoided once a subject is indicated as not being a likely responder to such therapy and an alternative treatment regimen, such as targeted and/or untargeted anti-cancer therapies can be administered together with the composition as disclosed herein.

Combination therapies are also contemplated and can comprise, for example, one or more chemotherapeutic agents and radiation, one or more chemotherapeutic agents and immunotherapy, or one or more chemotherapeutic agents, radiation and chemotherapy, each combination of which can be with a therapy as disclosed herein. As described below, agents can be administered in combination therapy with, e.g., chemotherapeutic agents, hormones, anti-angiogens, radiolabelled, compounds, or with surgery, cryotherapy, and/or radiotherapy. The preceding treatment methods can be administered in conjunction with other forms of conventional therapy (e.g., standard-of-care treatments for cancer well-known to the skilled artisan), either consecutively with, pre- or post-conventional therapy. For example, these modulatory agents can be administered with a therapeutically effective dose of chemotherapeutic agent. In other embodiments, these modulatory agents are administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regimen and dosages of these aforementioned chemotherapeutic drugs that are therapeutically effective will depend on the particular melanoma, being treated, the extent of the disease and other factors familiar to the physician of skill in the art and can be determined by the physician.

The term "targeted therapy" refers to administration of agents that selectively interact with a chosen biomolecule to thereby treat cancer. One example includes breast or ovarian cancer antigens.

Alternatively, immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In certain embodiments, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolites, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well-known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. No. Re. 36,397); and NU1025 (Bowman et al.). The mechanism of action is generally related to the ability of PARP inhibitors to bind PARP and decrease its activity. PARP catalyzes the conversion of .beta.-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H, et al. (2005) Nature 434:917-921). The foregoing examples of chemotherapeutic agents are illustrative, and are not intended to be limiting.

In other embodiments, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (1-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In yet other embodiments, surgical intervention can physically remove cancerous cells and/or tissues.

In still other embodiments, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In yet other embodiments, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still other embodiments, photodynamic therapy (also called PDT, photoradiation therapy, phototherapy, or photochemotherapy) is used for the treatment of some types of cancer.

In yet other embodiments, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors.

The duration and/or dose of treatment with therapies may vary according to the particular therapeutic agent or combination thereof. An appropriate treatment time for a particular cancer therapeutic agent will be appreciated by the skilled artisan. The present invention contemplates the continued assessment of optimal treatment schedules for each cancer therapeutic agent, where the phenotype of the cancer of the subject as determined by the methods of the present invention is a factor in determining optimal treatment doses and schedules.

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

Clinical efficacy can be measured by any method known in the art. For example, the response to a therapy, such as a composition as disclosed herein, relates to any response of the cancer, e.g., a tumor, to the therapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., *J. Clin. Oncol.* (2007) 25:4414-4422) or Miller-Payne score (Ogston et al., (2003) *Breast* (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular therapeutic regimen is at least 25%, 30%, 35%, 40%, 45%, 50%, 55%, 60%, 65%, 70%, 75%, 80%, 85%, or more.

Additional criteria for evaluating the response to a therapy as disclosed herein are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular anti-cancer therapeutic regimen can be administered to a population of subjects and the outcome can be correlated to biomarker measurements that were determined prior to administration of any composition as disclosed herein. The outcome measurement may be pathologic response to therapy given in the neoadjuvant setting. Alternatively, outcome measures, such as overall survival and disease-free survival can be monitored over a period of time for subjects following a therapy for whom biomarker measurement values are known. In certain embodiments, the same doses of a therapeutic composition are administered to each subject. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a therapy as disclosed herein can be determined using methods such as those described in the Examples section.

3. Pharmaceutical Compositions

The present invention provides pharmaceutically acceptable compositions of the compositions disclosed herein. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles.

Compositions described herein may be used for oral administration to the gastrointestinal tract, directed at the objective of introducing the probiotic bacteria to tissues of the gastrointestinal tract. The formulation for a therapeutic composition of the present invention may also include other probiotic agents or nutrients which promote spore germination and/or bacterial growth. An exemplary material is a bifidogenic oligosaccharide, which promotes the growth of beneficial probiotic bacteria. In certain embodiment, the probiotic bacterial strain is combined with a therapeutically-effective dose of an (preferably, broad spectrum) antibiotic, or an anti-fungal agent. In some embodiments, the compositions described herein are encapsulated into an enterically-coated, time-released capsule or tablet. The enteric coating allows the capsule/tablet to remain intact (i.e., undissolved) as it passes through the gastrointestinal tract, until after a certain time and/or until it reaches a certain part of the GI tract (e.g., the small intestine). The time-released component prevents the "release" of the probiotic bacterial strain in the compositions described herein for a pre-determined time period.

The therapeutic compositions of the present invention may also include known antioxidants, buffering agents, and other agents such as coloring agents, flavorings, vitamins or minerals.

In some embodiments, the therapeutic compositions of the present invention are combined with a carrier which is physiologically compatible with the gastrointestinal tissue of the species to which it is administered. Carriers can be comprised of solid-based, dry materials for formulation into tablet, capsule or powdered form; or the carrier can be comprised of liquid or gel-based materials for formulations into liquid or gel forms. The specific type of carrier, as well as the final formulation depends, in part, upon the selected route(s) of administration. The therapeutic composition of the present invention may also include a variety of carriers and/or binders. A preferred carrier is micro-crystalline cellulose (MCC) added in an amount sufficient to complete the one gram dosage total weight. Carriers can be solid-based dry materials for formulations in tablet, capsule or powdered form, and can be liquid or gel-based materials for formulations in liquid or gel forms, which forms depend, in part, upon the routes of administration. Typical carriers for dry formulations include, but are not limited to: trehalose, malto-dextrin, rice flour, microcrystalline cellulose (MCC) magnesium sterate, inositol, FOS, GOS, dextrose, sucrose, and like carriers. Suitable liquid or gel-based carriers include but are not limited to: water and physiological salt solutions; urea; alcohols and derivatives (e.g., methanol, ethanol, propanol, butanol); glycols (e.g., ethylene glycol, propylene glycol, and the like). Preferably, water-based carriers possess a neutral pH value (i.e., pH 7.0). Other carriers or agents for administering the compositions described herein are known in the art, e.g., in U.S. Pat. No. 6,461,607.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of one or more bacterial strains as disclosed herein.

The present invention also encompasses kits for detecting and/or modulating biomarkers described herein. A kit of the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or standards). A kit may additionally include buffers and other reagents recognized for use in a method of the disclosed invention. Non-limiting examples include agents to reduce non-specific binding, such as a carrier protein or a detergent.

Further Uses and Methods of the Present Invention

The compositions described herein can be used in a variety of diagnostic, prognostic, and therapeutic applications. In any method described herein, such as a diagnostic method, prognostic method, therapeutic method, or combination thereof, all steps of the method can be performed by a single actor or, alternatively, by more than one actor. For example, diagnosis can be performed directly by the actor providing therapeutic treatment. Alternatively, a person providing a therapeutic agent can request that a diagnostic assay be performed. The diagnostician and/or the therapeutic interventionist can interpret the diagnostic assay results to determine a therapeutic strategy. Similarly, such alternative processes can apply to other assays, such as prognostic assays.

1) Predictive Medicine

The present invention can pertain to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining the amount and/or activity level of a biomarker (e.g., cytokines and/or chemokines, such as those listed in Table 1) described herein in the context of a biological sample (e.g., blood, serum, cells, or tissue) to thereby determine whether an individual afflicted with a cancer is likely to respond to a composition as disclosed herein, such as in cancers. Such assays can be used for prognostic or predictive purpose alone, or can be coupled with a therapeutic intervention to thereby prophylactically treat an individual prior to the onset or after recurrence of a disorder characterized by or associated with biomarker polypeptide, nucleic acid expression or activity. The skilled artisan will appreciate that any method can use one or more (e.g., combinations) of biomarkers described herein, such as those in the tables, figures, examples, and otherwise described in the specification.

2) Diagnostic Assays

The present invention provides, in part, methods, systems, and code for accurately classifying whether a biological sample is associated with a cancer that is likely to respond to a composition as disclosed herein. In some embodiments, the present invention is useful for classifying a sample (e.g., from a subject) as associated with or at risk for responding to or not responding to a composition as disclosed herein using a statistical algorithm and/or empirical data (e.g., the amount or activity of a biomarker described herein, such as in the tables, figures, examples, and otherwise described in the specification).

An exemplary method for detecting the amount or activity of a biomarker described herein, and thus useful for classifying whether a sample is likely or unlikely to respond to a composition as disclosed herein involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the biomarker in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely therapy responder or progressor sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well-known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the sample classification results to a clinician, e.g., an oncologist.

In other embodiments, the diagnosis of a subject is followed by administering to the individual a therapeutically effective amount of a defined treatment based upon the diagnosis.

In some embodiments, the methods further involve obtaining a control biological sample (e.g., biological sample from a subject who does not have a cancer or whose cancer is susceptible to a composition as disclosed herein), a biological sample from the subject during remission, or a biological sample from the subject during treatment for developing a cancer progressing despite a composition as disclosed herein.

3) Prognostic Assays

The diagnostic methods described herein can furthermore be utilized to identify subjects having or at risk of developing a cancer that is likely or unlikely to be responsive to a composition as disclosed herein. The assays described herein, such as the preceding diagnostic assays or the following assays, can be utilized to identify a subject having or at risk of developing a disorder associated with a misregulation of the amount or activity of at least one biomarker described herein, such as in cancer. Alternatively, the prognostic assays can be utilized to identify a subject having or at risk for developing a disorder associated with a misregulation of the at least one biomarker described herein, such as in cancer. Furthermore, the prognostic assays described herein can be used to determine whether a subject can be administered a composition as disclosed herein and/or an additional therapeutic regimen to treat a disease or disorder associated with the aberrant biomarker expression or activity.

4) Biomarker Nucleic Acids and Polypeptides

The therapeutic and other methods of the present invention relate to certain biomarkers of interest. In some embodiments, the biomarkers of interest are isolated nucleic acid molecules that correspond to biomarker nucleic acids that encode a biomarker polypeptide or a portion of such a polypeptide. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

A biomarker nucleic acid molecule of the present invention can be isolated using standard molecular biology techniques and the sequence information in the database records described herein. Using all or a portion of such nucleic acid sequences, nucleic acid molecules of the present invention can be isolated using standard hybridization and cloning techniques (e.g., as described in Sambrook et al., ed., *Molecular Cloning: A Laboratory Manual,* 2nd ed., Cold Spring Harbor Laboratory Press, Cold Spring Harbor, N Y, 1989).

A nucleic acid molecule of the present invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of interest can be prepared by standard synthetic techniques, e.g., using an automated DNA synthesizer.

Moreover, a nucleic acid molecule useful in such methods can comprise only a portion of a nucleic acid sequence, wherein the full length nucleic acid sequence comprises a marker of interest or which encodes a polypeptide corresponding to a marker of interest. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a biomarker nucleic acid sequence. Probes based on the sequence of a biomarker nucleic acid molecule can be used to detect transcripts or genomic sequences corresponding to one or more markers of interest. The probe comprises a label group attached thereto, e.g., a radioisotope, a fluorescent compound, an enzyme, or an enzyme co-factor.

A biomarker nucleic acid molecules that differ, due to degeneracy of the genetic code, from the nucleotide sequence of nucleic acid molecules encoding a protein which corresponds to the biomarker, and thus encode the same protein, are also contemplated.

In addition, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, biomarker alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than $1/100$ or $1/1000$ members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect on the function of the protein.

As used herein, the terms "gene" and "recombinant gene" refer to nucleic acid molecules comprising an open reading frame encoding a polypeptide corresponding to a marker of the present invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the present invention.

As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5%

(by dry weight) of chemical precursors or compounds other than the polypeptide of interest.

5) Analyzing Biomarker Nucleic Acids and Polypeptides

For any method described herein, biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

a. Methods for Detection of Biomarker Copy Number

Methods of evaluating the copy number of a biomarker nucleic acid are well-known to those of skill in the art. The presence or absence of chromosomal gain or loss can be evaluated simply by a determination of copy number of the regions or markers identified herein.

Methods of evaluating the copy number of a biomarker locus include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In some embodiments, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods suitable to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. In some embodiments, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In an alternative use of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well-known in the art (see, e.g., U.S. Pat. Nos. 6,335,167; 6,197,501; 5,830,645; and 5,665, 549 and Albertson (1984) *EMBO J.* 3: 1227-1234; Pinkel (1988) *Proc. Natl. Acad. Sci. USA* 85: 9138-9142; EPO Pub.

No. 430,402; *Methods in Molecular Biology*, Vol. 33: In situ Hybridization Protocols, Choo, ed., Humana Press, Totowa, N.J. (1994), etc.) In other embodiments, the hybridization protocol of Pinkel, et al. (1998) *Nature Genetics* 20: 207-211, or of Kallioniemi (1992) *Proc. Natl Acad Sci USA* 89:5321-5325 (1992) is used.

In still other embodiments, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g., healthy tissue, provides a measure of the copy number.

Methods of "quantitative" amplification are well-known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the present invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Loss of heterozygosity (LOH) and major copy proportion (MCP) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

b. Methods for Detection of Biomarker Nucleic Acid Expression

Biomarker expression may be assessed by any of a wide variety of well-known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In other embodiments, detecting or determining expression levels of a biomarker and functionally similar homologs thereof, including a fragment or genetic alteration thereof (e.g., in regulatory or promoter regions thereof) comprises detecting or determining RNA levels for the marker of interest. In some embodiments, one or more cells from the subject to be tested are obtained and RNA is isolated from the cells.

In certain embodiments, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) *Science* 278: 1481; Emmert-Buck et al. (1996) *Science* 274:998; Fend et al. (1999) *Am. J. Path.* 154: 61 and Murakami et al. (2000) *Kidney Int.* 58:1346). For example, Murakami et al., supra, describe isolation of a cell from a previously immunostained tissue section.

It is also possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in preferred embodiments, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) *J. Immunol. Methods* 190:199. Care to avoid RNA degradation must be taken, e.g., by inclusion of RNAsin.

The RNA sample can then be enriched in particular species. In some embodiments, poly(A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, NY).

In preferred embodiments, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) PNAS 86, 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)); and transcription amplification (see, e.g., Kwoh et al., Proc. Natl. Acad. Sci. USA 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well-known in the art (see, e.g., U.S. Pat. Nos: 6,618,6796; 6,379,897; 6,664,377; 6,451,536; 548,257; U.S. 20030157485 and Schena et al. (1995) Science 20, 467-470; Gerhold et al. (1999) *Trends In Biochem. Sci.* 24, 168-173; and Lennon et al. (2000) *Drug Discovery Today* 5, 59-65, which are herein incorporated by reference in their entirety).

Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In certain embodiments, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In some embodiments, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In other embodiments, hybridization under "stringent conditions" occurs when there is at least 97% identity between the sequences.

The form of labeling of the probes may be any that is appropriate, such as the use of radioisotopes, for example, 32P and 35S. Labeling with radioisotopes may be achieved, whether the probe is synthesized chemically or biologically, by the use of suitably labeled bases.

In certain embodiments, the biological sample contains polypeptide molecules from the test subject. Alternatively, the biological sample can contain mRNA molecules from the test subject or genomic DNA molecules from the test subject.

In other embodiments, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

c. Methods for Detection of Biomarker Protein Expression

The activity or level of a biomarker protein can be detected and/or quantified by detecting or quantifying the expressed polypeptide. The polypeptide can be detected and quantified by any of a number of means well-known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to a composition as disclosed herein. Any method known in the art for detecting polypeptides can be used. Such methods include, but are not limited to, immunodiffusion, immunoelectrophoresis, radioimmunoassay (RIA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and RIA procedures may be conducted such that a desired biomarker protein standard is labeled (with a radioisotope such as $^{125}$I or $^{35}$S, or an assayable enzyme, such as horseradish peroxidase or alkaline phosphatase), and, together with the unlabeled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker protein antibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting the mixture with labeled antibody. Other conventional methods may also be employed as suitable.

In certain embodiments, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabeling. The assay is scored visually, using microscopy.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$ M, $10^{-7}$M, $10^{-8}$M, $10^{-9}$M, $10^{-10}$ M, $10^{-11}$ M, $10^{-12}$ M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies may be commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab')$_2$ fragments can be used. Such fragments can be produced by enzymatic cleavage or by recombinant techniques. For example, papain or pepsin cleavage can generate Fab or F(ab')$_2$ fragments, respectively. Other proteases with the requisite substrate specificity can also be used to generate Fab or F(ab')$_2$ fragments. Antibodies can also be produced in a variety of truncated forms using antibody genes in which one or more stop codons have been introduced upstream of the natural stop site. For example, a chimeric gene encoding a F(ab')$_2$ heavy chain portion can be designed to include DNA sequences encoding the CH$_1$ domain and hinge region of the heavy chain.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

d. Sampling Methods

In some embodiments, biomarker amount and/or activity measurement(s) in a sample from a subject is compared to a predetermined control (standard) sample. The sample from the subject is typically from a diseased tissue, such as cancer cells or tissues. The control sample can be from the same subject or from a different subject. The control sample is typically a normal, non-diseased sample. However, in some embodiments, such as for staging of disease or for evaluating the efficacy of treatment, the control sample can be from a diseased tissue. The control sample can be a combination of samples from several different subjects. In some embodiments, the biomarker amount and/or activity measurement(s) from a subject is compared to a pre-determined level. This pre-determined level is typically obtained from normal samples. As described herein, a "pre-determined" biomarker amount and/or activity measurement(s) may be a biomarker amount and/or activity measurement(s) used to, by way of example only, evaluate a subject that may be selected for treatment (e.g., based on the number of genomic mutations and/or the number of genomic mutations causing non-functional proteins for DNA repair genes), evaluate a response to a composition as disclosed herein, alone or in combination with other NK immunotherapies and with one or more additional anti-cancer therapies. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In some embodiments, the amounts determined and/or compared in a method described herein are based on absolute measurements.

In other embodiments, the amounts determined and/or compared in a method described herein are based on relative measurements, such as ratios (e.g., biomarker copy numbers, level, and/or activity before a treatment vs. after a treatment, such biomarker measurements relative to a spiked or man-made control, such biomarker measurements relative to the expression of a housekeeping gene, and the like). For example, the relative analysis can be based on the ratio of pre-treatment biomarker measurement as compared to post-treatment biomarker measurement. Pre-treatment biomarker measurement can be made at any time prior to initiation of anti-cancer therapy. Post-treatment biomarker measurement can be made at any time after initiation of anti-cancer therapy. In some embodiments, post-treatment biomarker measurements are made 1, 2, 3, 4, 5, 6, 7, 8, 9, 10, 11, 12, 13, 14, 15, 16, 17, 18, 19, 20 weeks or more after initiation of anti-cancer therapy, and even longer toward indefinitely for continued monitoring. Treatment can comprise anti-cancer therapy, such as a therapeutic regimen comprising a composition as disclosed herein, or further in combination with other anti-cancer agents.

The pre-determined biomarker amount and/or activity measurement(s) can be any suitable standard. For example, the pre-determined biomarker amount and/or activity measurement(s) can be obtained from the same or a different human for whom a patient selection is being assessed. In some embodiments, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments of the present invention the change of biomarker amount and/or activity measurement(s) from the pre-determined level is about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 fold or greater, or any range in between, inclusive. Such cutoff values apply equally when the measurement is based on relative changes, such as based on the ratio of pre-treatment biomarker measurement as compared to post-treatment biomarker measurement.

Biological samples can be collected from a variety of sources from a patient including a body fluid sample, cell sample, or a tissue sample comprising nucleic acids and/or proteins. "Body fluids" refer to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In preferred embodiments, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In some embodiments, the sample is serum, plasma, or urine. In other embodiments, the sample is serum.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the present invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CIEF), capillary isotachophoresis (cITP) and capillary electrochromatography (CEC). CE techniques can be coupled to electrospray ionization through the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CLEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

EXAMPLES

Example 1: Materials and Methods for Examples 2-3

Cell Lines, Reagents, and Antibodies

Human immune cells were cultured in RPMI 1640, supplemented with 10% fetal bovine serum (FBS) (Gemini Bio-Products, CA). Oral squamous carcinoma stem cells (OSCSCs) were isolated from oral cancer patient tongue tumors at UCLA School of Medicine and cultured in RPMI 1640, supplemented 10% FBS (Gemini Bio-Products, CA), 1.4% antibiotic antimycotic, 1% sodium pyruvate, 1.4% MEM non-essential amino acids, 1% L-glutamine, 0.2% gentimicin (Gemini Bio-products, CA) and 0.15% sodium bicarbonate (Fisher Scientific, PA).

Antibodies to CD16 were purchased from Biolegend (San Diego, CA, USA). Recombinant IL-2 was obtained from NIH-BRB. Antibodies against isotype control, MHC-I, CD45 (human), CD45 (mouse), CD3, CD16, CD56, CD8, HLADR, and CD11b were purchased from Biolegend (San Diego, CA). Human NK purification kits were obtained from Stem Cell Technologies (Vancouver, BC, Canada).

Human monocytes/osteoclasts were cultured in alpha-MEM medium (Life Technologies, CA), supplemented with 10% FBS, and penicillin-streptomycin (Gemini Bio-Products, CA). Human M-CSF (Biolegend, CA) and soluble RANKL (PeproTech, NJ) were dissolved in alpha-MEM and stored at −80° C.

Bacteria Selection and Preparation

AJ2 is a combination of 8 different strains of gram positive probiotic bacteria (*Streptococcus thermophilus, Bifidobacterium longum, Bifidobacterium breve, Bifidobacterium infantis, Lactobacillus acidophilus, Lactobacillus plantarum, Lactobacillus paracasei,* KE99 and *Lactobacillus bulgaricus*) used to induce differentiation of stem cells.

Different strains of probiotic bacteria were tested for their ability to induce IFN-g as well as a number of important cytokines, chemokines and growth factors (Table 1). To assess the levels of each strain used in the combination we used an activation index established in the lab for the NK cells which consisted of the use of a specific ratio of several important cytokines and chemokines that prevented autoimmunity while enhancing significant activation of NK cells under pathological conditions. Therefore, the strains were selected to: 1) provide regulated activation of NK cells when no activation of NK cells is desired; 2) when activated by cytokines and/or cross-linking of the important receptors which occurs during functional activation of NK cells in cancer is to induce maximal activation of NK cells; and 3) provide diversity for gut microflora. These criteria allow us to use bacteria to regulate the gut mucosal immunity in such a way that we will only increase NK activation when needed during infections or malignancies. In other words when there is no need for function of NK cells bacteria will regulate NK function to not induce inflammation; however, during need which occurs under the pathological conditions NK cells are triggered to function at the maximal levels. Such coordinated regulation of NK cell function should be effective in halting unwanted inflammation while providing effective and maximal immunity during disease.

AJ2 was weighed and resuspended in RPMI Medium 1640 containing 10% FBS at a concentration of 10 mg per 1 mL. The bacteria were thoroughly vortexed, then sonicated on ice for 15 seconds, at 6 to 8 amplitude. Sonicated samples were then incubated for 30 seconds on ice. After every five pulses, a sample was taken to observe under the microscope until at least 80 percent of cell walls were lysed. It was determined that approximately 20 rounds of sonication/incubation on ice, were conducted to achieve complete sonication. Finally, the sonicated samples (sAJ2) were aliquoted and stored in a −80 degrees Celsius freezer.

Purification of NK Cells from the Peripheral Blood

Written informed consents, approved by UCLA Institutional Review Board (IRB), were obtained from healthy blood donors, and all procedures were approved by the UCLA-IRB. Peripheral blood was separated using Ficoll-Hypaque centrifugation, after which the white, cloudy layer, containing peripheral blood mononuclear cells (PBMC), was harvested, washed and re-suspended in RPMI 1640 (Invitrogen by Life Technologies, CA) supplemented with 10% FBS and plated on plastic tissue culture dishes. After 1-2 hours of incubation, non-adherent, human peripheral blood lymphocytes (PBL) were collected. NK cells were negatively selected and isolated from PBLs using the Easy-Sep® Human NK cell enrichment kit purchased from Stem Cell Technologies (Vancouver, BC, Canada). Isolated NK cells were stained with anti-CD16 antibody, to measure NK cell purity using flow cytometric analysis. The isolated NK cell population was greater than 90% purity. Purified NK cells were cultured in RPMI Medium 1640 supplemented with 10% FBS (Gemini Bio-Products, CA), 1% antibiotic antimycotic, 1% sodium pyruvate, and 1% MEM non-essential amino acids (Invitrogen, Life Technologies, CA).

TABLE 1

| Cytokines, Growth Factors, and chemokines | | | | | | | | | |
|---|---|---|---|---|---|---|---|---|---|
| Bacterias | Treatments | IL-6 | IFN-γ | IL-1ra | TNF-α | IL-1B | IL-10 | IL-12p70 | G-CSF |
| Control | NK | 38 | 34 | 41 | 44 | 4 | 6 | 2 | 28 |
|  | NK + IL-2 | 55 | 99 | 439 | 137 | 10 | 6 | 5 | 54 |
|  | NK + IL-2 + anti-CD16 mAb | 39 | 138 | 466 | 166 | 22 | 8 | 7 | 65 |
| AJ2 | NK | 20292 | 222 | 308 | 9634 | 1041 | 200 | 83 | 725 |
|  | NK + IL-2 | 6034 | 894 | 425 | 2166 | 454 | 38 | 70 | 221 |
|  | NK + IL-2 + anti-CD16 mAb | 7944 | 1219 | 618 | 3883 | 839 | 51 | 72 | 350 |
| S. thermophilus | NK | 10222 | 785 | 229 | 18892 | 1381 | 63 | 515 | 149 |
|  | NK + IL-2 | 1773 | 1188 | 465 | 2413 | 390 | 17 | 132 | 87 |
|  | NK + IL-2 + anti-CD16 mAb | 2475 | 2594 | 434 | 4917 | 642 | 23 | 163 | 101 |
| B. breve | NK | 9726 | 99 | 196 | 2904 | 200 | 127 | 10 | 363 |
|  | NK + IL-2 | 3402 | 284 | 470 | 1868 | 165 | 36 | 21 | 138 |
|  | NK + IL-2 + anti-CD16 mAb | 7261 | 844 | 565 | 1498 | 421 | 68 | 26 | 289 |
| B. longum | NK | 60895 | 158 | 312 | 5880 | 813 | 298 | 42 | 938 |
|  | NK + IL-2 | 7287 | 671 | 472 | 2896 | 408 | 52 | 47 | 244 |
|  | NK + IL-2 + anti-CD16 mAb | 2916 | 1282 | 461 | 4240 | 498 | 68 | 33 | 386 |
| L. acidophilus | NK | 10357 | 366 | 181 | 6858 | 819 | 62 | 299 | 141 |
|  | NK + IL-2 | 2095 | 1329 | 487 | 1151 | 335 | 17 | 136 | 89 |
|  | NK + IL-2 + anti-CD16 mAb | 3684 | 2715 | 493 | 5663 | 654 | 24 | 155 | 102 |
| L. bulgaricus | NK | 2518 | 144 | 112 | 868 | 293 | 22 | 25 | 77 |
|  | NK + IL-2 | 837 | 381 | 449 | 439 | 123 | 12 | 21 | 69 |
|  | NK + IL-2 + anti-CD16 mAb | 685 | 306 | 383 | 1064 | 141 | 9 | 5 | 59 |
| L. paracasei | NK | 3029 | 186 | 129 | 3809 | 320 | 70 | 70 | 106 |
|  | NK + IL-2 | 7285 | 2112 | 551 | 6776 | 523 | 47 | 125 | 138 |
|  | NK + IL-2 + anti-CD16 mAb | 6867 | 2145 | 573 | 10128 | 721 | 43 | 123 | 153 |
| L. plantarum | NK | 9500 | 282 | 323 | 13887 | 645 | 85 | 130 | 236 |
|  | NK + IL-2 | 4212 | 5484 | 500 | 9223 | 466 | 43 | 184 | 129 |
|  | NK + IL-2 + anti-CD16 mAb | 3679 | 3087 | 575 | 7942 | 714 | 37 | 155 | 125 |
| B. infantis | NK | 6136 | 275 | 179 | 5728 | 249 | 55 | 66 | 145 |
|  | NK + IL-2 | 6618 | 3073 | 459 | 5103 | 422 | 41 | 115 | 190 |
|  | NK + IL-2 + | 3927 | 1250 | 434 | 5287 | 365 | 34 | 47 | 151 |

TABLE 1-continued

Cytokines, Growth Factors, and chemokines

| Bacterias | Treatments | IL-8 | GM-CSF | RANTES | Eotaxin | IP-10 | IL-13 | MCP-1 | IL-17 |
|---|---|---|---|---|---|---|---|---|---|
| Control | NK | 281 | 86 | 2564 | 5 | 64 | 2 | 258 | 33 |
|  | NK + IL-2 | 1148 | 100 | 3151 | 12 | 137 | 5 | 525 | 51 |
|  | NK + IL-2 + anti-CD16 mAb | 1480 | 102 | 2536 | 20 | 114 | 5 | 305 | 58 |
| AJ2 | NK | 12107 | 121 | 1797 | 23 | 40 | 7 | 526 | 54 |
|  | NK + IL-2 | 2430 | 113 | 1440 | 17 | 34 | 7 | 104 | 50 |
|  | NK + IL-2 + anti-CD16 mAb | 6503 | 201 | 2704 | 35 | 51 | 23 | 107 | 72 |
| S. thermophilus | NK | 3326 | 131 | 2580 | 40 | 64 | 9 | 502 | 74 |
|  | NK + IL-2 | 1341 | 124 | 2197 | 21 | 45 | 9 | 169 | 65 |
|  | NK + IL-2 + anti-CD16 mAb | 1841 | 177 | 2097 | 29 | 58 | 15 | 332 | 57 |
| B. breve | NK | 3975 | 101 | 1662 | 15 | 32 | 5 | 265 | 53 |
|  | NK + IL-2 | 1912 | 127 | 1988 | 22 | 35 | 9 | 72 | 57 |
|  | NK + IL-2 + anti-CD16 mAb | 4929 | 180 | 3934 | 29 | 55 | 28 | 153 | 72 |
| B. longum | NK | 9507 | 131 | 2325 | 32 | 38 | 9 | 80 | 74 |
|  | NK + IL-2 | 2195 | 135 | 2189 | 33 | 46 | 11 | 33 | 73 |
|  | NK + IL-2 + anti-CD16 mAb | 2906 | 158 | 1088 | 28 | 42 | 19 | 75 | 69 |
| L. acidophilus | NK | 6879 | 110 | 2553 | 16 | 77 | 5 | 400 | 63 |
|  | NK + IL-2 | 1116 | 127 | 2353 | 21 | 51 | 8 | 112 | 63 |
|  | NK + IL-2 + anti-CD16 mAb | 2004 | 199 | 3999 | 31 | 69 | 23 | 289 | 73 |
| L. bulgaricus | NK | 4501 | 121 | 3804 | 7 | 88 | 9 | 609 | 49 |
|  | NK + IL-2 | 1997 | 120 | 4737 | 15 | 78 | 10 | 313 | 55 |
|  | NK + IL-2 + anti-CD16 mAb | 1819 | 136 | 4062 | 6 | 72 | 8 | 305 | 50 |
| L. paracasei | NK | 3716 | 99 | 1069 | 4 | 53 | 8 | 506 | 40 |
|  | NK + IL-2 | 3983 | 157 | 6468 | 27 | 90 | 15 | 337 | 63 |
|  | NK + IL-2 + anti-CD16 mAb | 6385 | 215 | >22609 | 40 | 92 | 27 | 427 | 90 |
| L. plantarum | NK | 17756 | 122 | 22609 | 36 | 140 | 8 | 958 | 78 |
|  | NK + IL-2 | 3415 | 181 | 1923 | 36 | 115 | 14 | 427 | 73 |
|  | NK + IL-2 + anti-CD16 mAb | 3247 | 216 | 4147 | 40 | 92 | 20 | 335 | 78 |
| B. infantis | NK | 4265 | 123 | 2234 | 18 | 57 | 1 | 451 | 56 |
|  | NK + IL-2 | 5090 | 163 | 3225 | 19 | 113 | 19 | 382 | 72 |
|  | NK + IL-2 + anti-CD16 mAb | 3557 | 178 | 2646 | 32 | 88 | 22 | 360 | 65 |

Table 1. Production of cytokines, growth factors and chemokines by NK cells treated with bacterial strains Purified NK cells from healthy donors were left untreated or treated with IL-2 (1000 units/ml) or the combination of anti-CD16 mAb (3 μg/ml) and IL-2 (1000 units/ml) in the presence or absence of bacterial strains at 1:5 ratio (NK cell: bacteria) for 12-18 hours. Afterwards, the levels of cytokines, growth factors and chemokines were determined using Bio-Plex Pro Human Cytokine 27-plex Assay Kit.

NK Cell Supernatants Used for Stem Cell Differentiation

As described above, human NK cells were purified from PBMCs of healthy donors. NK cells were left untreated, treated with sAJ2 at 1:3 (NK:sAJ2), and/or a combination of anti-CD16 mAb (3 μg/mL) and IL-2 (1,000 U/mL) for 18 hours before supernatants were removed and used for differentiation experiments. The amounts of IFN-γ produced by activated NK cells were assess with IFN-γ ELISA (Biolegend, CA, USA). OSCSCs were differentiated with gradual daily addition of increasing amounts of NK cell supernatants (of corresponding treatments). On average, to induce differentiation, a total of 4,500 pg of IFN-γ containing supernatants, obtained from IL-2+ anti-CD16 mAb+sAJ2-treated NK cells, was added for 4 days to induce differentiation and resistance of OSCSCSs to NK cell-mediated cytotoxicity. Afterwards, target cells were washed with 1×PBS, detached and used for experiments.

Purification of Monocytes from the Peripheral Blood

Written informed consents, approved by UCLA Institutional Review Board (IRB) were obtained from healthy blood donors, and all procedures were approved by the UCLA-IRB. Peripheral blood was separated using Ficoll-Hypaque centrifugation, after which the white, cloudy layer, containing peripheral blood mononuclear cells (PBMC), was harvested, washed and re-suspended in RPMI 1640

(Invitrogen by Life Technologies, CA) supplemented with 10% FBS and plated on plastic tissue culture dishes. After 1-2 hours of incubation, the adherent subpopulation of PBMCs was detached from the tissue culture plates. Monocytes were purified using the EasySep® Human monocyte cell enrichment kit obtained from Stem Cell Technologies (Vancouver, BC, Canada). Based on flow cytometric analysis of CD14 the antibody-stained, enriched monocyte cells, the monocyte population was found to have greater than a 95% purify.

Generation of Osteoclasts (hOCs)

Osteoclasts were generated from PBMC-purified monocytes and cultured in alpha-MEM medium, containing M-CSF (25 ng/mL) and RANK Ligand (RANKL) (25 ng/mL), for 21 days. Medium was refreshed every 3 days with fresh alpha-MEM, containing M-CSF (25 ng/mL) and RANKL (25 ng/mL).

Analysis of Human OSCSCs Cell Growth in Immunodeficient and Humanized Mice

Animal research was performed under the written approval of the UCLA Animal Research Committee (ARC) in accordance to all federal, state, and local guidelines. Combined immunodeficient NOD.CB17-Prkdcscida and NOD.Cg-Prkdcscid Il2rgtm1Wjl/SzJ (NSG mice lacking T, B, and natural killer cells) were purchased from Jackson Laboratory and maintained in the animal facilities at UCLA in accordance with protocols approved by the UCLA animal research committee. Humanized-BLT (hu-BLT; human bone marrow/liver/thymus) mice were prepared on NSG background as previously described (Shimizu et al. (2010) Blood 115(8):1534-44; Vatakis et al. (2011) *Proc Natl Acad Sci USA*. 108(51):E1408-16).

Prior to tumor implantation, selected mice were fed $5 \times 10^9$ AJ2 bacteria (the combination of 8 probiotic strains listed above) every other day for one week. This adjuvant therapy was continued every other day until the day of sacrifice. For each mouse, lyophilized AJ2 was resuspended in 200 µL of fat free milk, and fed to them via pipetting.

In vivo growth of human oral squamous carcinoma stem cells (OSCSCs) was determined by orthotopic cell implantation of tumor cells into hu-BLT mice. To establish orthotopic tumors, mice were first anesthetized using an isoflurane set up, and OSCSCs were then transferred by direct injection of $1 \times 10^6$ cells mixed with 10 µl HC Matrigel (Corning, NY) into the oral cavity, to the floor of the mouth. Immediately prior to tumor cells injection, 5.0 mg/kg carprofen was injected subcutaneously, and this injection was repeated every 24 hours for 48 hours.

Following injection of tumor cells, all mice were continuously monitored for disease progression every other day. Mice were observed for overall signs of morbidity, such as loss of weight, ruffled fur, hunched posture, and immobility. Seven days after tumor implantation selected hu-BLT mice received $1.5 \times 10^6$ human expanded NK cells via tail vein (IV) injection.

Cell Dissociation and Cell Culture from Tissues of Tumor Bearing Hu-BLT and NSG Mice At the end of the experiment, mice were euthanized and oral tumor, liver, bone marrow, spleen and blood were obtained from hu-BLT or NSG mice. Single cell suspensions were obtained by digesting tissues using DMEM medium supplemented with collagenase II (1 mg/mL) (oral tumor) (Invitrogen, CA) and DNAse (10 u/mL) (Sigma-Aldrich, CA) and 1% BSA. The digested tissues were passed through 70 µM filters (Fisher Scientific, CA) to obtain single cell suspensions. Femurs and spleens were harvested from animals, and bone marrow cells and splenocytes were passed through 70 µM filters (Fisher Scientific, CA) to obtain single cell suspensions. Murine peripheral blood mononuclear cells (PBMCs) were obtained using Ficoll-Hypaque centrifugation of heparinized blood specimens. The white, cloudy layer, containing peripheral blood mononuclear cells (PBMCs), were harvested, washed and re-suspended in medium. Single cell suspensions of each tissue were cultured in the presence and/or absence of IL-2 (1000 units/mL) treatment, using RPMI 1640 media (Life Technologies, CA), supplemented with 10% FBS.

Purification of Human T Cells from Hu BLT Mice

CD3+ T cells from hu-BLT mice were positively selected from splenocytes using isolation kits from Stem Cell Technologies (Vancouver, BC, Canada). Cells were cultured at $1 \times 10^6$ cells/mL in RMPI 1640 media (Life Technologies, CA), supplemented with 10% FBS, along with IL-2 (1000 units/mL) treatment. Flow-through cells (negative for CD3, following the positive selection for T cells) were also cultured in the same manner.

Surface Staining $1 \times 10^5$ cells from each condition were stained in 100 µl of cold 1% PBS-BSA with pre-determined optimal concentration of PE conjugated antibodies, as detailed in the experiments, and incubated at 4° C. for 30 minutes. Then, cells were washed and resuspended in 1% PBS-BSA. The Epics C (Coulter) flow cytometer was used for cellular surface analysis.

$^{51}$Cr Release Cytotoxicity Assay $^{51}$Cr was purchased from Perkin Elmer (Santa Clara, CA). Standard $^{51}$Cr release cytotoxicity assays were used to determine NK cell cytotoxic function in the experimental cultures and the sensitivity of target cells to NK cell mediated lysis. The effector cells ($1 \times 10^5$ NK cells/well) were aliquoted into 96-well round-bottom microwell plates (Fisher Scientific, Pittsburgh, PA) and titrated at four to six serial dilutions. The target cells ($5 \times 10^5$ OSCSCs) were labeled with 50 µCi $^{51}$Cr (Perkin Elmer, Santa Clara, CA) and chromated for 1 hour. Following incubation, target cells were washed twice to remove excess unbound $^{51}$Cr. $^{51}$Cr-labeled target cells were aliquoted into the 96-well round bottom microwell plates containing effector cells at a concentration of $1 \times 10^4$ cells/well at a top effector:target (E:T) ratio of 5:1. Plates were centrifuged and incubated for a period of 4 hours. After a 4-hour incubation period, the supernatants were harvested from each sample and counted for released radioactivity using the gamma counter. Total (containing $^{51}$Cr-labeled target cells) and spontaneous (supernatants of target cells alone) release values were measured and used to calculate the percentage specific cytotoxicity. The percentage specific cytotoxicity was calculated using the following formula:

$$\% \text{ Cytotoxicity} = \frac{\text{Experimental cpm} - \text{spontaneous cpm}}{\text{Total cpm} - \text{spontaneous cpm}}$$

LU $30/10^6$ is calculated by using the inverse of the number of effector cells needed to lyse 30% of target cells×100.

Enzyme-Linked Immunosorbent Assays (ELISAs) and Multiplex Cytokine Assay

Human ELISA kits for IFN-γ and IL-10 were purchased from Biolegend (San Diego, CA). ELISA was performed to detect the level of IFN-γ and IL-10 produced from cell cultures. The assay was conducted as described in the manufacturer's protocol. Briefly, 96-well EIA/RIA plates were coated with diluted capture antibody corresponding to target cytokine and incubated overnight at 4° C. After 16-18 hours of incubation, the plates were washed 4 times with wash buffer (0.05% Tween in 1×PBS) and blocked with assay diluent (1% BSA in 1×PBS). The plates were incubated for 1 hour at room temperature, on a plate shaker at 200 rpm; plates were washed 4 times following incubation. Then, 100 µL of standards and samples collected from each culture were added to the wells and incubated for 2 hours at room temperature, on the plate shaker at 200 rpm. After incubation, plates were washed 4 times, loaded with detection antibody, and incubated for 1 hour at room temperature, on the plate shaker at 200 rpm. After 1 hour of incubation, the plates were washed 4 times; wells were loaded with Avidin-HRP solution and incubated for 30 minutes at room temperature, on the plate shaker at 200 rpm. After washing the plates 5 times with wash buffer; 100 µL of TMB substrate solution was added to the wells and plates were incubated in the dark until they developed a desired blue color (or up to 30 minutes). Then, 100 µL of stop solution (2N $H_2SO_4$) was added per well to stop the reaction. Finally, plates were read in a microplate reader, at 450 nm to obtain absorbance values (Biolegend, ELISA manual).

The levels of cytokines and chemokines were examined by multiplex assay, which was conducted as described in the manufacturer's protocol for each specified kit. Analysis was performed using a Luminex multiplex instrument (MAG-PIX, Millipore, Billerica, MA) and data was analyzed using the proprietary software (xPONENT 4.2, Millipore, Billerica, MA).

Statistical Analysis

An unpaired, two-tailed student t-test was performed for the statistical analysis of two groups. One-way ANOVA with a Bonferroni post-test was used to compare more than two groups.

Humanized Mouse Model

Varying levels of NK cell impairment and/or deletion in nude, NOD-scid and NSG strains could explain discrepancies in the ability of CSCs to give rise to human tumors in these different immunodeficient strains. Many questions have been raised, based on previous studies performed on immunodeficient animals, regarding specific immune subsets and their roles in controlling cancer initiation, growth, and metastasis. Since it is difficult to assess and compare the aggressiveness and metastatic potential of primitive CSCs using immunodeficient mouse strains, humanized mice, with restored human immune systems, offer the most suitable platform to implant such tumors.

There have been numerous attempts to generate mice that bear a fully reconstituted human immune system. There are also differences between human immune system reconstitution levels supported by specific mouse strains. Since it is critical for the background strain to harbor severe immunodeficiency, NSG or NRG mice have typically been the strain of choice. There are many methods in creating various humanized mouse models, with differences in the age of mice, transplanted cell type, source or donor cell type, injection/implantation method, irradiation, etc. Of these variations, the simplest humanization method consists of injecting immunodeficient mice with human PBMCs, obtained from adult healthy donors/patients. PBMCs circulate in the blood, either dying or migrating to other tissues; the downside is that these mice can only be used. for short term experiments, since circulating mature immune cells in mice initiate graft versus host disease (GvHD) against murine recipients.

Another method uses isolated $CD34^+$ progenitor cells originating from the peripheral blood, cord blood or fetal liver. $CD34^+$ cells are injected into either newly born or adult NSG mice. They stably engraft into the bone marrow and are capable of differentiating into all hematopoietic lineages of the human immune system. The CD34+ humanized mouse model's major limitation is that it lacks the presence of a human thymus, so instead, T cells undergo selection in the context of the mouse MHC.

The BLT humanized mouse (hu-BLT) represents the most advanced and complete humanized mouse model generated, to date. The human immune engraftment protocol consists of surgically implanting pieces of human fetal liver and thymus tissue under the renal capsule of NSG mice, followed by tail vein IV injection of same-donor $CD34^+$ hematopoietic cells to support full reconstitution of the human bone marrow. Thus, positive and negative selection of developing T cells occurs in the presence of human thymus. Consequently, immature T cells become functional $CD4^+$ helper and $CD8^+$ cytotoxic T cells after human MHC class I and II restriction. Hu-BLT model is the only known humanized mouse model to displays mucosal immunity. Hematopoietic stem cells (HSCs) develop, at least to some extent, into human T cells, B cells, NK cells, monocytes, myeloid derived suppressor cells (MDSCs), macrophages; dendritic cells, erythrocytes, and platelets in the BLT's tissues. Long-term peripheral reconstitution of human $CD45^+$ immune cells is usually within the 30-80% range, as detected in the blood, spleen and bone marrow (manuscript in preparation). Human immune cells have been detected in the reproductive tract of females, intestines and rectum, as well as the gingiva (manuscript in prep). It is also worth noting that NSG-BLT mice (BLT mice developed from NSG background strain) exhibit substantially higher levels of human leukocyte reconstitution in their peripheral blood than NOD-scid-BLT mice. These features demonstrate that hu-BLT, developed from NSG background, is arguably the best available model for studying human immunity, thus far.

Example 2: Probiotic Bacteria Activates NK Cells

Probiotic Bacteria Induce Cytokine Secretion but have No Effect on Cytotoxicity

Figure 1:
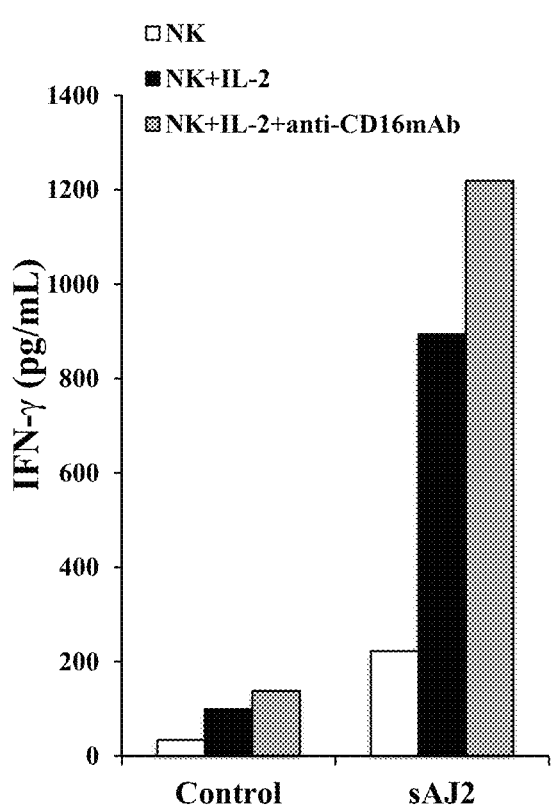
FIG. 1 includes 2 panels, identified as panels A and B, which show that treatment of NK cells with probiotic bacteria induces higher secretion of IFN-γ and anti-inflammatory cytokine, IL-10. Purified NK cells ($1 \times 10^6$/mL) were left untreated, treated with IL-2 (1000 units/mL), or anti-CD16 mAb (3 µg/mL) and IL-2 (1000 units/mL), with or without probiotic bacteria, sAJ2, at a 1:5 (NK cell:bacteria) ratio, for 18 hours. Supernatants of cultures were harvested and used for multiplex array analysis. Above are the levels of secretion for IFN-γ (FIG. 1A) and IL-10 (FIG. 1B).
Figure 1:
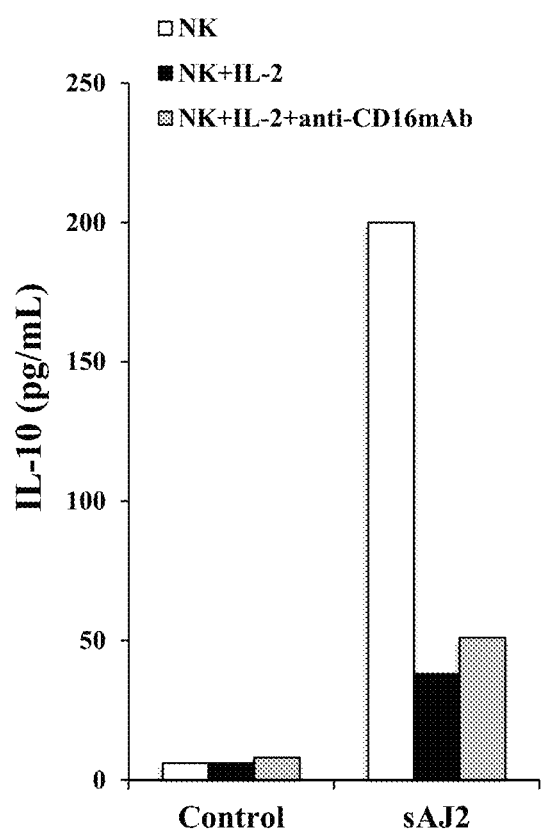

To investigate the effect of probiotics on NK cell function, NK cells were cultured either with or without sAJ2 under different activation conditions. NK cells, left as control or activated with IL-2 or IL-2+anti-CD16 mAb, induced higher levels of IFN-γ and IL-10 after treatment with sAJ2 probiotic (FIG. 1). Although activated NK cells secreted IFN-γ, treatment of activated NK cells with sAJ2 bacteria further significantly increased the levels of IFN-γ (FIG. 1A). Treatment with sAJ2 induced secretion of IL-10 in all NK conditions, especially for control NK cells (not activated) (FIG. 1B).

Figure 2:
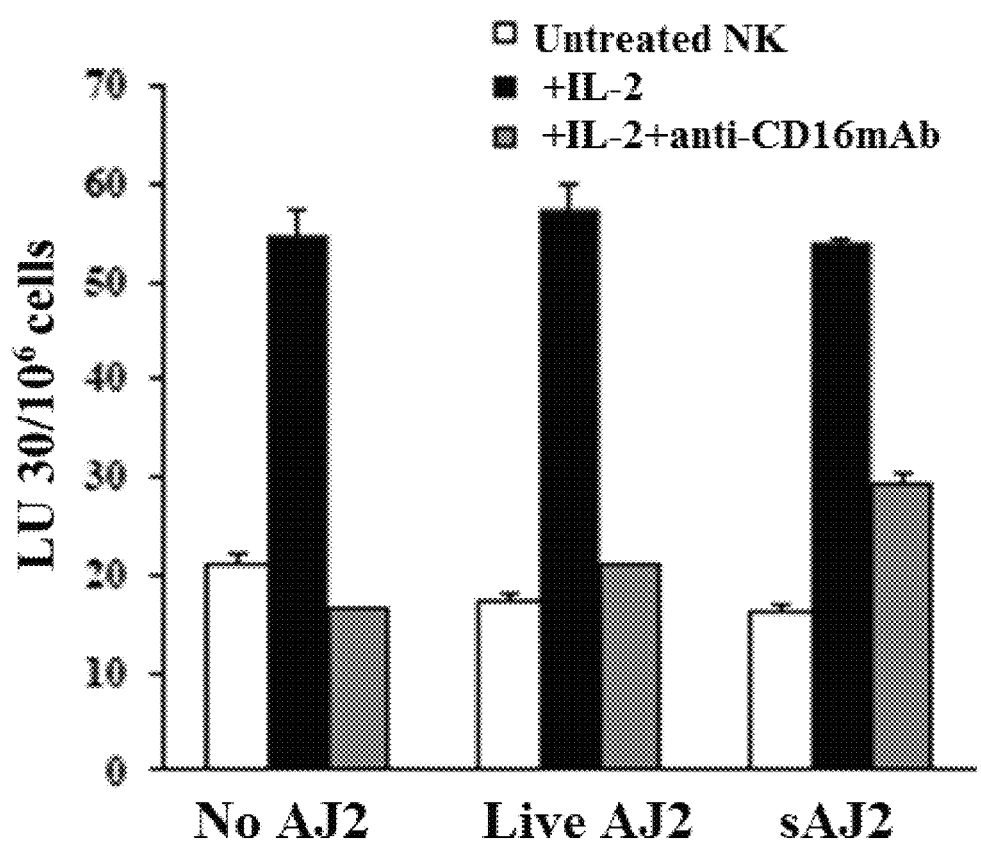
FIG. 2 shows that probiotic bacteria do not affect NK cell-mediated cytotoxicity against Human oral squamous carcinoma stem cells (OSCSCs). Purified NK cells ($1 \times 10^6$/mL) were left untreated, IL-2 (1000 units/mL) treated, or anti CD16 mAb (3 µg/mL) and IL-2 (1000 units/mL) treated, and cultured in the presence or absence of live or sonicated AJ2 at a 1:3 (NK cell:bacteria) ratio, for 12-18 hours. Following overnight incubation, they were added to $^{51}$Cr labeled OSCSC cells (target cells). NK cell cytotoxicity was determined by conducting a standard 4-hour $^{51}$Cr release assay. A gamma counter was used to measure the radioactivity released into the supernatants. Levels of NK cell-mediated cytotoxicity against radioactively labeled OSCSCs were determined using lytic units (LU 30/$10^6$).

Although sAJ2 bacteria induced cytokine secretion function in NK cells, they had no effect on their cytotoxic function (FIG. 2). NK cells, untreated as well as activated, exhibited no significant change in their ability to target and lyse OSCSCs when treated with either live or sonicated AJ2 bacteria (FIG. 2). Thus, sAJ2 bacteria enhance the functional effect of NK cells through cytokine secretion, while NK cells also maintain the same level of cytotoxicity.

Figure 3:
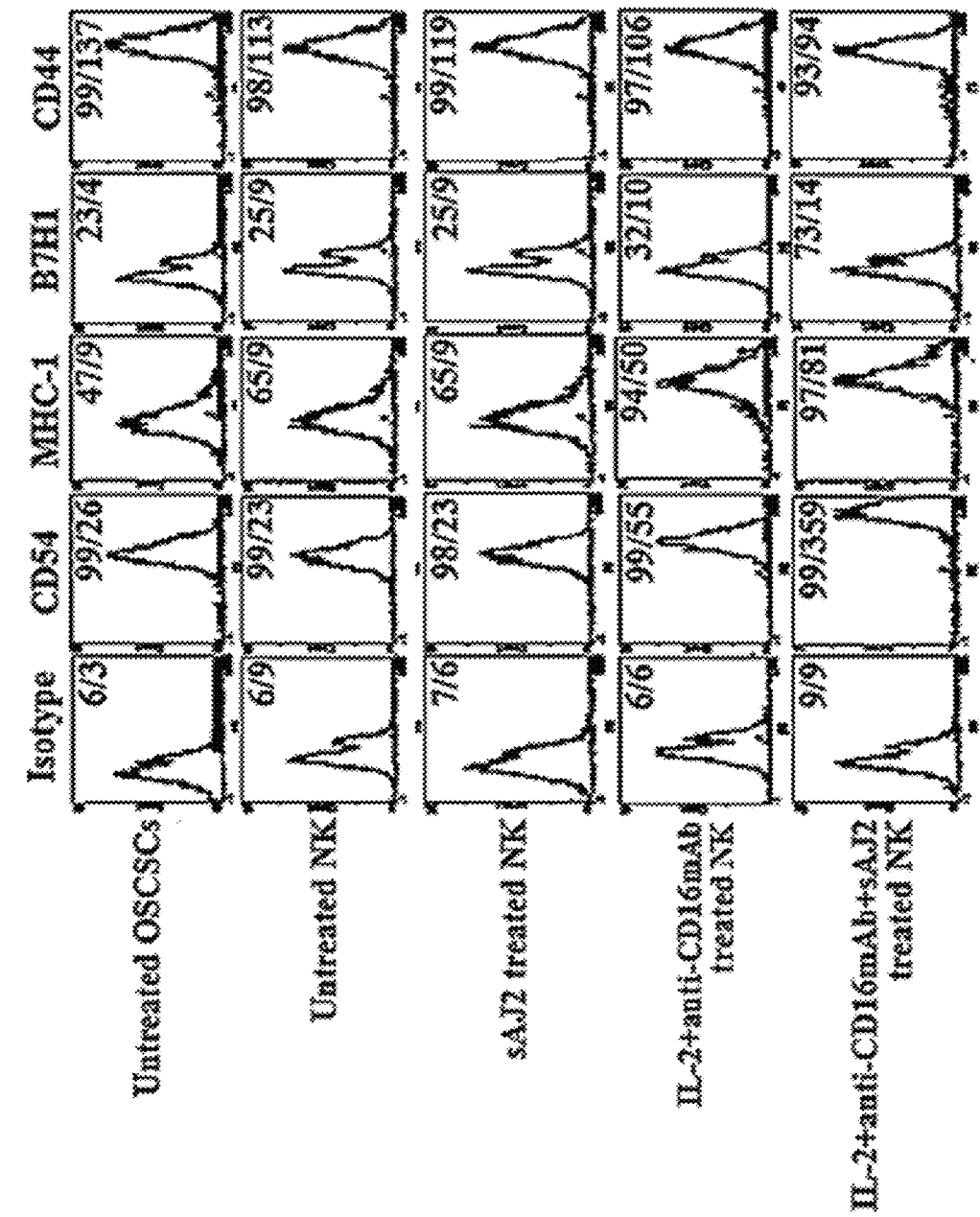
FIG. 3 shows that surface expression trend demonstrates upregulation of differentiation markers in OSCSCs differentiated with IL-2+ anti-CD16 mAb+sAJ2 activated NK cells. Purified NK cells were left untreated or treated with anti-CD16 mAb (3 µg/mL) and IL-2 (1000 units/mL), with or without sonicated AJ2 (sAJ2) at a 1:3 (NK cell:bacteria) ratio, for 18 hours. Afterwards, the supernatants from each NK sample were harvested and used to treat/differentiate OSCSCs for 4 days. OSCSCs were detached from the tissue culture plates and $5 \times 10^4$ cells from each treatment were used to measure surface expression of surface markers via flow cytometry. PE conjugated antibodies against isotype control, CD54, MHC-I, B7H1 and CD44 were used to stain untreated OSCSCs or those treated with NK cell supernatants, as detailed in the figure. Isotype control antibodies were used as controls. The numbers on the right hand corner are the percentages and the mean channel fluorescence intensities for each histogram.

Supernatants of sAJ2 Bacteria-Treated, Split Anergized NK Cells Induced Differentiation and Resistance of OSCSCs to NK Cell-Mediated Cytotoxicity To investigate the differentiation capability of split anergized NK cells (NK cells activated with anti-CD16 mAb and IL-2) treated with sAJ2, NK cells were activated and treated as described in FIG. 3, and supernatants were collected and used to treat stem-like tumor cells, OSCSCs, as described in the Materials and Methods section. Following differentiation, surface expression of key cell surface markers was studied. MHC-I, CD54 and B7H1 were found to be upregulated on the surface of OSCSCs differentiated with supernatants from split anergized NK cells, both alone and in combination with sAJ2, although treatment with sAJ2 in combination significantly increased their levels of expression (FIG. 3). There was also a moderate decrease in the expression of CD44 stem cell marker for OSCSCs differentiated with split anergized NK supernatants, both alone and in combination with sAJ2. Supernatants from NK cells treated with sAJ2 alone were not effective in differentiating OSCSCs (FIG. 3).

Figure 4:
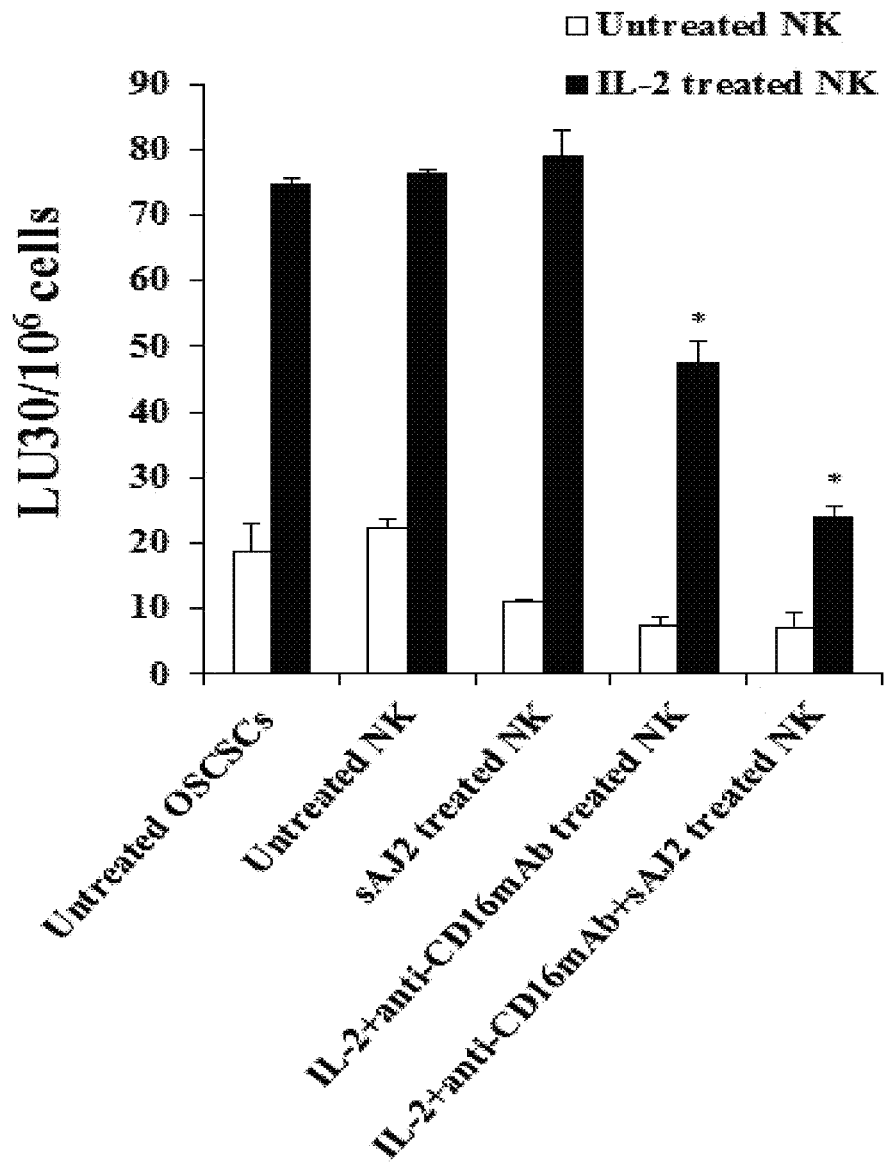
FIG. 4 shows that OSCSCs treated with supernatants of split anergized NK cells were significantly more resistant to NK cell-mediated cytotoxicity—highest level of resistance in those treated with supernatants of split anergized NK cells in combination with sAJ2. Purified NK cells were treated as described in FIG. 3. Afterwards, the supernatants from each NK sample were harvested and used to treat/differentiate OSCSCs for 4 days. OSCSCs were detached from the tissue culture plates and their sensitivity to NK cell-mediated lysis was evaluated using a standard 4-hour $^{51}$Cr release assay. Levels of NK cell-mediated cytotoxicity against radioactively labeled OSCSCs conditions were determined using lytic units (LU 30/10$^6$).

Also, following differentiation with supernatants, the various conditions of OSCSCs were assayed for their susceptibility to NK cell-mediated lysis using $^{51}Cr$ release assay (FIG. 4). OSCSCs treated with supernatants obtained from untreated or sAJ2 alone treated NK cells showed no change in their susceptibility to NK cell-mediated lysis. On the other hand, treatment of OSCSCs with supernatants from NK cells treated with IL-2+anti-CD16 mAb resulted in tumor resistance to NK cell-mediated lysis. OSCSCs showed significantly more resistance to IL-2 activated NK cell-mediated lysis following treatment with supernatants from IL-2+anti-CD16 mAb+sAJ2 activated NK cells compared to the controls, including the split anergized control ($P<0.05$) (FIG. 4).

Differentiation Induced by Split Anergized NK Cells was Significantly Mediated Via Cytokine Secretion of IFN-γ and TNF-α

Figure 5:
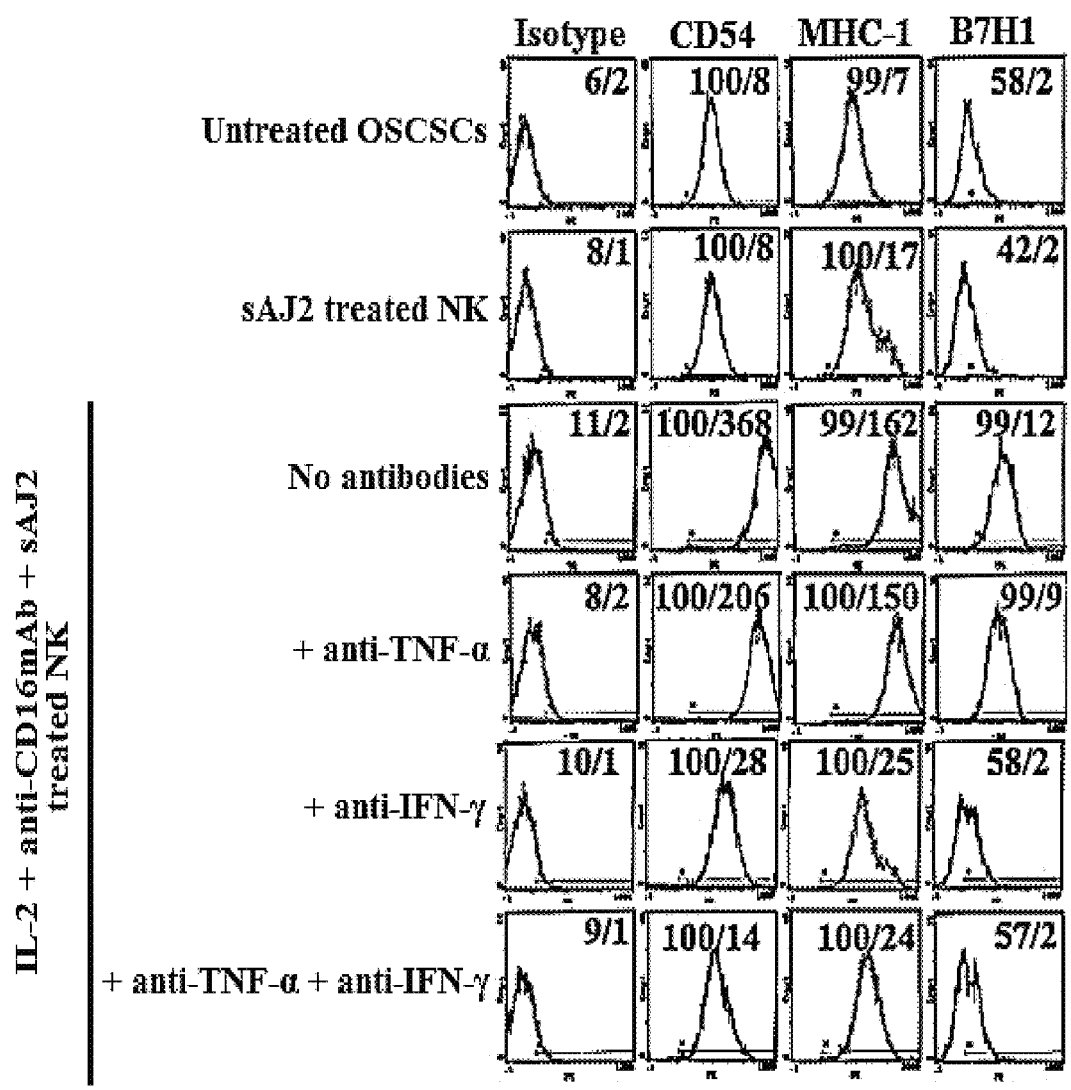
FIG. 5 shows that induction of differentiation of OSCSCs treated with IL-2+ anti-CD16 mAb+sAJ2 NK cell supernatant is mediated by the combination of IFN-γ and TNF-α secreted by NK cells. Purified NK cells (1×10$^6$/mL) were treated with sAJ2 alone at a 1:3 (NK cell:bacteria) ratio, or in combination with IL-2 (1000 units/mL) and anti-CD16 mAb (3 μg/mL), for 18 hours. Afterwards, the supernatants from each NK sample were harvested and used to treat/differentiate OSCSCs for 4 days. Anti-IFN-γ (1:100) and anti-TNF-α (1:100) antibodies were added to OSCSCs before the start of NK sup treatments. OSCSCs were detached from the tissue culture plates, and 5×10$^4$ cells from each treatment were used to measure surface expression of surface markers via flow cytometry. PE conjugated antibodies against isotype control, CD54, MHC-I, and B7H1 were used to stain untreated OSCSCs or those treated with NK cell supernatants (with or without antibodies against IFN-γ and/or anti-TNF-α), as detailed in the figure. Isotype control antibodies were used as controls. The numbers on the right hand corner are the percentages and the mean channel fluorescence intensities for each histogram.

To understand the mechanism through which OSCSCs differentiate and become resistant to NK cell-mediated lysis, OSCSCs were treated with supernatants obtained from NK cells treated with IL-2+anti-CD16 mAb+sAJ2, as well as antibodies against IFN-γ and/or TNF-α. As described earlier, supernatants from NK cells treated with IL-2+anti-CD16 mAb+sAJ2 induced differentiation and resistance of tumors to NK cell-mediated cytotoxicity (FIGS. 3-6). Anti-IFN-γ treatment alone prevented the surface expression modulation of CD54, MHC-I and B7H1 on differentiated OSCSCs, while anti-TNF-α only prevented CD54 surface expression upregulation. Meanwhile, OSCSCs supplemented with supernatants from NK cells treated with IL-2+anti-CD16 mAb+sAJ2 with the combination of anti-IFN-γ and anti-TNF-α showed inhibition of surface expression modulation to the supplementation (FIG. 5).

Figure 6:
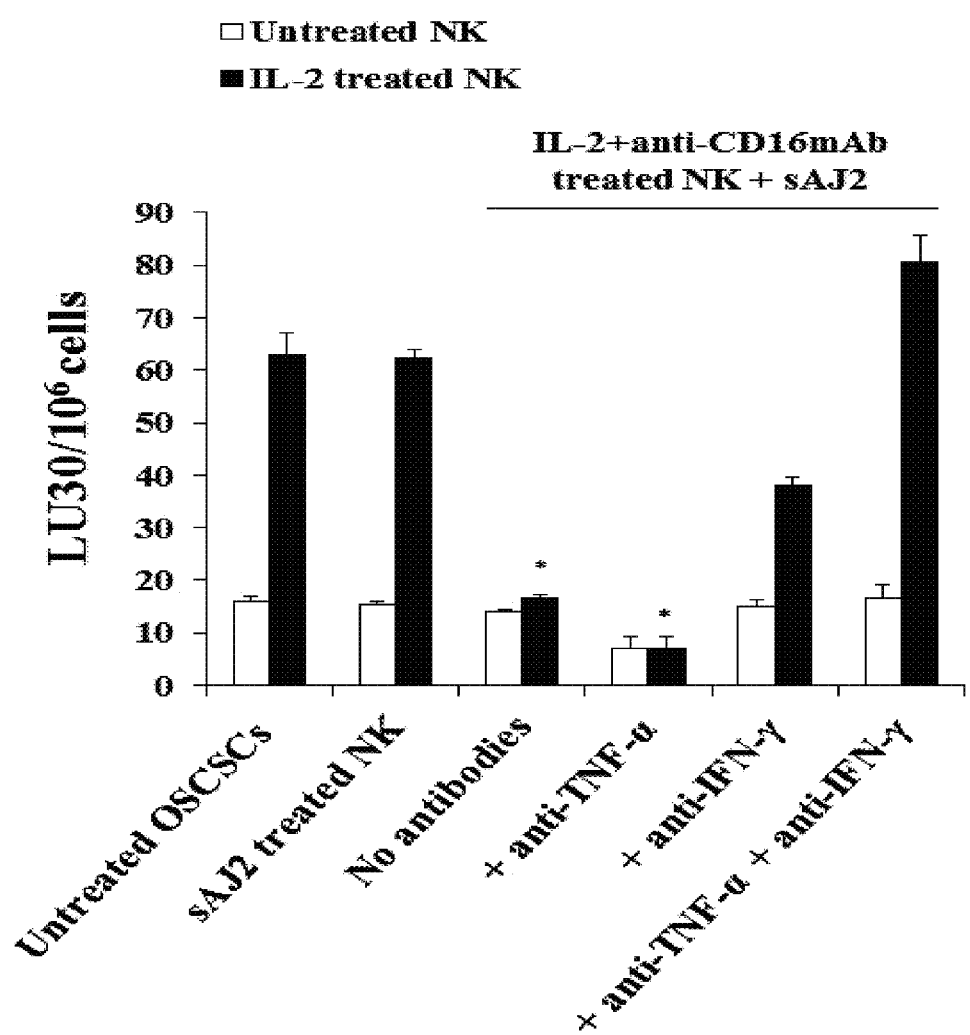
FIG. 6 shows that induction of differentiation, and therefore, resistance to NK cell mediated lysis of OSCSCs treated with IL-2+ anti-CD16 mAb+sAJ2 NK cell supernatant is mediated by the combination of IFN-γ and TNF-α secreted by NK cells. Purified NK cells were treated as described in FIG. 5. Afterwards, supernatants from each NK sample were harvested and used to treat/differentiate OSCSCs for 4 days. Anti-IFN-γ (1:100) and anti-TNF-α (1:100) antibodies were added to OSCSCs before the start of NK sup treatments. OSCSCs were then detached from the tissue culture plates and their sensitivity to NK cell-mediated lysis was evaluated using a standard 4-hour $^{51}$Cr release assay. Levels of NK cell-mediated cytotoxicity against radioactively labeled OSCSCs conditions were determined using lytic units (LU 30/10$^6$).
Figure 7:
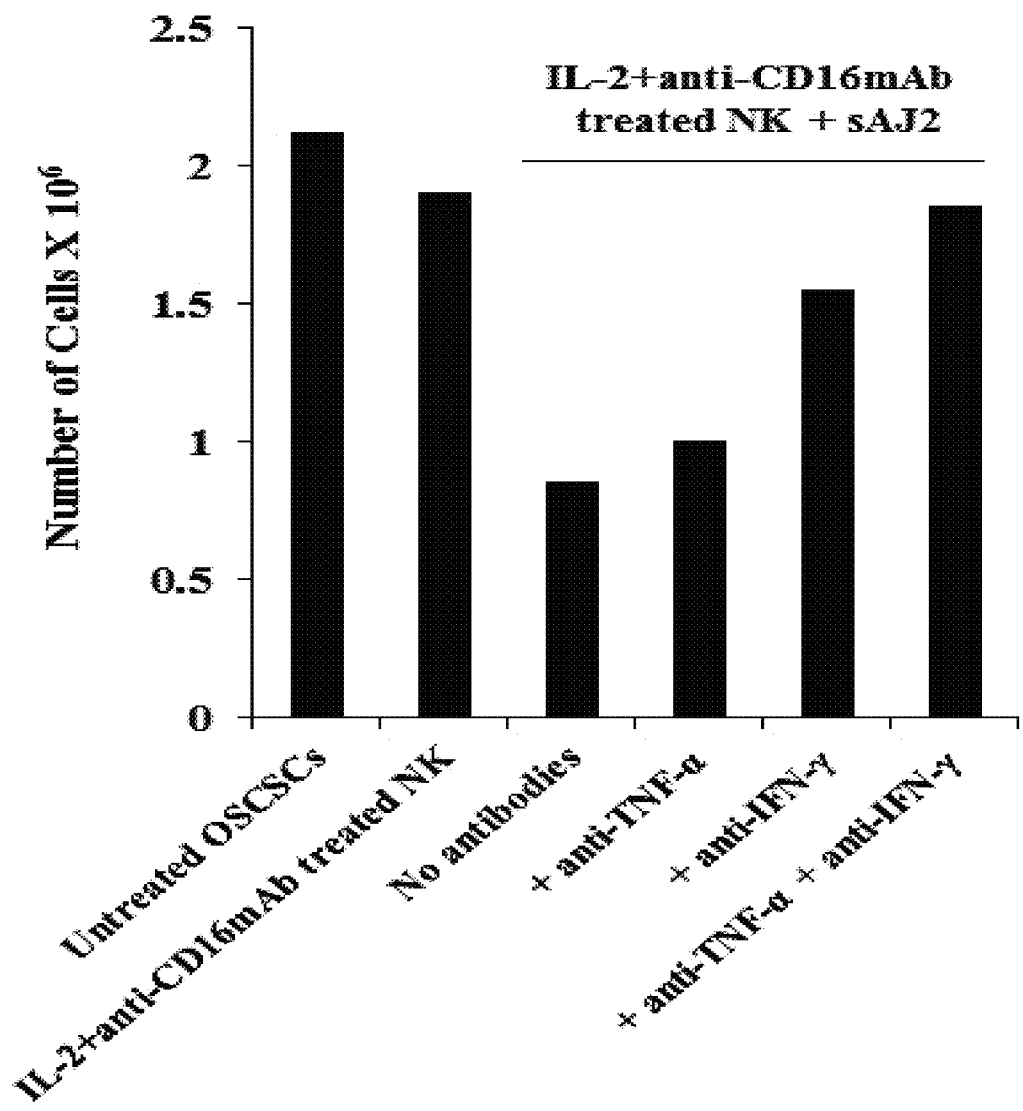
FIG. 7 shows that induction of differentiation, also resulting in growth inhibition of OSCSCs treated with IL-2+ anti-CD16 mAb+sAJ2 NK cell supernatant, is mediated by the combination of IFN-γ and TNF-α secreted by NK cells. Purified NK cells were treated as described in FIG. 5. Afterwards, supernatants from each NK sample were harvested and used to treat/differentiate OSCSCs for 4 days. Anti-IFN-γ (1:100) and anti-TNF-α (1:100) antibodies were added to OSCSCs before the start of NK sup treatments. OSCSCs were then detached from the tissue culture plates and cells were counted via microscopy.

When either anti-TNF-α or anti-IFN-γ were added to supernatant-treated cells, there was either no or a moderate inhibitory effect on the resistance of OSCSCs to NK cell-mediate lysis (FIG. 6). On the other hand, when both antibodies were used together, OSCSCs maintained their sensitivity to NK cell-mediated lysis (FIG. 6). Additionally, differentiation of OSCSCs with IL-2+anti-CD16 mAb+sAJ2 activated NK cell supernatants resulted in tumor growth inhibition, in comparison to untreated or split anergized NK supernatant treated OSCSCs (FIG. 7). When a combination of anti-IFN-γ and anti-TNF-α were used in along with the supernatants from IL-2+anti-CD16 mAb+sAJ2 activated NK cells, tumor growth was restored to levels seen in untreated OSCSCs (FIG. 7).

Figure 8:
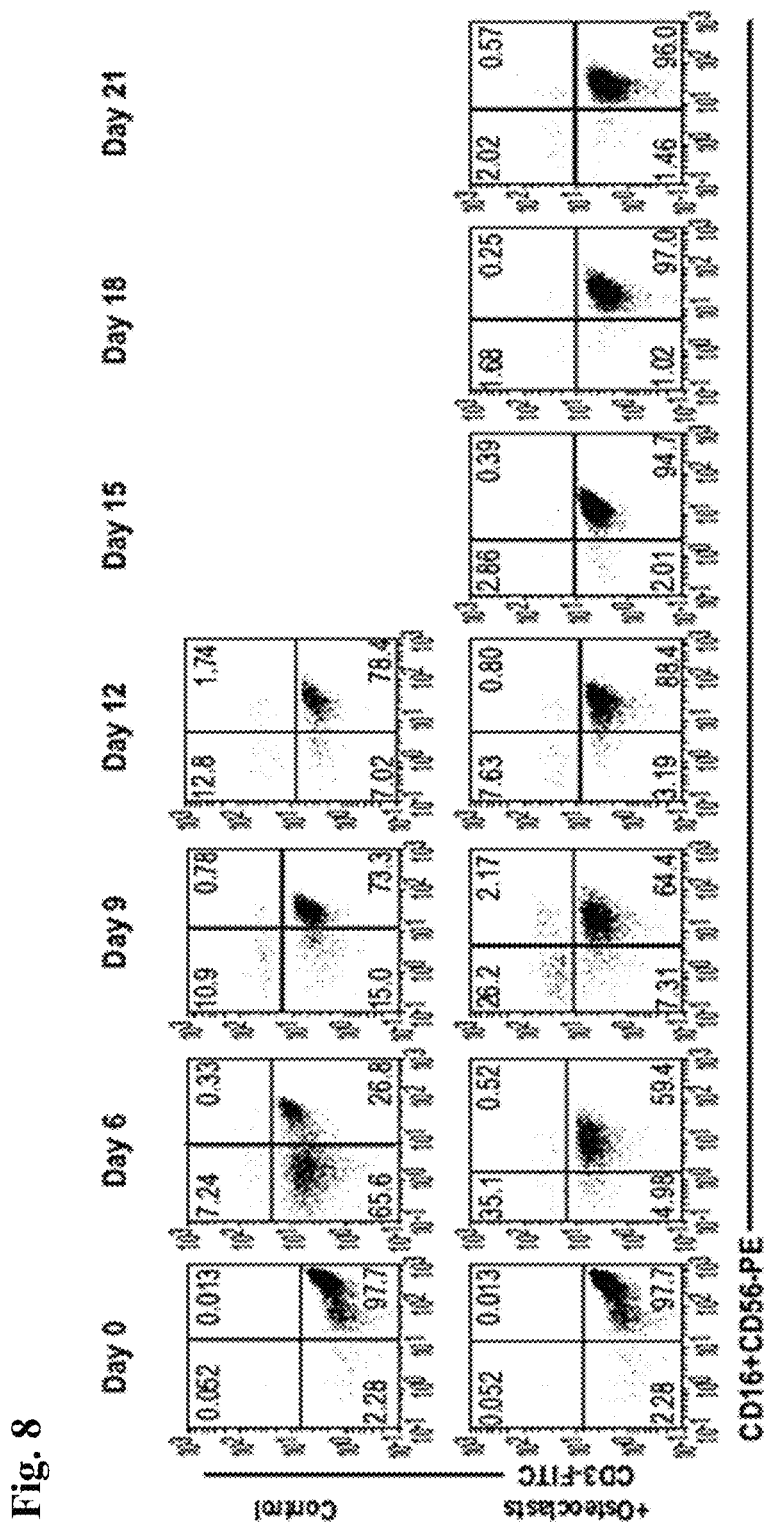
FIG. 8 shows that sAJ2 in combination with osteoclasts expand NK cells, and not T cells, maintaining them for a longer period of time. Purified NK cells and monocytes were obtained from PBMCs of healthy donors, as described in the Materials and Methods section. To generate osteoclasts, monocytes were cultured in alpha-MEM media containing M-CSF (25 ng/mL) and RANKL (25 ng/mL), for 21 days, replenishing media every 3 days. Then purified NK cells (1×10$^6$ cells/mL) were treated with the combination of IL-2 (1000 units/mL) and anti-CD16 mAb (3 μg/mL) for 18 hours before they were co-cultured with sAJ2, with or without autologous osteoclasts at a 1:2:4 (OC:NK:sAJ2) ratio. Culture medium of expanding NK cells was refreshed and re-supplemented with IL-2 (1000 units/mL) at respective days detailed in the figure. Surface expression levels of CD3, CD16, and CD56 were analyzed on respective days, using flow cytometry.

Example 3: Osteoclasts and Monocytes Expanded NK Cells in Combination with Probiotic Bacteria sAJ2 in Combination with Osteoclasts Expanded NK Cells, and not T Cells, Maintaining them for a Longer Period of Time NK cells were isolated from healthy donor PBMCs, and NK purity was determined using CD3 and CD16/CD56 antibodies before cultures were conducted. NK cells were then activated with anti-CD16 mAb and IL-2 18-20 hours before co-culturing them with sAJ2 alone ("Control") or sAJ2 in combination with osteoclasts ("+Osteoclasts") (FIG. 8). NK cells treated with sAJ2 failed to expand and maintain NK cell purity over time, whereas NK cells cultured with sAJ2 and osteoclasts maintained NK purity and expansion for a long period of time. The combination of OCs and sAJ2 preferentially expanded NK cells while maintaining a low proportion of T cells throughout the cultures (FIG. 8).

Figure 9:
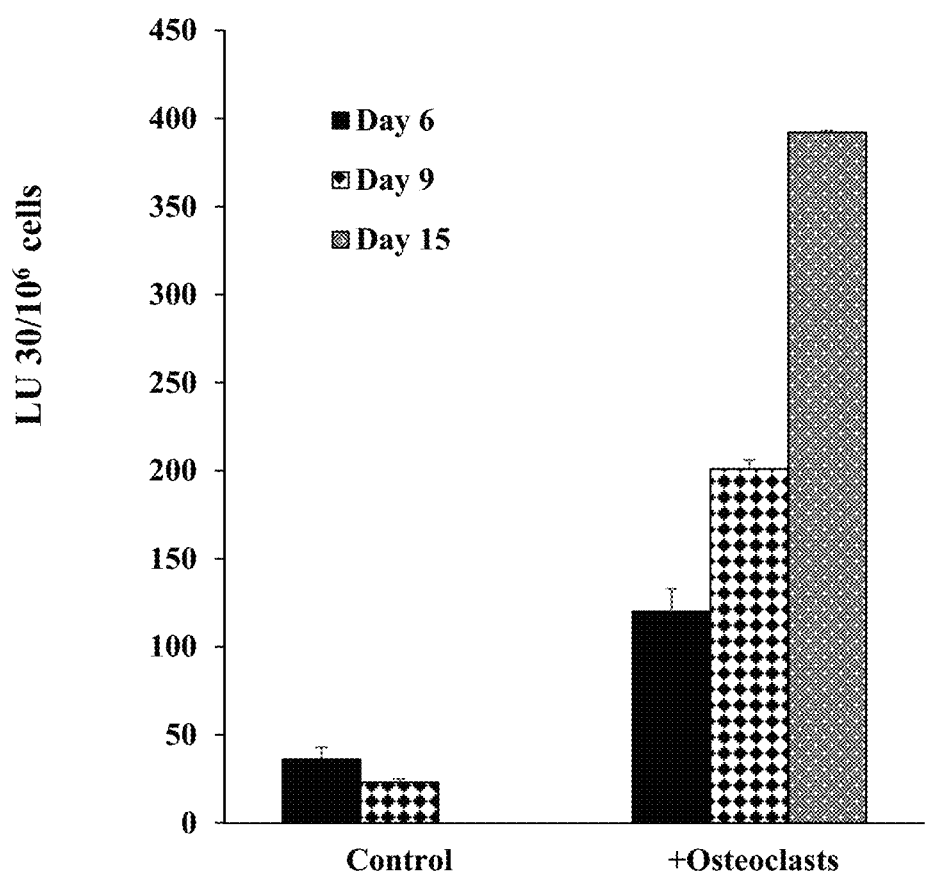
FIG. 9 shows that NK cells expanded with osteoclasts as feeder cells are highly cytotoxic for an extended length of time. Purified NK cells and monocytes from PBMCs were cultured and treated as described in FIG. 8. At days 6, 9 and 15, NK cell-mediated cytotoxic function of these expanded NK cells were measured using a standard 4-hour $^{51}$Cr release assay. Levels of NK cell-mediated cytotoxicity of these NK cell conditions, against radioactively labeled OSCSCs (target cells) were determined using lytic units (LU 30/10$^6$).
Figure 10:
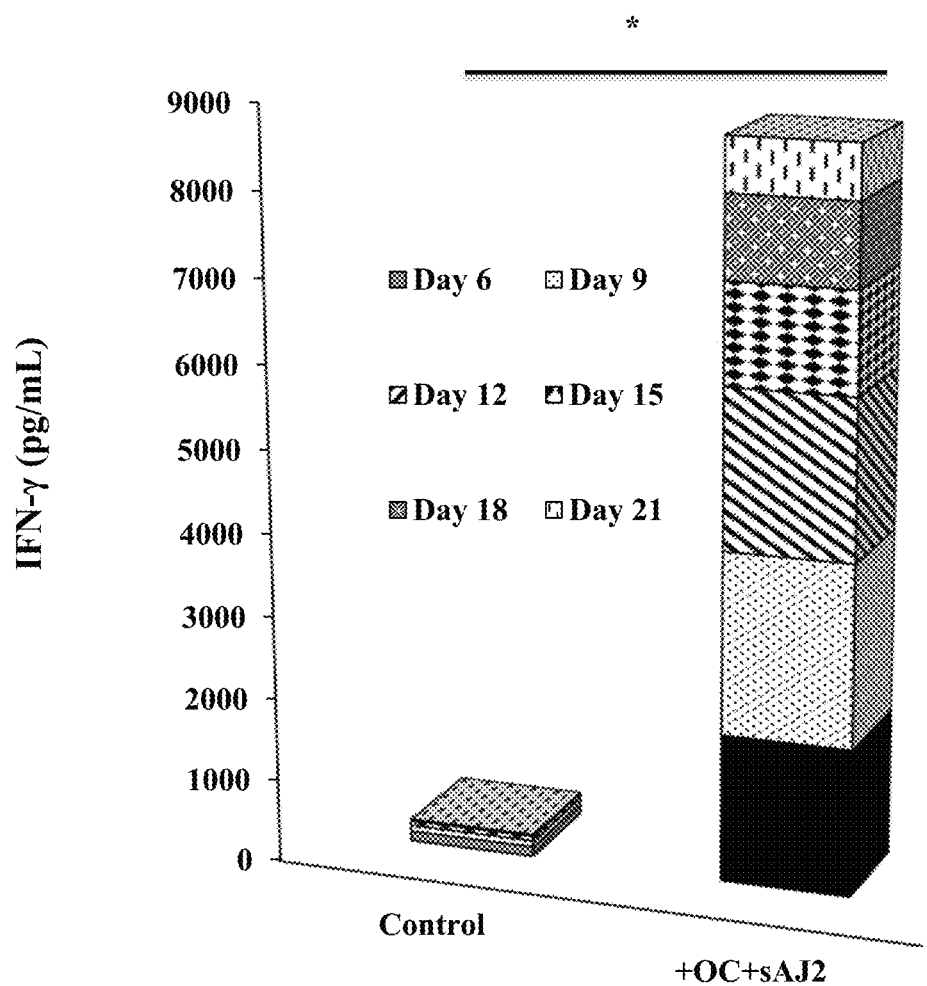
FIG. 10 shows that Osteoclast-expanded NK cells secrete significantly higher levels of cytokines for an extended period of time. Purified NK cells and monocytes from PBMCs were cultured and treated as described in FIG. 8. Purified NK cells (1×10$^6$ cells/mL) were treated with the combination of IL-2 (1000 units/mL) and anti-CD16 mAb (3 μg/mL) for 18 hours before they were co-cultured with sAJ2, with or without autologous osteoclasts at a 1:2:4 (OC:NK:sAJ2) ratio. On days 6, 9, 12, 15, 18, and 21, supernatants of expanding NK cells were harvested and levels of IFN-γ were measured using human IFN-γ ELISA. Cells were replenished with fresh culture medium and re-supplemented with IL-2 (1000 units/mL) at respective days detailed in the figure.
Figure 11:
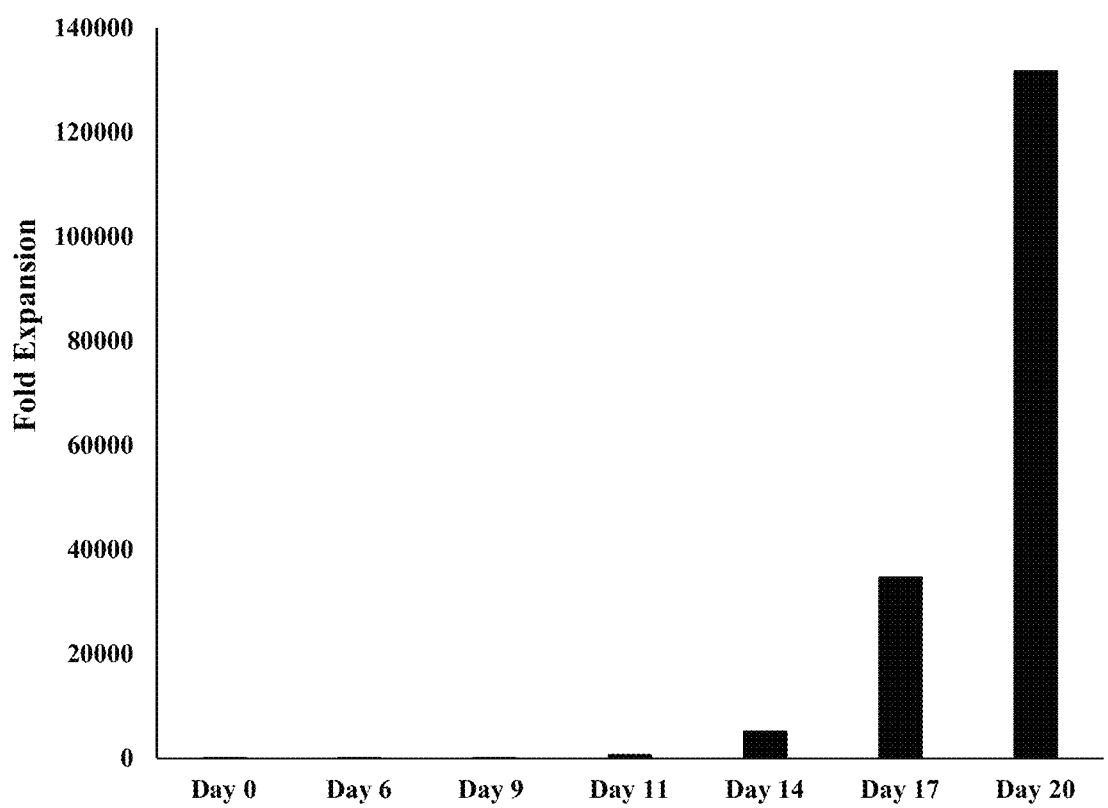
FIG. 11 shows fold expansion of osteoclast-expanded NK cells. Highly purified NK cells and monocytes were obtained from PBMCs of healthy donors. To generate osteoclasts, monocytes were cultured in alpha-MEM media containing M-CSF (25 ng/mL) and RANKL (25 ng/mL) for 21 days. For expansion, purified NK cells (1×10$^6$ cells/mL) were treated with the combination of IL-2 (1000 units/mL) and anti-CD16 mAb (3 μg/mL) for 18 hours; then they were co-cultured with autologous osteoclasts in the presence of sAJ2 at a 1:2:4 (OC:NK:sAJ2) ratio. Culture medium of expanding NK cells was refreshed and re-supplemented with IL-2 (1000 units/mL) at respective days detailed in the figure. Fold expansion was determined based on manual cell counts, via microscopy.

Expanded NK Cells were Highly Functional, Both in Terms of Cytotoxicity and Cytokine Secretion Functions To investigate the functional ability of sAJ2 and osteoclast-expanded NK cells, cell mediated cytotoxicity and IFN-γ secretion levels were measured. NK cells activated with anti-CD16 mAb and IL-2, as described previously, co-cultured with sAJ2 and osteoclasts lysed significantly more OSCSCs than NK cells co-cultured with sAJ2 alone; and there was a significant increase in cytotoxicity of expanded NK cells from day 9 to day 15 (FIG. 9), correlating with higher expansion of NK cells in co-culture with sAJ2 and osteoclasts after day 14 (FIG. 11). IL-2 and anti-CD16 mAb activated NK cells cultured with sAJ2 and osteoclasts secreted significantly higher amounts of IFN-γ, compared to NK cells activated with IL-2 and anti-CD16 mAb, co-cultured with sAJ2 alone (FIG. 10).

sAJ2 in Combination with Osteoclasts Maintained a High Level of NK Expansion for an Extended Time Period To investigate the expansion rate of expanded NK cells (activated with anti-CD16 mAb and IL-2 overnight, and co-cultured with sAJ2 and osteoclasts), cells were counted via microscopy at various time points (FIG. 11). Upon analysis of NK cell expansion rate and population doubling (defined by the log of the ratio of the final count to the baseline count divided by the log of 2) it was found that NK cells expanded 21,000-132,000 fold at day 20 and 0.3-5.1 million fold on day 31, with 17-21 population doublings within 4 weeks (Table 2).

TABLE 2

| NK expansion methodologies | | |
|---|---|---|
| NK Source | Feeder cells | Expansion |
| Negative selection for NKs from PBMCs | Autologous and allogeneic osteoclasts | 21,000-132,000 fold expansion at 20 days, 0.3-5.1 million at 31 days; 17-21 population doublings (avg. 19) at 4 weeks |
| Whole PBMCs or purified NKs | Irradiated PBMCs, Wilms tumor cell line, K562-mb15-EBV-TM-LCL, or none | 4-5, 712 fold at 14-21 days |
| Whole PBMCs used initially, residual T-cells removed after 7 days (anti-CD3 Dynabeads), genetically modified with TERT for immortalization | K562-mb15-41BBL (continued stimulation) | TERT transformed: (130-227 population doublings over 1000 days) Non-transformed: (11-20 population doublings at 8-15 weeks) |
| Cord Blood (CB), CD34+ selection | None | 2,000-15,000 fold at 5 weeks |
| NK-92 (cell line) | None | 218-250 fold at 15-17 days |

This table summarizes methods detailed in the art or unpublished research work by Applicants (e.g., for those NKs negatively selected from PBMCs) describing various NK expansion protocols, including source of NK cells, feeder cells used (if applicable), as well as the expansion success obtained (including the number of days required to achieve such expansion).

Monocytes and Osteoclasts from NK Injected Tumor-Bearing Mice had Greater Ability to Activate NK Cells when Compared to Those from Tumor-Bearing Mice in the Absence of NK Injection NK cells from NK injected tumor-bearing mice and NK supernatant-differentiated tumor-bearing mice when cultured with autologous monocytes had significantly augmented cytotoxicity and IFN-γ secretion when compared to those implanted with undifferentiated tumors in the absence of NK cell injection. Blocking NK-mediated differentiation of tumors through the addition of antibodies to TNF-α and IFN-γ before implantation decreased cytotoxicity and IFN-γ secretion. Osteoclasts were generated from BM-derived monocytes of hu-BLT mice and cultured with allogeneic NK cells from healthy human donors to study the extent of NK cells expansion. As a result, NK cells expansion and IFN-γ secretion were augmented in NK-injected tumor-bearing mice or NK supernatant-differentiated tumor-bearing mice, compared to those obtained from tumor-bearing mice without NK injection. Thus monocytes and osteoclasts from NK injected tumor-bearing mice had greater ability to activate NK cells than those from tumor-bearing mice in the absence of NK injection.

Figure 12:
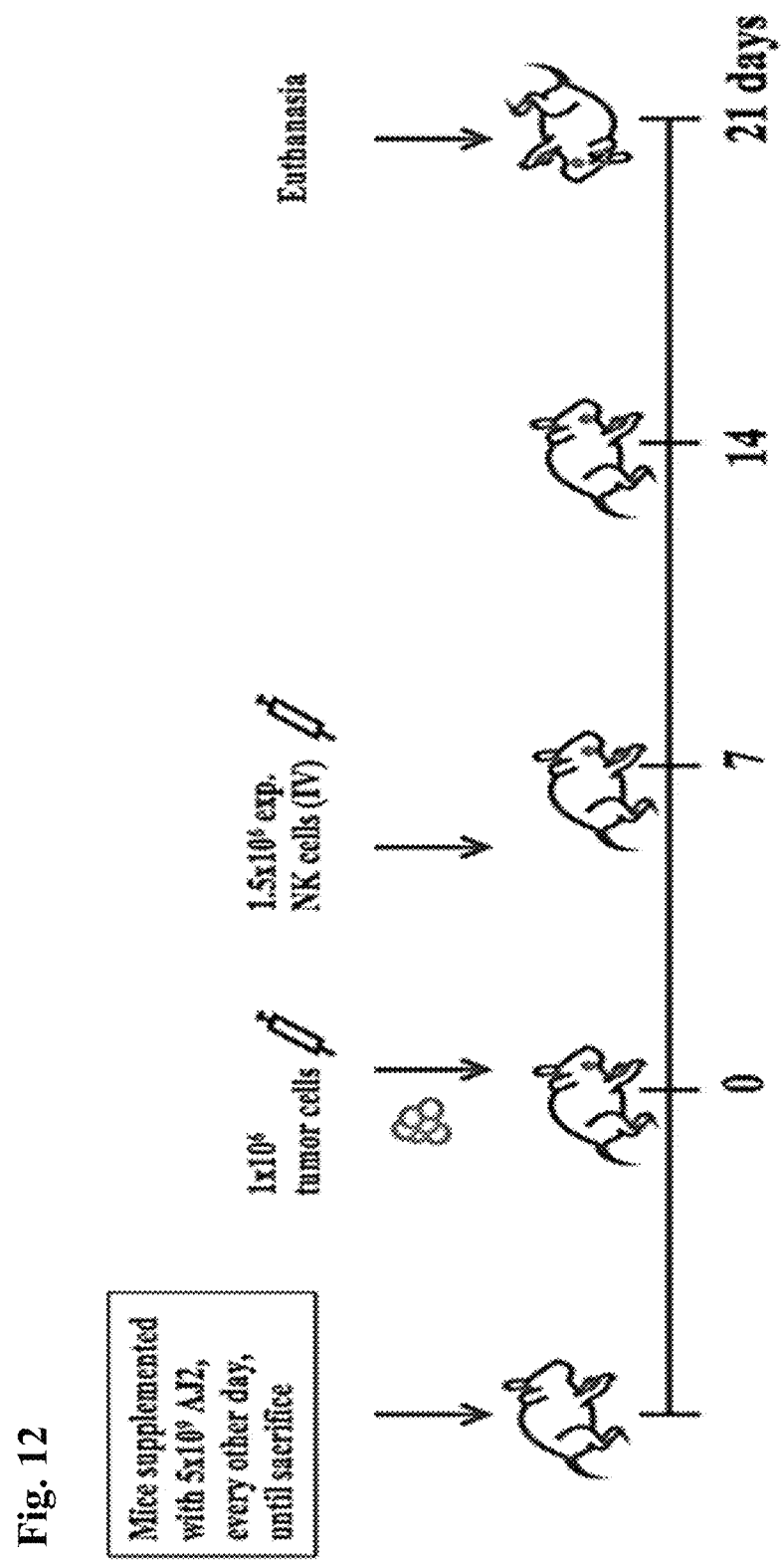
FIG. 12 shows an exemplary experimental outline of probiotic supplementation in combination with NK immunotherapy for OSCSCs orthotopically implanted BLT mice. Prior to tumor implantation, selected mice were fed 5×10$^9$ AJ2 bacteria (the combination of 8 probiotic strains listed above) every other day, beginning one week prior to tumor implantation. This adjuvant therapy was continued every other day until the day of sacrifice. For each mouse, lyophilized AJ2 was resuspended in 200 μL of fat free milk, and fed to them via pipetting. OSCSCs were orthotopically injected into the floor of the mouth of hu-BLT mice. Following injection of tumor cells, all mice were continuously monitored for disease progression, every other day. Seven days after tumor implantation, selected hu-BLT mice received 1.5×10$^6$ human, osteoclast-expanded NK cells via tail vein (IV) injection. Mice were observed for overall signs of morbidity, such as loss of weight, ruffled fur, hunched posture, and immobility. Mice were sacrificed 3 weeks following initial tumor implantation.

Example 4: Adjuvant Probiotic Supplementation in Combination with Osteoclast-Expanded NK Immunotherapy in Hu-BLT Mice The hu-BLT mouse model was used to investigate the use of adjuvant probiotic supplementation in combination with NK cell-based adoptive immunotherapy using the expansion method described in Example 3 (detailed in the Materials and Methods section in Example 1), to target cancer stem-like cells. FIG. 12 provides a detailed description of the experimental design.

NK Immunotherapy Resulted in the Recruitment of T Cells in Various Tissue Compartments; AJ2 Probiotic Supplementation Further Increased this Effect To investigate the immunomodulatory effect of NK immunotherapy in the humanized mouse cancer model, multiple tissue compartments were harvested and analyzed for immune cell markers. In all immune tissue compartments harvested from the mice on the day of sacrifice, including bone marrow (Table 3A), blood (Table 4) and spleen (Table 6A), CD3+ immune cells (T cells) had an elevated presence in mice that received NK immunotherapy—the combination with AJ2 supplementation demonstrated a higher level of T cell presence. The presence of higher T cells was observed during later time points of cultures, as well (Tables 3B, 6B). Bone marrow harvested from mice also showed an elevated presence of MDSCs (myeloid derived suppressor cells) in mice that received NK immunotherapy (Table 13). When considering the percentages of T cells at the time of sacrifice, PBMCs, spleen and BM exhibited higher percentages of CD3+T cells, and BM exhibited an elevation in HLADR+CD11B+ immune subsets in tumor-bearing mice injected with NK cells alone or in combination with AJ2 feeding.

In addition to immune tissue showing elevated levels of T cells, this trend was also observed in the immune cells (CD45+ cells) present within the tumors resected from the animals (Table 9). Mice that received NK immunotherapy showed a higher percentage of T cells within the immune population present in the tumors, with AJ2 supplementation showing a slightly higher level. The majority of infiltrating CD45+ immune cells were CD3+ T cells with CD4+ T cell subsets having moderately higher proportions than CD8+ T cells, and demonstrating CD3+CD56+CD16+ NKT subsets. When tumors were treated with IL-2, the high intensity CD4, CD8 and CD56/CD16 surface expression, which were down-regulated during interaction with tumors, was restored. The condition of AJ2 supplementation alone as treatment showed a much higher level of CD3 cells as compared to the control receiving only oral tumor injection (Table 9).

In separate experiments, the majority of T cell contaminants from OC-expanded NK cells were found to be CD8+ T cells. T cell contaminants from day 9 OC-expanded NK cells were sorted out to obtain purified T cells and NK cells. NK cells were then tested for purity using CD16 and CD3/56 antibodies. NK cells and T cells were then treated with IL-2 for 18-20 hours before they were used in $^{51}$Cr release assay against OSCSCs and K562s. CD3+ T cells isolated from OC-expanded NK cells failed to lyse OSCSCs or K562s. Supernatants from NK cells secreted significantly higher levels of IFN-γ compared to T cells.

Decreased cytotoxicity and lower IFN-γ secretion by NK cells from patients coincides with increased expansion of T cells. When cultured with OCs, purified NK cells from cancer patients were unable to maintain the expansion of NK cells and indeed, by day 12, greater than half of the expanding cells were T cells. Moreover, by day 31, only 10% of the remaining cells in the culture were NK cells. In addition, when total numbers of expanded NK and T cells were determined within 31-36 days of expansion in cancer patients, there were less expanding cells from cancer patients when compared to healthy controls, and the levels of expanding T cells were significantly higher than NK cells. In contrast, NK cells isolated from healthy donors maintained the expansion of NK cells and the levels of NK expansion were significantly higher than T cells. No or much lower proliferation of NK cells were observed with patient NK cells when compared to healthy NK cells at different days of culture. No significant cell death could be observed in the expanding cells either from healthy donor or patient, although the death rate was slightly higher in cells from the patient than healthy donor.

Patient's NK cells cultured with OCs lysed OSCSCs significantly less when compared with the healthy NK cells cultured with OCs. When normalized based on the number of NK cells, cytotoxicity induced per NK cell by patients was less when compared to NK cells from healthy controls. OC-expanded patient NK cells secreted significantly less IFN-γ when compared to healthy OC-expanded NK cells. OC expanded oral cancer patients' NK cells secreted significantly less IL-10 when compared to healthy NK cells, whereas those from pancreatic cancer patients secreted higher IL-10 when compared to healthy NK cells. No significant differences could be observed for the levels of IL-6 secretion by healthy or cancer patients NK cells. The levels of NKG2D surface expression were similar on healthy as compared to patient NK cells expanded by the osteoclasts. The intensity of CD94 expression is higher on the surface of patient NK cells as compared to healthy control. KIR2, NKp30, NKp44 and NKp46 expressions were lower on the surface of OC-expanded patient NK cells when compared to healthy NK cells, whereas KIR3 expression was either the same or lower on the surface of OC-expanded patient NK cells when compared to healthy NK cells.

Osteoclast activated NK cells substantially increase CD8+ T cell numbers. Cancer patients have on average higher percentages of CD8+ T cells when compared to healthy controls, and lower percentages of CD4+ T cells. When cultured with osteoclasts T cells in the absence of NK cells failed to expand CD8+ T cells, however, purified NK cells activated with OCs which contained undetectable or a very small fraction of contaminating T cells, expanded CD8+ T cells from both healthy and patient cultures, albeit patient NK cell cultures expanded T cells faster than healthy NK cells. T cells isolated from patients had higher levels of CD45RO and lower CD45RA, CD62L, CD28, CCR7 and CD127 when compared to T cells isolated from healthy controls.

OC activated NK cells preferentially expanded CD8+ T cells whereas DC activated NK cells expanded CD4+ T cells. To determine whether there were differences between the subpopulations of T cells expanded by OC vs. DC activated NK cells, the CD4 and CD8 subpopulations in healthy donors were analyzed. OC activated NK cells preferentially expanded CD8+ T cells whereas DC activated NK cells expanded CD4+ T cells. CD8+ T cells expanded by OC activated NK cells exhibited higher CD45RO and CD44, much lower levels of CD62L, CCR7 and CD127 and intermediate levels of CD28 whereas CD4+ T cells expanded by DC activated NK cells exhibited lower levels of CD45RO, intermediate levels of CD44 and higher levels of CD62L, CCR7 with little change in CD127 and lower levels of CD28. T cells activated by either OC or DC in the absence of NK cells exhibited surface profiles similar to those obtained by NK activated DCs with the exception of CD28 expression which resembled that obtained by OC activated NKs. The proportions of CD4 and CD8 within CD3+ T cells were similar between PBMCs and those expanded by either OCs or DCs in the absence of NK cells, and no significant levels of PD-1, Tim 3 or KLRG-1 on T cells either activated by OC or DC in the presence or absence of NK cells could be observed.

Figure 13:
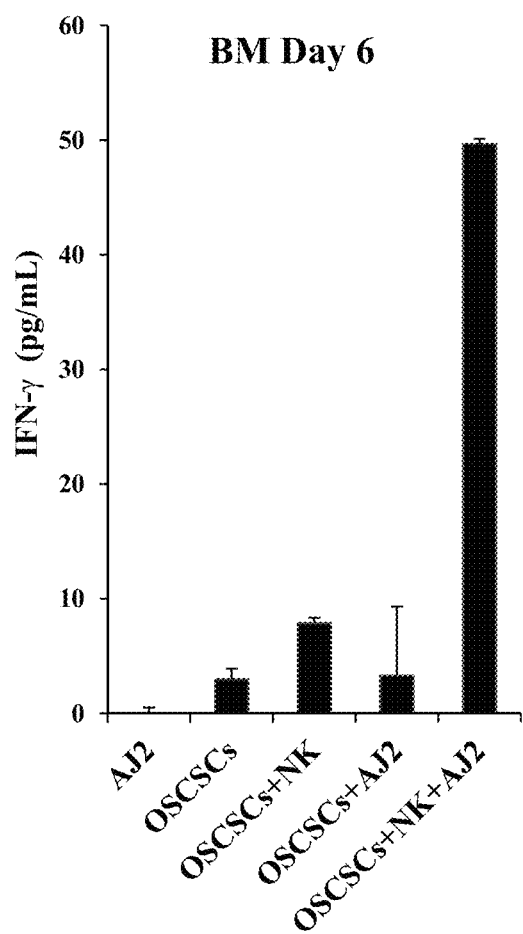
FIG. 13 shows that IFN-γ secretion of IL-2 activated bone marrow cells from hu-BLT mice. Hu-BLT mice were treated as described in FIG. 12. Following euthanasia, femurs were harvested and bone marrow cells were flushed out using RPMI medium supplemented with 10% FBS. Bone marrow cells were cultured at $1\times10^6$ cells/mL and supplemented with IL-2 (1000 units/mL) on day 0. Supernatants were collected at days 3, 6, and 11. Cells were then resuspended at $1\times10^6$ cells/mL and supplemented with IL-2 (1000 units/mL) for each culture time point. IFN-γ secretion levels were determined for day 6 (FIG. 12A) and day 11 (FIG. 12B) supernatants using human IFN-γ ELISA.
Figure 13:
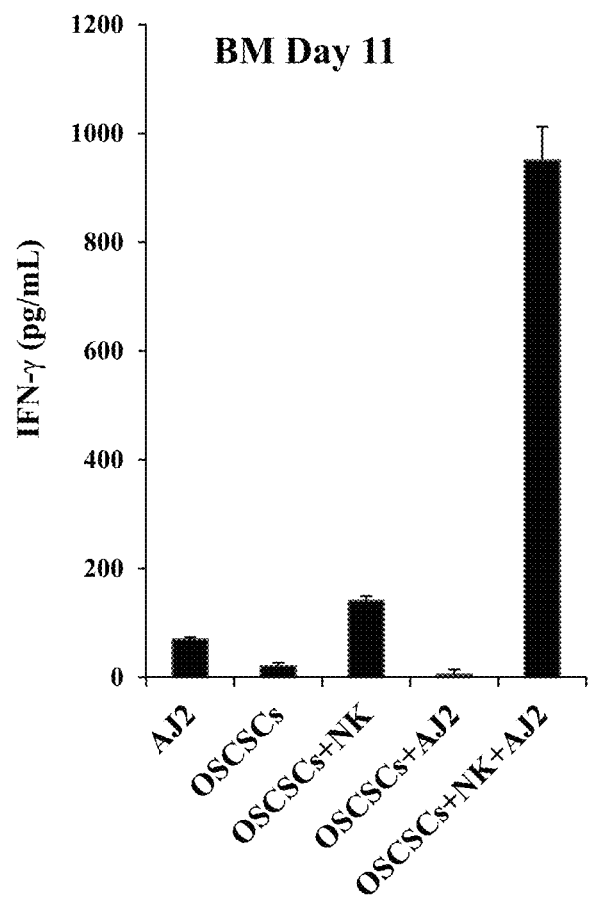
Figure 18:
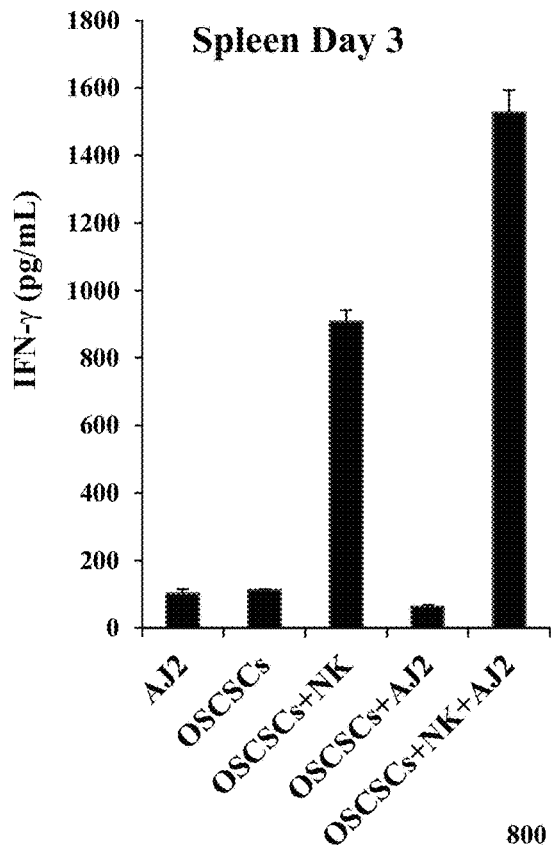
FIG. 18 shows that IFN-γ secretion of IL-2 activated splenocytes from hu-BLT mice. Hu-BLT mice were treated as described in FIG. 12. Following euthanasia, spleens were harvested, dissociated, filtered for single-cell suspension. Splenocytes were cultured at $1\times10^6$ cells/mL and supplemented with IL-2 (1000 units/mL) on day 0. Supernatants were collected at days 3, 6, and 11. Cells were then resuspended at $1\times10^6$ cells/mL and supplemented with IL-2 (1000 units/mL) for each culture time point. IFN-γ secretion levels were determined for day 3 (FIG. 18A), day 6 (FIG. 18B), and day 11 (FIG. 18C) supernatants using human IFN-γ ELISA.
Figure 18:
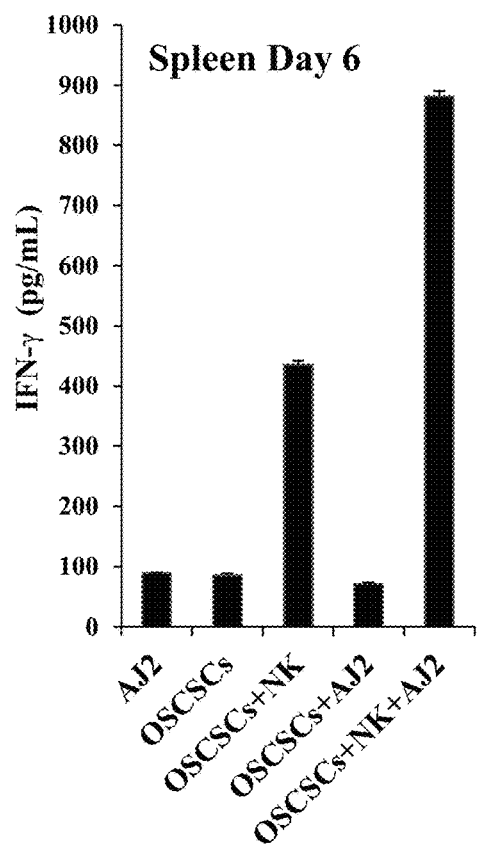
Figure 18:
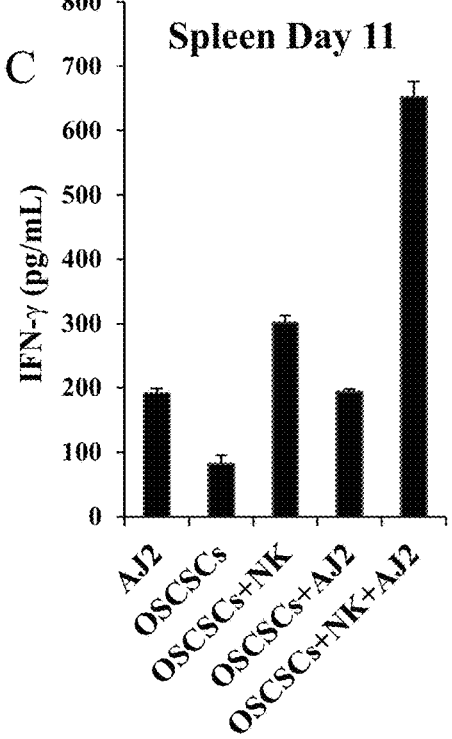
Figure 20:
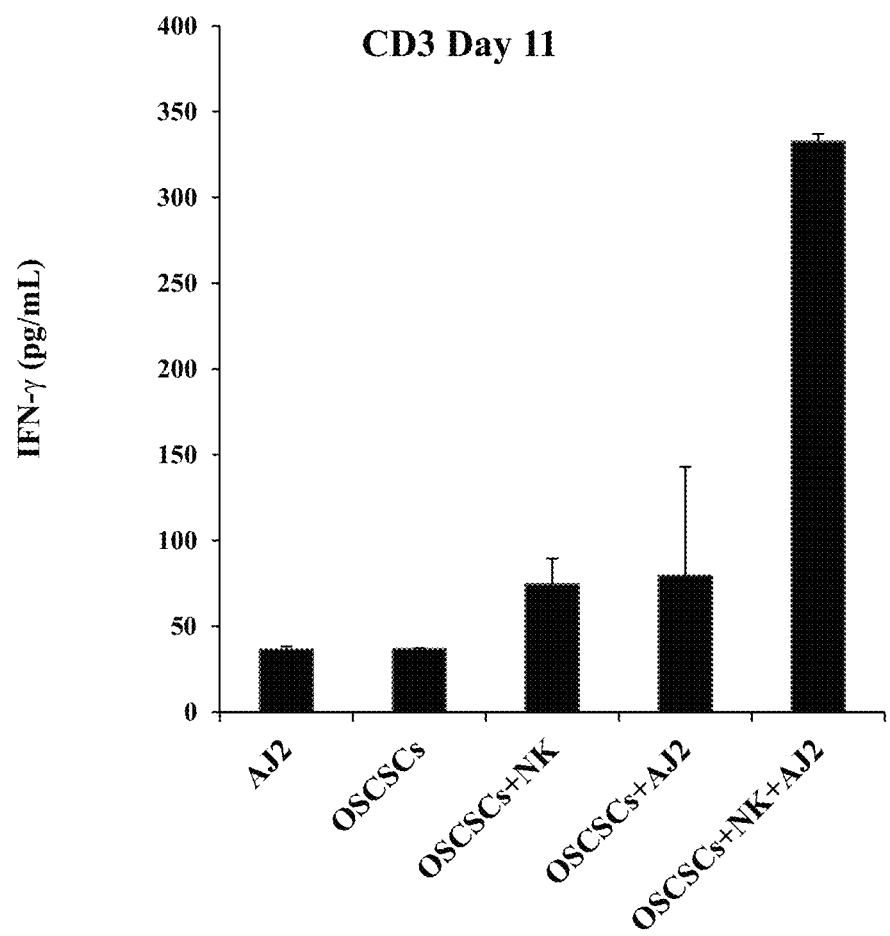
FIG. 20 shows IFN-γ secretion of IL-2 activated CD3+ T cells, positively selected from splenocytes of hu-BLT mice. Hu-BLT mice were treated as described in FIG. 12. Following euthanasia, spleens were harvested, dissociated, filtered for single-cell suspension. Splenocytes underwent CD3 positive selection, and purified T cells were cultured at $1\times10^6$ cells/mL and supplemented with IL-2 (1000 units/mL) on day 0. Supernatants were collected at days 3, 6, and 11. Cells were then resuspended at $1\times10^6$ cells/mL and supplemented with IL-2 (1000 units/mL) for each culture time point. IFN-γ secretion levels were determined for day 11 supernatants using human IFN-γ ELISA.
Figure 22:
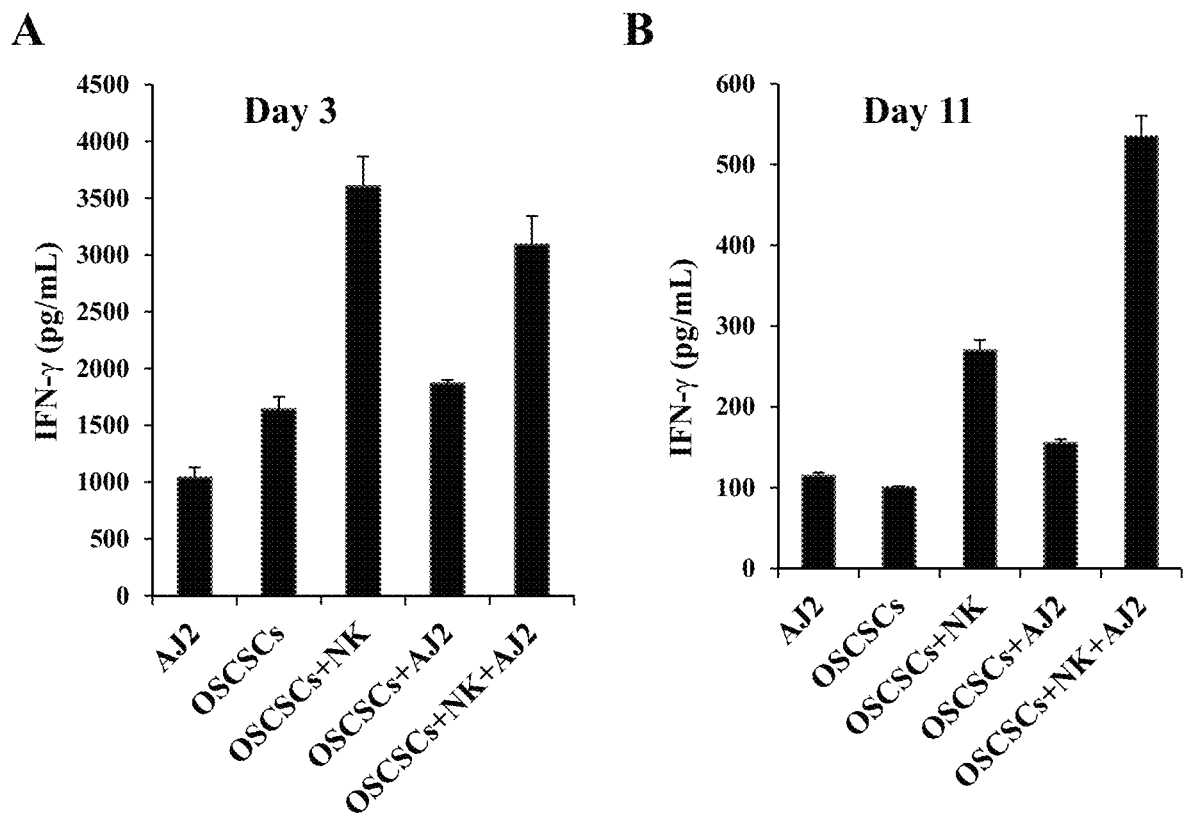
FIG. 22 shows IFN-γ secretion of IL-2 activated CD3 depleted splenocytes from hu-BLT mice. Hu-BLT mice were treated as described in FIG. 12. Following euthanasia, spleens were harvested, dissociated, filtered for single-cell suspension. Splenocytes were depleted of CD3+ cells and cultured at $1\times10^6$ cells/mL, supplemented with IL-2 (1000 units/mL) on day 0. Supernatants were collected at days 3, 6, and 11. Cells were then resuspended at $1\times10^6$ cells/mL and supplemented with IL-2 (1000 units/mL) for each culture time point. IFN-γ secretion levels were determined for day 3 (FIG. 22A) and day 11 (FIG. 22B) supernatants using human IFN-γ ELISA.

NK Immunotherapy Treatment Increased the Cytokine Secretion Levels in Various Tissue Compartments, while AJ2 Probiotic Supplementation Further Increased Cytokine Levels To understand the effect of NK immunotherapy and probiotic supplementation on cytokine levels within various tissue compartments, tissues were harvested and analyzed for cytokine secretion levels. NK immunotherapy, both alone and in combination with AJ2 supplementation induced a high level of IFN-γ secretion during various time points of culture in PBMCs (FIG. 16), splenocytes (FIG. 18, Table 7), and CD3 depleted splenocytes (FIG. 22). Levels of IFN-γ were much higher in the NK immunotherapy in combination with AJ2 supplementation, for various culture time points from bone marrow cells (FIG. 13), splenocytes (FIG. 18, Table 7) and CD3 cells isolated from splenocytes (FIG. 20). Sera collected from mice immediately following sacrifice showed elevated levels of IFN-γ in mice receiving NK immunotherapy— much higher levels in the combination of NK immunotherapy with AJ2 supplementation (Table 5).

Figure 14:
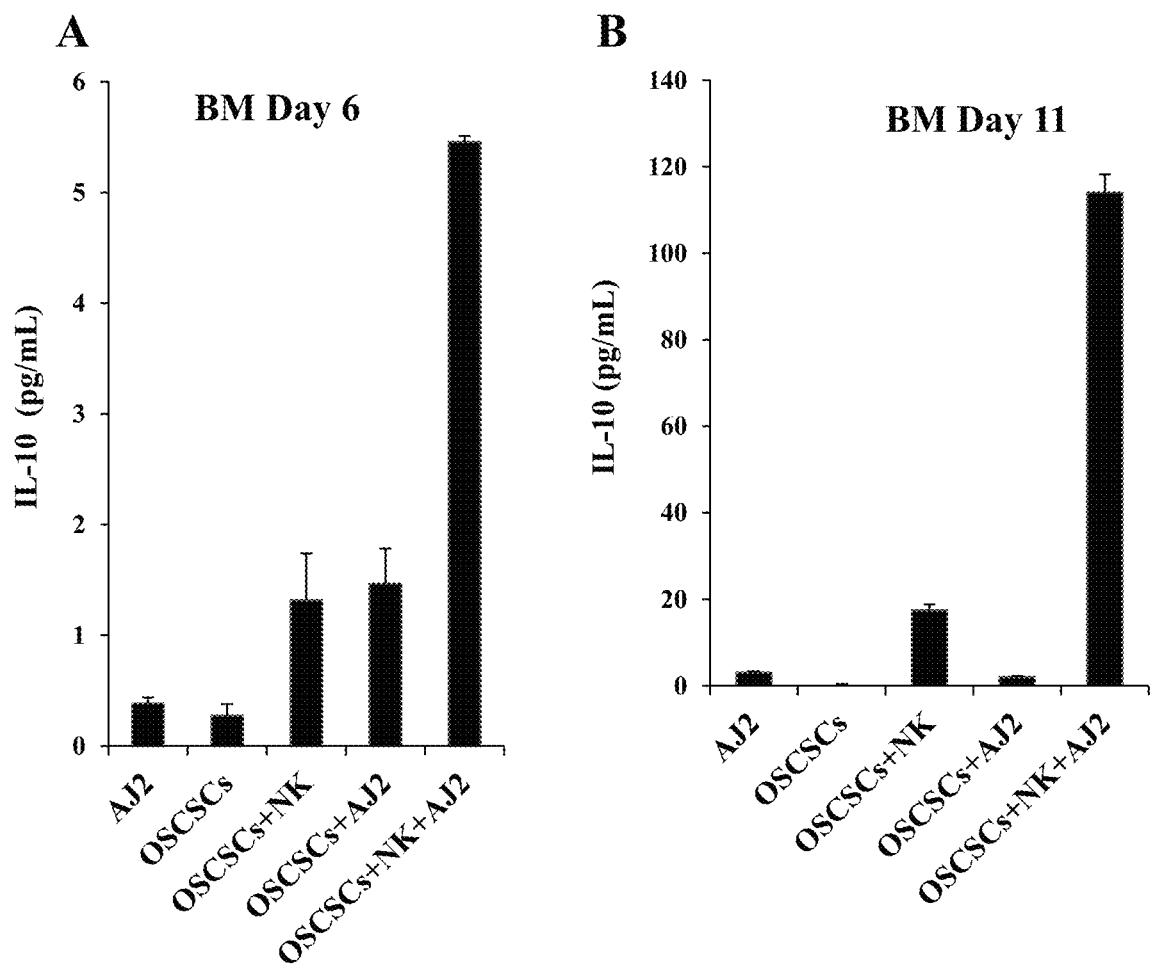
FIG. 14 shows that IL-10 secretion of IL-2 activated bone marrow cells from hu-BLT mice. Hu-BLT mice were treated as described in FIG. 12. Following euthanasia, femurs were harvested and bone marrow cells were flushed out using RPMI medium supplemented with 10% FBS. Bone marrow cells were cultured at $1\times10^6$ cells/mL and supplemented with IL-2 (1000 units/mL) on day 0. Supernatants were collected at days 3, 6, and 11. Cells were then resuspended at $1\times10^6$ cells/mL and supplemented with IL-2 (1000 units/mL) for each culture time point. IL-10 secretion levels for day 6 (FIG. 14A) and day 11 (FIG. 14B) supernatants using human IL-10 ELISA.
Figure 19:
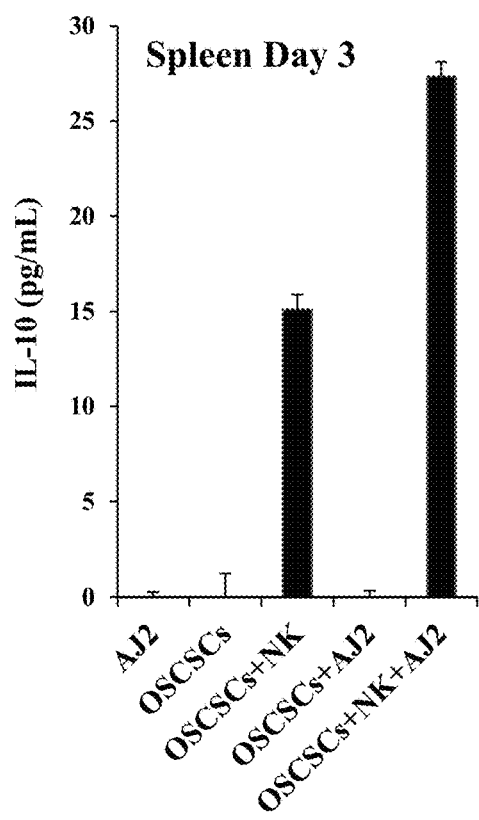
FIG. 19 shows IL-10 secretion of IL-2 activated splenocytes from hu-BLT mice. Hu-BLT mice were treated as described in FIG. 12. Following euthanasia, spleens were harvested, dissociated, filtered for single-cell suspension. Splenocytes were cultured at $1\times10^6$ cells/mL and supplemented with IL-2 (1000 units/mL) on day 0. Supernatants were collected at days 3, 6, and 11. Cells were then resuspended at $1\times10^6$ cells/mL and supplemented with IL-2 (1000 units/mL) for each culture time point. IL-10 secretion levels were determined for day 3 (A) and day 6 (B) supernatants using human IL-10 ELISA.
Figure 19:
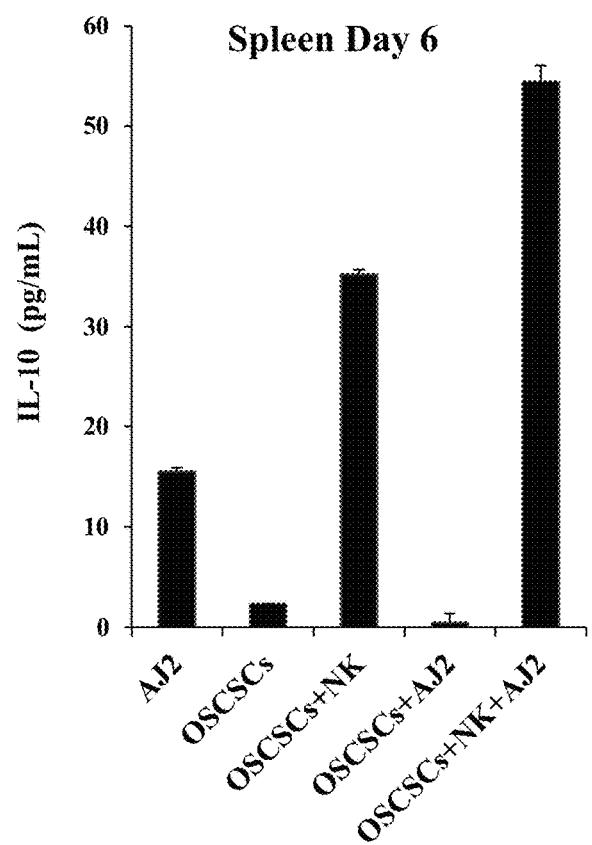
Figure 21:
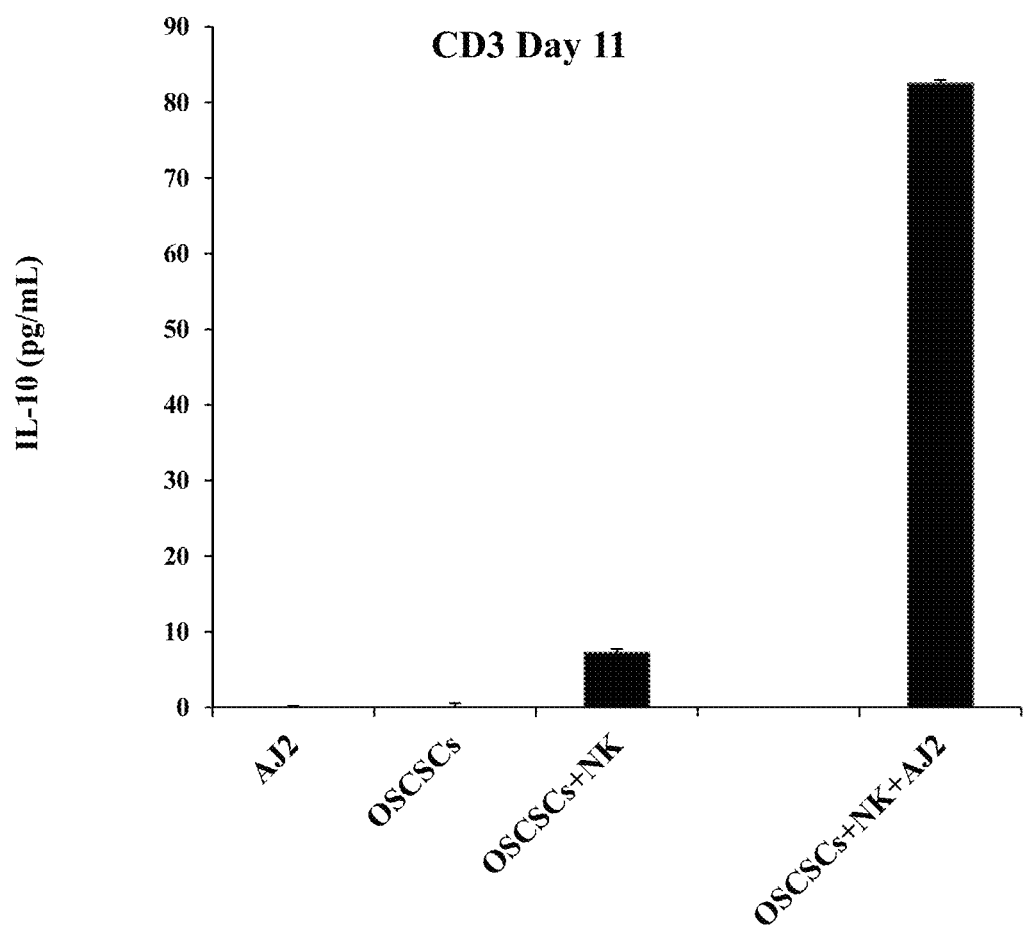
FIG. 21 shows IL-10 secretion of IL-2 activated CD3+ T cells, positively selected from splenocytes of hu-BLT mice. Hu-BLT mice were treated as described in FIG. 12. Following euthanasia, spleens were harvested, dissociated, filtered for single-cell suspension. Splenocytes underwent CD3 positive selection, and purified T cells were cultured at $1\times10^6$ cells/mL and supplemented with IL-2 (1000 units/mL) on day 0. Supernatants were collected at days 3, 6, and 11. Cells were then resuspended at $1\times10^6$ cells/mL and supplemented with IL-2 (1000 units/mL) for each culture time point. IL-10 secretion levels were determined for day 11 supernatants using human IL-10 ELISA.
Figure 23:
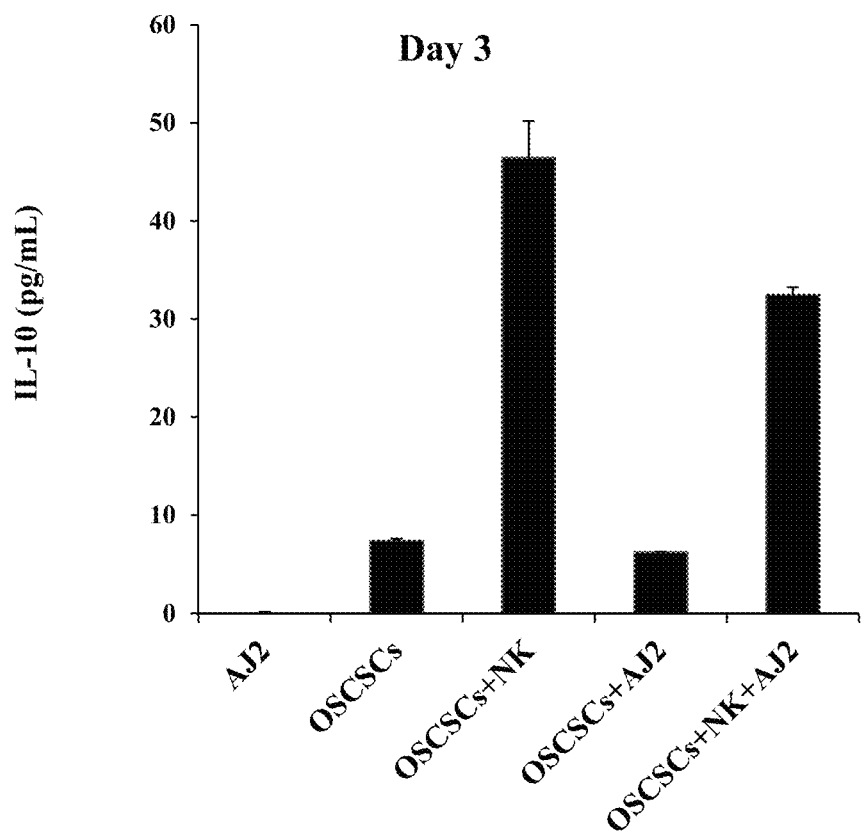
FIG. 23 shows IL-10 secretion of IL-2 activated CD3 depleted splenocytes from hu-BLT mice. Hu-BLT mice were treated as described in FIG. 12. Following euthanasia, spleens were harvested, dissociated, filtered for single-cell suspension. Splenocytes were depleted of CD3+ cells and cultured at $1\times10^6$ cells/mL, supplemented with IL-2 (1000 units/mL) on day 0. Supernatants were collected at days 3, 6, and 11. Cells were then resuspended at $1\times10^6$ cells/mL and supplemented with IL-2 (1000 units/mL) for each culture time point. IL-10 secretion levels were determined for day 11 supernatants using human IL-10 ELISA.

Mice receiving NK immunotherapy and/or AJ2 supplementation showed increased levels of IL-10 cytokine in the sera (Table 5A), while only NK immunotherapy receiving mice showed elevated levels of IL-10 in cell cultures conducted using bone marrow cells (FIG. 14B), splenocytes (FIG. 19), CD3 cells isolated from splenocytes (FIG. 21), and CD3 depleted splenocytes (FIG. 23). Probiotic supplementation along with NK immunotherapy synergistically increased the level of IL-10 secreted by bone marrow cells (FIG. 14), splenocytes (FIG. 19), and CD3 cells isolated from splenocytes (FIG. 21), observed at various time points.

Other cytokines that followed a similar trend include the elevation of IL-23 and IL-17 in the sera of mice receiving NK immunotherapy, with a significant increase in IL-23 levels in the NK immunotherapy combined with AJ2 supplementation (Table 5A). Certain markers, such as IL-8, MIP-3a and ITAC were much higher in the tumor only control group, indicating a potential immunological marker for oral cancer (Table 4B).

Figure 15:
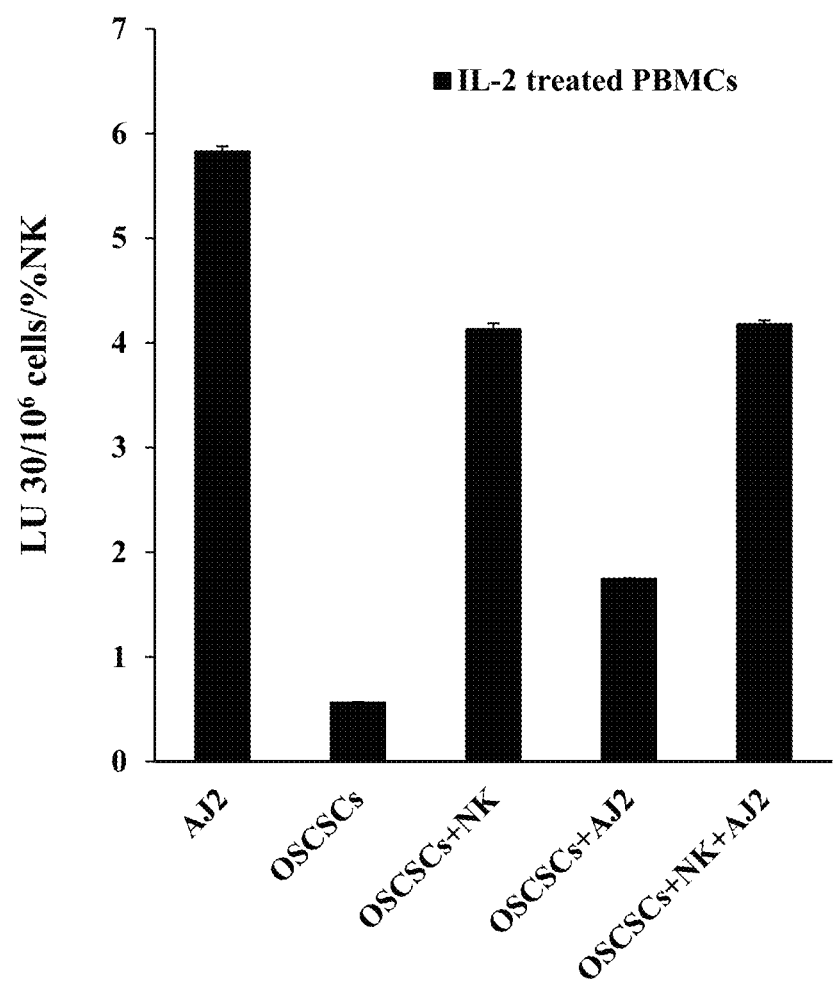
FIG. 15 shows that cell-mediated cytotoxicity of IL-2 activated PBMCs from hu-BLT mice. Hu-BLT mice were treated as described in FIG. 12. Following euthanasia, blood was collected from the mice and PBMCs were separated using Ficoll-Hypaque centrifugation. PBMCs were cultured at $0.4\times10^6$ cells/mL and supplemented with IL-2 (1000 units/mL) on day 0, 3 and 7. Cytotoxic function of PBMCs was measured on day 7 using a standard 4-hour $^{51}$Cr release assay against radioactively labeled OSCSCs (target cells). Lytic units (LU $30/10^6$) were determined as described in the Materials and Methods in Example 1.
Figure 17:
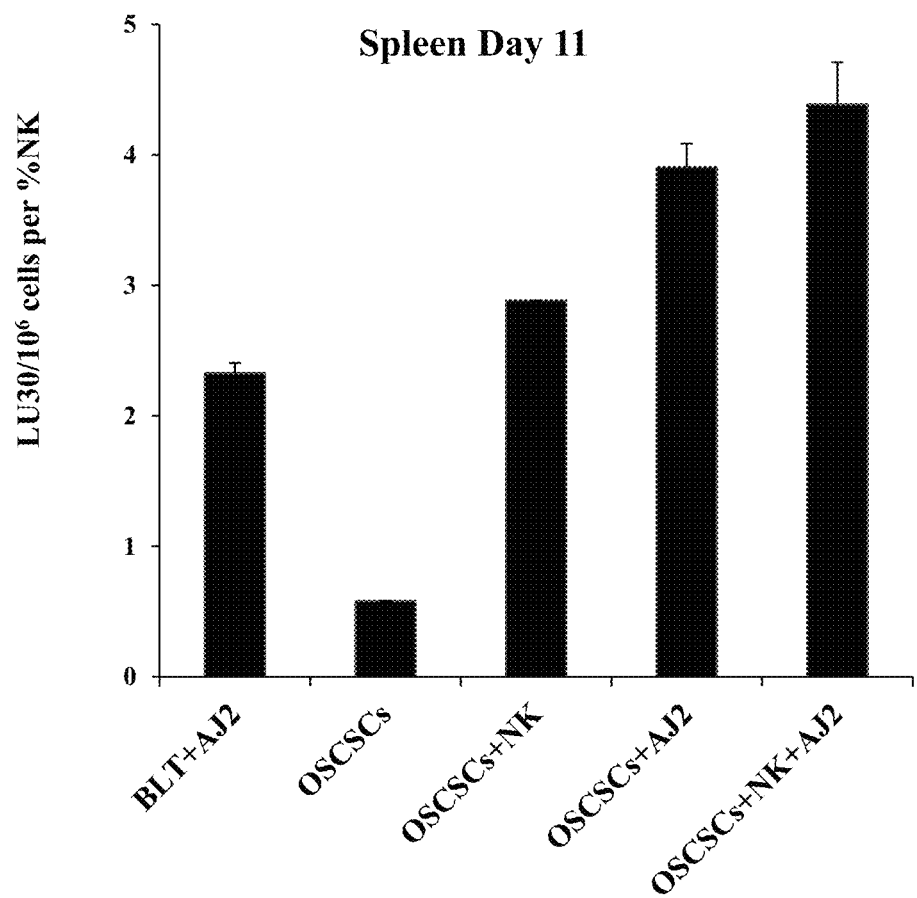
FIG. 17 shows that cell-mediated cytotoxicity of IL-2 activated splenocytes from hu-BLT mice. Hu-BLT mice were treated as described in FIG. 12. Following euthanasia, spleens were harvested, dissociated, filtered for single-cell suspension. Splenocytes were cultured at $1\times10^6$ cells/mL and supplemented with IL-2 (1000 units/mL) on day 0. Supernatants were collected at days 3, 6, and 11. Cells were then resuspended at $1\times10^6$ cells/mL and supplemented with IL-2 (1000 units/mL) for each culture time point. Cytotoxic function of IL-2 treated splenocytes was measured on day 11 using a standard 4-hour $^{51}$Cr release assay against radioactively labeled OSCSCs (target cells). Lytic units (LU $30/10^6$) were determined as described in the Materials and Methods in Example 1.

Tumor-Bearing Mice had Reduced Cytotoxic Function in Various Tissue Compartments, while Mice Receiving NK Immunotherapy Treatment had Significantly Improved Cytotoxic Functions To investigate the cytotoxic function of NK cells within these tissue compartments, $^{51}$Cr release assay was conducted using immune cells from harvested tissues. PBMCs were cultured as described in FIG. 15, and on day 7, they were used in $^{51}$Cr release assay to measure their cytotoxic function. PBMCs from healthy control (received only AJ2 supplementation and no tumor) were highly cytotoxic, and mice receiving NK immunotherapy also had a high level of cytotoxicity. The tumor control group showed very low cytotoxicity, even compared to the group receiving AJ2 supplementation as a control treatment for the tumor (FIG. 15). Splenocytes cultured as described in FIG. 17, were also used in $^{51}$Cr release assay to measure their cytotoxic function. Only splenocytes of the tumor control group had a significantly reduced level of cytotoxicity compared to the other groups (FIG. 17). Cytotoxic levels of NK immunotherapy and/or AJ2 supplementation groups were either comparable to or higher than the control (no tumor bearing) group (FIG. 17). In another group of experiments, NK-injected tumor-bearing mice, either alone or in combination with feeding AJ2, exhibited elevated NK cytotoxicity in all tissue compartments, with the highest increase observed when mice were fed AJ2 and injected with NK cells and anti-PD1. However, anti-PD1 did not further increase (in some situations even decreased) IFN-γ secretion in tumor-bearing hu-BLT mice with NK injection and AJ2.

Figure 24:
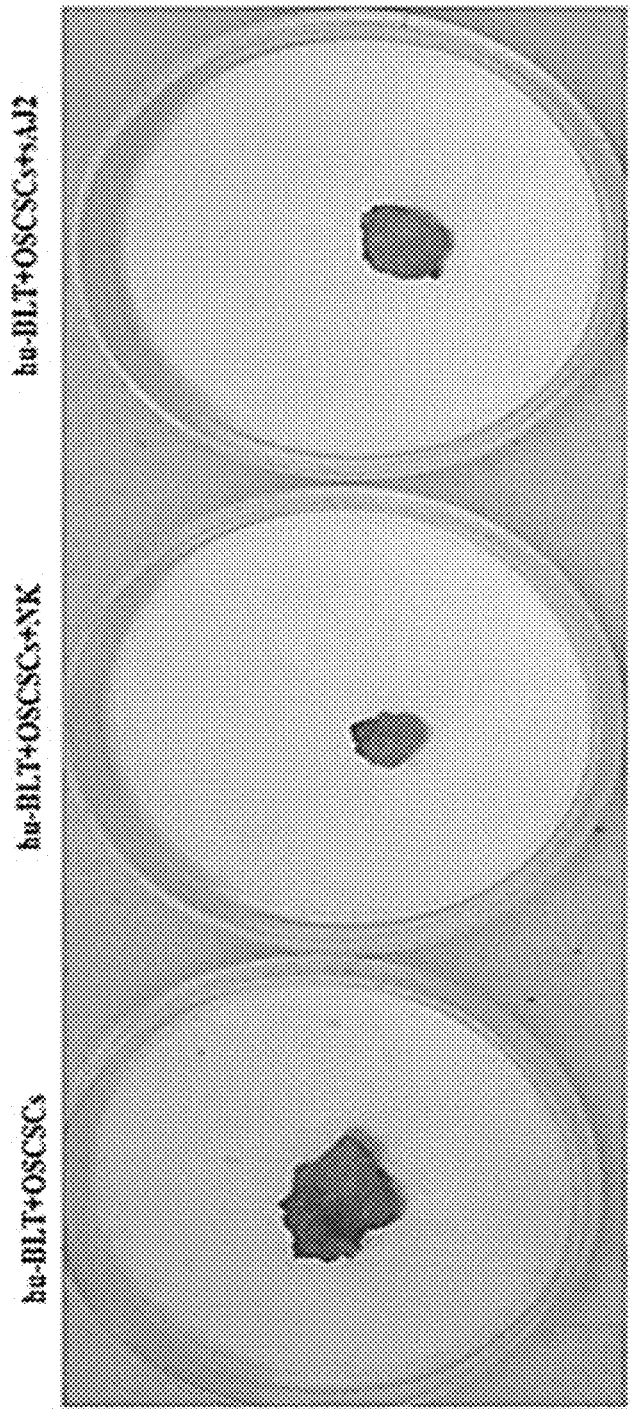
FIG. 24 shows size analysis of oral tumors resected from hu-BLT mice. Hu-BLT mice were treated as described in FIG. 12. Following euthanasia, oral tumors were harvested and photographed side-by-side.

NK Immunotherapy, Both Alone and in Combination with AJ2 Supplementation, Prevented Tumor Growth In Vivo Following sacrifice of animals, oral tumors were resected from the hu-BLT mice. When comparing sizes side-by-side, it was visibly clear that mice receiving NK immunotherapy had smaller tumors (FIG. 24). This information was further validated through both measurement of the tumors on a scale, as well as tumor cell counts following dissociation of the harvested tumors (Table 8). Tumors of mice receiving NK immunotherapy weighted less and were composed of less tumor cells compared to the other controls. In addition, tumor weights were substantially less in NK-injected and AJ2 fed mice, compared to mice fed with AJ2 and not given NK injection.

Figure 25:
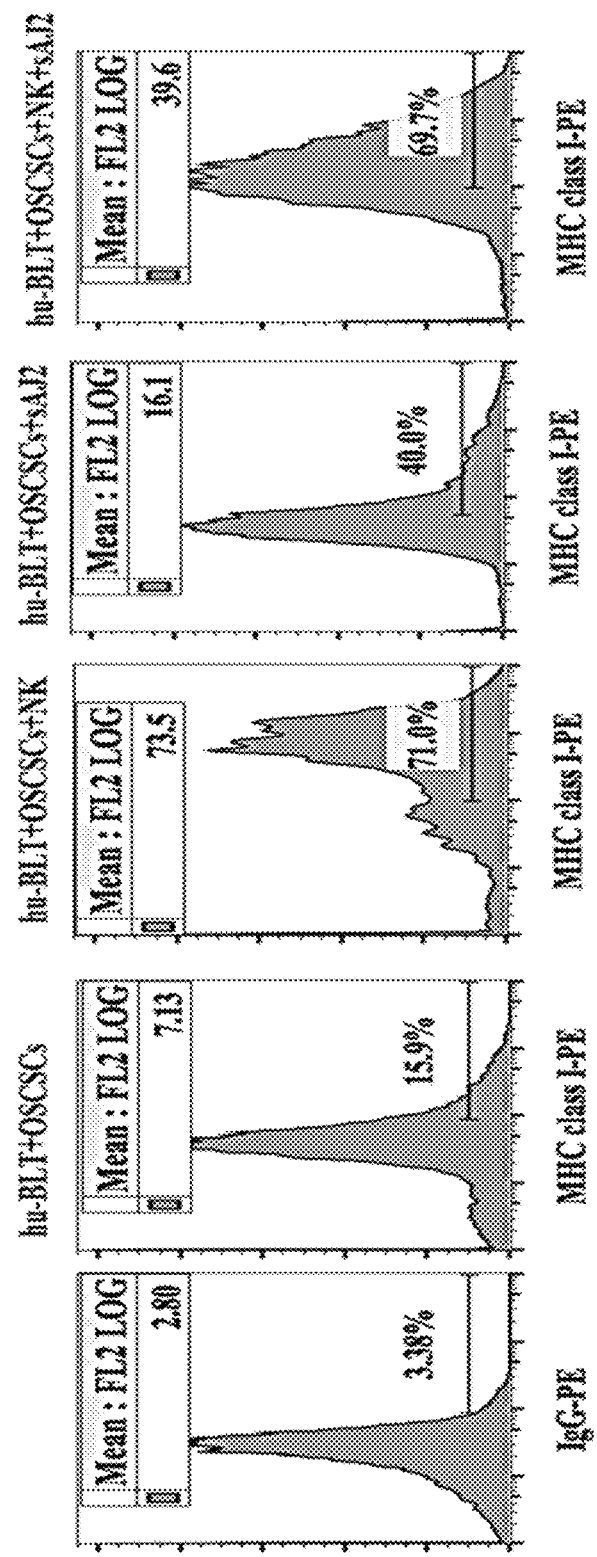
FIG. 25 shows surface expression of MHC-I on oral tumors resected from hu-BLT mice. Hu-BLT mice were treated as described in FIG. 12. Following euthanasia, oral tumors were harvested, dissociated, and filtered for single-cell suspension. Flow cytometry was conducted on day 0, using PE-conjugated MHC-I antibodies. Isotype control antibodies were used as controls.
Figure 26:
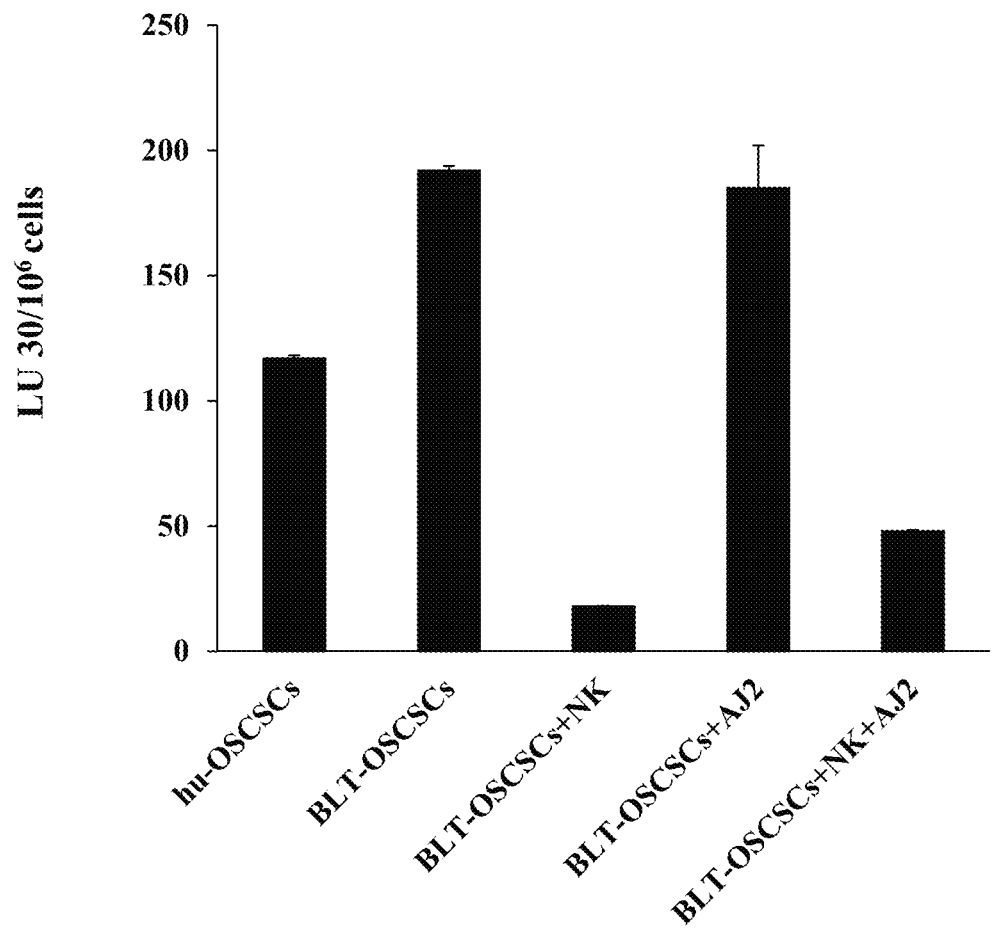
FIG. 26 shows NK-cell mediated cytotoxicity against oral tumors resected from hu-BLT mice. Hu-BLT mice were treated as described in FIG. 12. Following euthanasia, oral tumors were harvested, dissociated and filtered for single-cell suspension. Cell for each tumor were cultured at $0.75 \times 10^6$ cells per well at day 0. Cells were detached at day 7, and re-cultured at 10,000 cells for each condition. On day 15, oral tumor cells were detached and used for experimentation. Tumor sensitivity to NK-cell mediated cytotoxicity was measured using a standard 4-hour $^{51}Cr$ release assay against freshly isolated and IL-2 (1000 units/mL) activated NK cells. Lytic units (LU $30/10^6$) were determined.

Tumors Dissected from Mice Receiving NK Immunotherapy were More Differentiated, Resistant to NK Cell-Mediated Cytotoxicity, and Slower Growing To investigate the effectiveness of NK immunotherapy in differentiating OSCSCs in vivo, hu-BLT mice were treated as described in FIG. 12. Following sacrifice, resected tumors were analyzed using flow cytometry. Mice receiving NK immunotherapy following oral tumor injection exhibited a more differentiated phenotype, higher expression of MHC-I, compared to those not receiving immunotherapy (FIG. 25). Resected tumors were also cultured for growth analysis. Tumors from mice, which received NK immunotherapy, had a much slower growth rate compared to mice under conditions not receiving immunotherapy (Table 10). Once tumors were grown in culture, $^{51}$Cr release assay was conducted to measure the susceptibility of these cells to NK cell-mediated lysis. Tumors from mice that received NK immunotherapy were more resistant to NK cell-mediated lysis, whereas mice that did not receive the treatment were significantly more susceptible to NK cell mediated lysis, indicated their maintained stem-like feature (FIG. 26). When NK-mediated differentiation of tumor cells was blocked with anti-IFN-γ and anti-TNF-α antibodies before implantation, the susceptibility of tumors to NK cell-mediated cytotoxicity was restored. In addition, oral tumors from hu-BLT mice injected with NK cells secreted relatively less VEGF when standardized based on the secretion of VEGF from tumor-bearing mice.

NK Immunotherapy Induced Significant Cell Death in OSCSCs Differentiated with IL-2+ Anti-CD16 mAb Treated NK Supernatant Differentiation of OSCSCs with NK supernatants resulted in significant susceptibility of tumors to CDDP (Cisplatin). Although less effective than CDDP, Paclitaxel (PTX) also mediated higher cell death of NK-differentiated OSCSCs, while addition of N-acetylcysteine (NAC) significantly increased Paclitaxel-mediated cell death. Blocking NK-mediated differentiation of OSCSCs with anti-IFN-γ and anti-TNF-α antibodies substantially decreased cell death induced by CDDP or paclitaxel with or without NAC. Treatment of OSCCs, patient-derived differentiated oral tumor, with CDDP or paclitaxel and NAC also exhibited higher cell death.

Table 3: Human immune cell populations present in the bone marrow of hu-BLT mice

| 3A | | | |
|---|---|---|---|
| BM Day 0 CD45+ | CD16 + 56 | CD3 | HLADR+CD11b |
| AJ2 control | 0.91 | 2.14 | 10.2 |
| OSCSCs | 1.54 | 2.12 | 11.1 |
| OSCSCs + NK | 1.45 | 2.36 | 15.7 |
| OSCSCs + AJ2 | 1.83 | 1.79 | 11.2 |
| OSCSCs + NK + AJ2 | 2.51 | 5.98 | 16.1 | assessed via flow cytometry. Cells were gated within the human CD45 positive population and isotype control antibodies were used as controls (Table 3A). Bone marrow cells were cultured at $1\times10^6$ cells/mL and supplemented with IL-2 (1000 units/mL) on day 0, day 3, day 6, and day 11. Flow cytometry was conducted on day 11, using FITC, PE, and/or PE-Cy5 conjugated antibodies against CD45, CD3, CD16, CD56, or CD8. Cells were gated within the human CD45 positive population and isotype control antibodies were used as controls (Table 3B).

TABLE 4

| Human immune cell populations present in the PBMCs of hu-BLT mice | | |
|---|---|---|
| PBMCs Day 0 CD45+ | CD16 + 56 | CD3 |
| AJ2 control | 9.67 (3.41) | 66.0 |
| OSCSCs | 28.2 (8.97) | 44.6 |
| OSCSCs + NK | 12.4 (4.46) | 67.6 |
| OSCSCs + AJ2 | 20.4 (7.57) | 50.2 |
| OSCSCs + NK + AJ2 | 10.0 (4.64) | 72.8 |

Hu-BLT mice were treated as described in FIG. 12. Following euthanasia, blood was collected from the mice and PBMCs were separated using Ficoll-Hypaque centrifugation. Surface expression of CD45, CD3, CD16, and CD56 was conducted using FITC, PE and/or PE-Cy5 conjugated antibodies and assessed via flow cytometry. Cells were gated within the human CD45 positive population and isotype control antibodies were used as controls.

Table 5: Cytokine and chemokine profiles of sera samples collected from the cardiac blood of hu-BLT mice post-sacrifice

| 5A | | | | | | | | | | | | | | | | |
|---|---|---|---|---|---|---|---|---|---|---|---|---|---|---|---|---|
| Sera (pg/mL) | GM-CSF | IFN-γ | IL-10 | IL12p70 | IL-13 | IL-17A | IL-1β | IL-2 | IL-21 | IL-4 | IL-23 | IL-5 | IL-6 | IL-7 | IL-8 | TNF-α |
| AJ2 control | 0 | 1 | 1 | 2 | 0 | 4 | 0 | 4 | 0 | 0 | 0 | 0 | 0 | 4 | 14 | 4 |
| OSCSCs | 19 | 5 | 2 | 1 | 0 | 3 | 0 | 0 | 0 | 0 | 0 | 3 | 4 | 2 | 329 | 12 |
| OSCSCs + NK | 15 | 8 | 5 | 2 | 5 | 10 | 1 | 0 | 5 | 3 | 55 | 0 | 3 | 3 | 32 | 8 |
| OSCSCs + AJ2 | 0 | 2 | 13 | 2 | 0 | 2 | 0 | 0 | 0 | 0 | 0 | 0 | 0 | 3 | 139 | 9 |
| OSCSCs + NK + AJ2 | 48 | 21 | 13 | 9 | 7 | 17 | 7 | 3 | 7 | 13 | 400 | 1 | 3 | 6 | 6 | 5 |

| 3B | | | |
|---|---|---|---|
| BM Day 11 CD45+ | CD16 + 56 | CD3+ | CD3+ CD8+ |
| AJ2 control | 67.4 | 8.32 | 4.70 |
| OSCSCs | 63.1 | 6.31 | 4.43 |
| OSCSCs + NK | 54.5 | 15.22 | 8.70 |
| OSCSCs + AJ2 | 57.5 | 5.22 | 3.30 |
| OSCSCs + NK + AJ2 | 48.5 | 37.02 | 15.8 |

| 5B | | | | |
|---|---|---|---|---|
| Sera (pg/mL) | ITAC | FRACTALKINE | MIP-3α | MIP-1α | MIP-1β |
| AJ2 control | 37 | 0 | 0 | 0 | 7 |
| OSCSCs | 101 | 0 | 46 | 0 | 10 |
| OSCSCS + NK | 20 | 69 | 11 | 11 | 10 |
| OSCSCs + AJ2 | 41 | 0 | 2 | 0 | 11 |
| OSCSCs + NK + AJ2 | 17 | 249 | 16 | 23 | 16 |

Hu-BLT mice were treated as described in FIG. 12. Following euthanasia, femurs were harvested and bone marrow cells were flushed out using RPMI medium supplemented with 10% FBS. Surface expression of CD45, CD3, CD16, CD56, HLADR, and/or CD11b was conducted using FITC, PE and/or PE-Cy5 conjugated antibodies and Hu-BLT mice were treated as described in FIG. 12. Following euthanasia, sera were harvested from cardiac blood. Multiplex array analysis was conducted with sera samples to measure cytokines (Table 5A) and chemokines (Table 5B). Analysis was performed using a MAGPIX Luminex multiplex instrument and data was analyzed using the proprietary software (xPONENT 4.2).

Table 6: Human immune cell populations present in the splenocytes of hu-BLT mice.

| 6A | | |
|---|---|---|
| Spleen Day 0 CD45+ (A gate) | CD16 + 56 | CB3 |
| AJ2 control | 0.98 | 55.8 |
| OSCSCs | 2.86 | 38.2 |
| OSCSCs + NK | 0.81 | 64.1 |
| OSCSCs + AJ2 | 3.66 | 52.1 |
| OSCSCs + NK + AJ2 | 1.50 | 69.9 |

| 6B | | |
|---|---|---|
| Spleen Day 11 CD45+ | CD3+ | CD3+ CD8+ |
| AJ2 control | 40.2 | 28.2 |
| OSCSCs | 34.61 | 19.8 |
| OSCSCs + NK | 73.0 | 39.2 |
| OSCSCs + AJ2 | 14.12 | 11.1 |
| OSCSCs + NK + AJ2 | 81.3 | 50.2 |

Hu-BLT mice were treated as described in FIG. 12. Following euthanasia, spleens were harvested, dissociated, filtered for single-cell suspension. Surface expression of CD45, CD3, CD16 and/or CD56 was conducted using FITC, PE and/or PE-Cy5 conjugated antibodies and assessed via flow cytometry. Cells were gated within the human CD45 positive population and isotype control antibodies were used as controls (Table 6A). Splenocytes were cultured at $1\times10^6$ cells/mL and supplemented with IL-2 (1000 units/mL) on day 0, day 3, day 6, and day 11. Flow cytometry was conducted on day 11, using FITC, PE, and/or PE-Cy5 conjugated antibodies against CD45, CD3, or CD8. Cells were gated within the human CD45 positive population and isotype control antibodies were used as controls (Table 6B).

Table 7: Cytokine secretion profile of IL-2 activated splenocytes from hu-BLT mice

| 7A | | | | | | |
|---|---|---|---|---|---|---|
| Spleen Day 3 | IL-6 | IFN-γ | GM-CSF | TNF-α | IL-8 | IL-10 |
| AJ2 control | 74 | 250 | 103 | 52 | 2418 | 5 |
| OSCSCs | 134 | 263 | 106 | 56 | 5832 | 5 |
| OSCSCs + NK | 1342 | 393 | 151 | 64 | 11227 | 10 |
| OSCSCs + AJ2 | 23 | 230 | 68 | 49 | 947 | 2 |
| OSCSCs + NK + AJ2 | 1332 | 585 | 164 | 74 | N/A | 16 |

| 7B | | | | | | |
|---|---|---|---|---|---|---|
| Spleen Day 6 | IL-6 | IFN-γ | GM-CSF | TNF-α | IL-8 | IL-10 |
| AJ2 control | 24 | 244 | 103 | 51 | 672 | 13 |
| OSCSCs | 57 | 245 | 104 | 53 | 1613 | 6 |
| OSCSCs + NK | 242 | 328 | 238 | 56 | 4878 | 25 |
| OSCSCs + AJ2 | 14 | 226 | 72 | 47 | 283 | 3 |
| OSCSCs + NK + AJ2 | 178 | 381 | 229 | 55 | 4591 | 29 |

Hu-BLT mice were treated as described in FIG. 12. Following euthanasia, spleens were harvested, dissociated, filtered for single-cell suspension. Splenocytes were cultured at $1\times10^6$ cells/mL and supplemented with IL-2 (1000 units/mL) on day 0. Supernatants were collected at days 3, 6, and 11. Cells were then resuspended at $1\times10^6$ cells/mL and supplemented with IL-2 (1000 units/mL) for each culture timepoint. Cytokine secretion levels were determined for day 3 (Table 7A) and day 6 (Table 7B) supernatants using multiplex array analysis. Analysis was performed using a MAGPIX Luminex multiplex instrument and data was analyzed using the proprietary software (xPONENT 4.2).

TABLE 8

Measurements of oral tumors resected from hu-BLT mice

| Tumor Day 0, sac day | Weight (grams) | Day 0 total counts (million cells) |
|---|---|---|
| 1-AJ2 ctrl | N/A | N/A |
| 2-OSCSCs | 0.15 | 6.9 |
| 3-OSCSCs + NK | 0.04 | 2.1 |
| 4-OSCSCs + AJ2 | 0.071 | 5.2 |
| 5-OSCSCs + NK + AJ2 | 0.062 | 2.3 |

Hu-BLT mice were treated as described in FIG. 12. Following euthanasia, oral tumors were harvested and weights of tumors were recorded. Tumor cells were then dissociated and filtered for single-cell suspension. Cell counts were noted as shown in the table above.

TABLE 9

Human immune cell populations present in oral tumors resected from hu-BLT mice

| Tumors Day 0 CD45+ | CD3 |
|---|---|
| OSCSCs | 56.3 |
| OSCSCS + NK | 81.0 |
| OSCSCs + AJ2 | 76.5 |
| OSCSCs + NK + AJ2 | 83.7 |

Hu-BLT mice were treated as described in FIG. 12. Following euthanasia, oral tumors were harvested, dissociated, and filtered for single-cell suspension. Flow cytometry was conducted on day 0, using FITC, PE, and/or PE-Cy5 conjugated antibodies against CD45, CD3 to measure immune cell presence within the tumor. Cells were gated within the human CD45 positive population and isotype control antibodies were used as controls.

TABLE 10 in vitro growth analysis of oral tumors resected from hu-BLT mice

| Tumors (attached) | Day 7 | Day 15 |
|---|---|---|
| OSCSCs | 0.268 | 0.792 |
| OSCSCs + NK | 0.042 | 0.2 |
| OSCSCs + AJ2 | 0.216 | 0.856 |
| OSCSCs + NK + AJ2 | 0.062 | 0.3 |

Hu-BLT mice were treated as described in FIG. 12. Following euthanasia, oral tumors were harvested, dissociated and filtered for single-cell suspension. Cell for each tumor were cultured at $0.75\times10^6$ cells per well at day 0. Cells were detached and counted at day 7, and re-cultured at 10,000 cells for each condition. Cells were again detached and counted at day 15.

Example 5: Suppression of Gingival NK Cells in Precancerous and Cancerous Stages of Pancreatic Cancer in KC and BLT-Humanized Mice This Example illustrates the dynamics of natural killer (NK) cell modulation in gingivae in precancerous and cancerous stages of pancreatic and oral cancers in P48+/Cre; LSL-KRASG12D (KC) mice carrying a pancreas-specific oncogenic Kras mutation and BLT humanized mice. Wild type and KC mice fed with control diet (CD) or high-fat calorie diet (HFCD), and the pancreatic and oral tumor-bearing humanized BLT (hu-BLT) mice were used to determine precancerous and cancer induced changes in numbers and function of gingival NK cells. Increased numbers of PanIN lesions and the greatest score of inflammation in pancreas of KC mice fed with CD and HFCD co-related with significant decline in percentages of circulating and gingival NK cells, lack of DX5+NK expansion and increased secretion of IFN-γ and IL-6 after culture. At the malignant stage of pancreatic cancer, hu-BLT tumor-bearing mice had the lowest secretion of IFN-γ from cells dissociated from the gingival tissues as compared to those from non-tumor-bearing mice. Injection of NK cells into tumor-bearing mice increased IFN-γ secretion, and the secretion was similar or higher than those obtained by gingival cells from non-tumor-bearing hu-BLT control mice. The highest increase in IFN-γ secretion was observed when tumor-bearing mice were fed with AJ2 probiotic bacteria and injected with the NK cells. Along with an increase in secretion of IFN-γ, injection of NK cells in the presence and absence of feeding with AJ2 in pancreatic tumor-bearing mice increased percentages of CD45+ and CD3+ T cells in oral gingival cells. Similar results were observed with oral tumors. In conclusion, these results indicated that oral cavity may mirror systemic disease and provide a rationale for why cancer patients may be prone to suffer from diverse oral pathologies.

Materials and Methods

See Kaur et al. (2017) *Front Immunol* 8:1606, the entire contents of which are incorporated herein in their entirety by this reference, for the full description of materials and methods. In addition to materials and methods in Example 1, some exemplary methods are described below.

Conditional KRAS(G12D) Mouse Model

Figure 27:
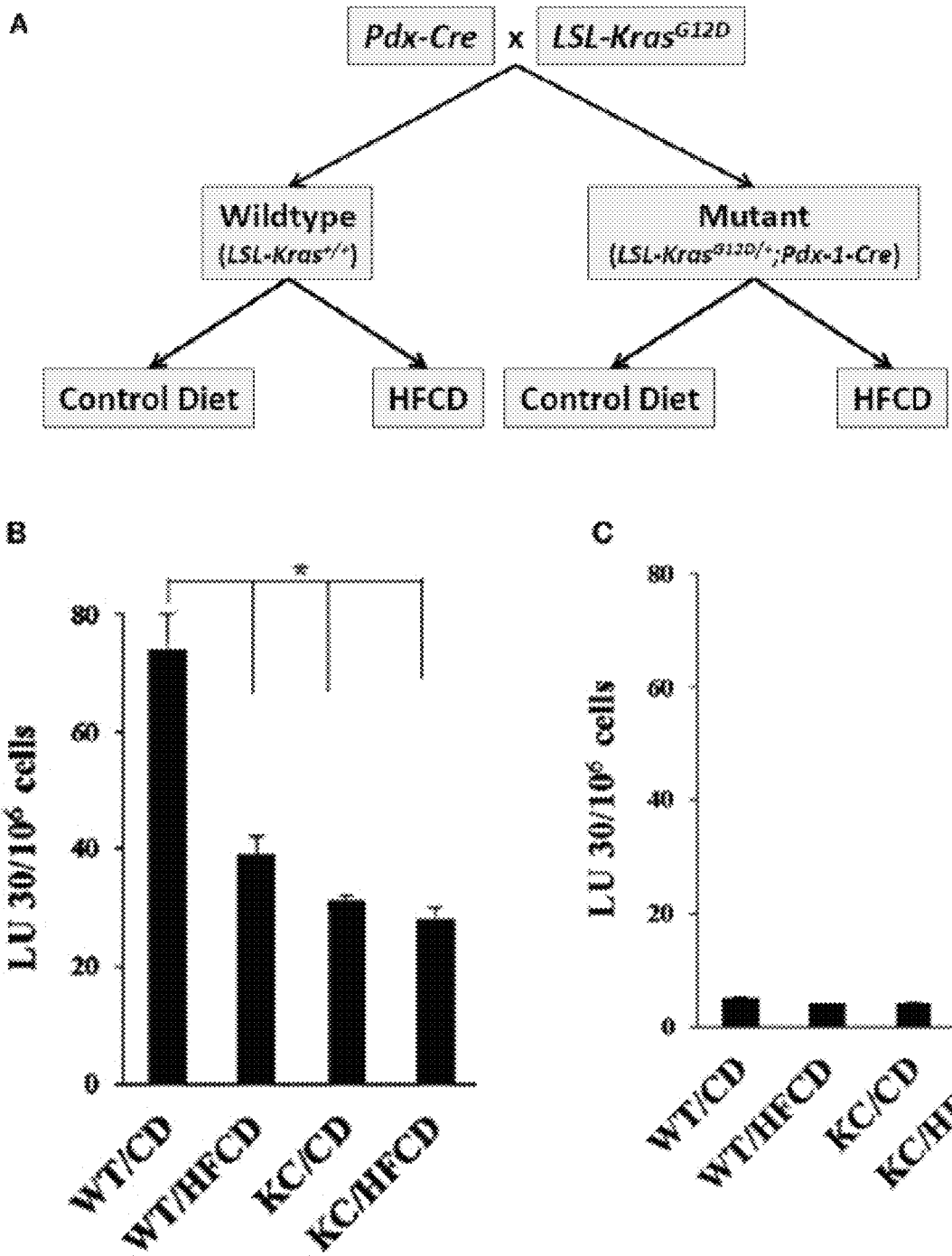
FIG. 27 shows the cytotoxicity and percentages of DX5+ NK cells in circulating PBMCs from WT mice fed with high-fat calorie diet (HFCD) and KC mice fed with control diet (CD) and HFCD as compared to WT mice fed with CD. Flow chart demonstrating group division of the WT and Conditional KC mice according to the type of diet fed is shown in this figure. Offspring of LSL-KRAS(G12D) and PDX-1-Cre mice were fed either a CD or HFCD for 3-4 months. Food intake and body weight of each animal were measured weekly (FIG. 27A). PBMCs were isolated from the peripheral blood of the mice and cultured with IL-2 (10,000 U/mL) for 7 days before they were used as effectors against $^{51}Cr$ labeled ST63 cells at various effector to target ratios in a standard 4-h $^{51}Cr$ release assay. The lytic units (LUs) $30/10^6$ cells were determined using the inverse number of cells required to lyse 30% of the ST63 cells×100 (FIG. 27B). T cells were positively selected from splenocytes and were cultured with IL-2 (1,000 U/mL) for 7 days before they were used as effectors against $^{51}Cr$ labeled ST63 cells at various effector to target ratios in a standard 4-h $^{51}Cr$ release assay. The LUs were determined as described in FIG. 27B (FIG. 27C). PBMCs were isolated from the peripheral blood of the mice and cultured with IL-2 (10,000 U/ml) for 7 days and surface expression of DX5 on CD45+ immune cells were determined (n=2) (FIG. 27D). NK cells were purified from splenocytes obtained from WT and KC mice fed with CD or HFCD, and cultured at ($1 \times 10^6$ cells/ml) before they were treated with IL-2 (10,000 U/ml) for 7 days. After incubation, NK cells were counted and equal numbers of cells from each group were cultured with $^{51}Cr$ labeled tumor cells in a standard 4-h $^{51}$Chromium release assay. The lytic units (LUs) $30/10^6$ cells were determined using the inverse number of cells required to lyse 30% of the ST63 cells×100 (FIG. 27E).

To study the effect of a high caloric diet on immune function during pancreatic cancer development, the conditional KRAS(G12D) model was used as described in Hingorani et al. (2003) *Cancer Cell* 4:437-450. After weaning, offspring of LSL-KRAS(G12D) and p48-Cre (or PDX-1-Cre) mice were fed either a high-fat calorie diet (HFCD) or a control diet (CD) for 3-4 months (FIG. 27A). Afterward, animals were euthanized and the entire pancreas, visceral adipose tissues, and other organs were harvested. Formalin-fixed, paraffin-embedded tissues were sectioned (4 μm) and stained with H&E. Sections of pancreatic tissues were histologically evaluated by a gastrointestinal pathologist for the presence and stage of murine PanIN lesions (mPanIN) as described in Hruban et al. (2001) *Am J Surg Pathol* 25:579-586. Animal studies were approved by the Chancellor's Animal Research Committee of the University of California, Los Angeles in accordance with the NIH Guide for the Care and Use of Laboratory Animals (ARC #2012-101-13A and 2011-118).

Experimental Diets

The diets were obtained from Dyets, Inc., Pennsylvania. A slightly modified AIN-76A purified rodent diet served as a CD. Compared to the CD our HFCD has increased caloric content (4,536 vs. 3,726 kcal/kg), which stems from an increase in corn oil-based fat content (1,800 vs. 450 kcal/kg). While ~12% of the total calories in the AIN-76A CD come from fat, about 40% of total caloric intake in the HFCD stems from fat. The corn oil contains about 60% omega-6 polyunsaturated fatty acids (linoleic acid), saturated fatty acids (10.8% palmitic, 2.1% stearic), mono-unsaturated fatty acids (26.5% oleic), and small amounts of omega-3 polyunsaturated fatty acids (0.6% linolenic). Importantly, the amount of sucrose, salts, and vitamins are kept identical in both diets. To compensate for the increase in corn oil, the amount of cornstarch was reduced in the HFCD accordingly. The diets were handled under low light conditions and stored at –20° C. The diets were replaced twice weekly. The stability of the fatty acids in the diets was regularly monitored by the UCLA Nutritional Biomarker and Phytochemistry Core.

Genotyping Analysis

Before randomization to the diets the presence of the $Kras^{G12D}$ and Cre allele were determined by PCR analysis of genomic DNA, as described elsewhere, obtained from tail biopsies (Funahashi et al. (2007) *Cancer Res* 67:7068-7071). Animals with both the $Kras^{G12D}$ and Cre allele were designated as mutant ($KRAS^{+/G12D}$) and animals with neither the $Kras^{G12D}$ nor the Cre allele were deemed wildtype ($KRAS^{+/+}$). At the end of the study at sacrifice, the successful excision—recombination events were confirmed by PCR by the presence of a single LoxP site in the pancrease as described in Funahashi et al. (2007).

Preparation of Single Cell Suspensions of Gingival Tissues, PBMC, and Spleen

To prepare a single-cell suspension of mouse gingival tissues for subsequent analyses, animals were sacrificed and gingival tissue from the palatal site was harvested. The gingival tissue was immediately cut into 1 mm³ pieces and placed into a digestion buffer containing 1 mg/ml collagenase II, 10 U/ml DNAse I, and 1% bovine serum albumin in DMEM, and incubated for 20 min at 37° C. oven on a 150 rpm shaker. After digestion, the samples were filtered through a 40 μm cell strainer and centrifuged at 1,500 rpm for 10 min at 4° C. The pellet was re-suspended in DMEM and cells counted. Tissue dissociation procedure as described for gingiva was followed to prepare single-cell suspensions of pancreatic tumors and oral tumors obtained from hu-BLT mice. Peripheral blood was obtained by cardiac puncture, and PBMCs were isolated as described previously (Tseng et al. (2015) *Oncotarget* 6:20002-20025 and Jewett and Bonavida (1996) *J Immunol* 156:907-915).

Results

Increased Numbers of PanIN Lesions in Pancreas in KC Mice Fed with HFCD

KC mice fed with HFCD exhibited significantly more advanced precancerous PanIN-2 and -3 lesions when compared to KC mice on CD. No invasive pancreatic ductal adenocarcinoma could be found in KC mice fed with either CD or HFCD at 3-4 months. No pancreatic neoplastic lesions were found in WT mice fed with either CD or HFCD. In addition, KC mice fed with HFCD had significantly more inflammation, acinar cell loss, and increased pancreatitis score as compared to KC mice fed with CD. The numbers of normal ducts within pancreas was much less in KC mice fed with HFCD when compared to those fed with CD, and pancreatic fibrosis was only observed in KC mice and not in WT mice.

Decreased Percentages of DX5+NK Cells and NK Cell Cytotoxicity by PBMCs of WT and KC Mice on HFCD To assess the effect of KRAS mutation and HFCD on NK cytotoxicity, PBMCs were isolated from each group of mice, and the NK cell-mediated cytotoxicity and percentages of DX5+ immune cells in circulating PBMCs were determined after culture for 7 days. ST63 tumor cells were used as target cells, ST63 were previously used as specific targets of NK cells (Regunathan et al. (2005) Blood 105:233-240). The following pattern of cytotoxicity against ST63 was observed (WT/CD>WT/HFCD>KC/CD>KC/HFCD) (FIG. 27B). CD3+ T cells isolated from spleens of each group of mice were unable to mediate cytotoxicity against ST63 target cells establishing specificity for the function of NK cells (FIG. 27C). When the percentages of DX5+ cells within CD45+ immune cells were determined following 7 days of culture, there was a consistent decrease in the percentages of DX5+ cells, which demonstrated the following pattern of expression from high to low (WT/CD>WT/HFCD> or =KC/CD>KC/HFCD) in PBMCs (FIG. 27D). NK cells purified from different groups of mice exhibited similar profiles of cytotoxicity as shown for PBMCs (FIGS. 27A and 27E).

Figure 28:
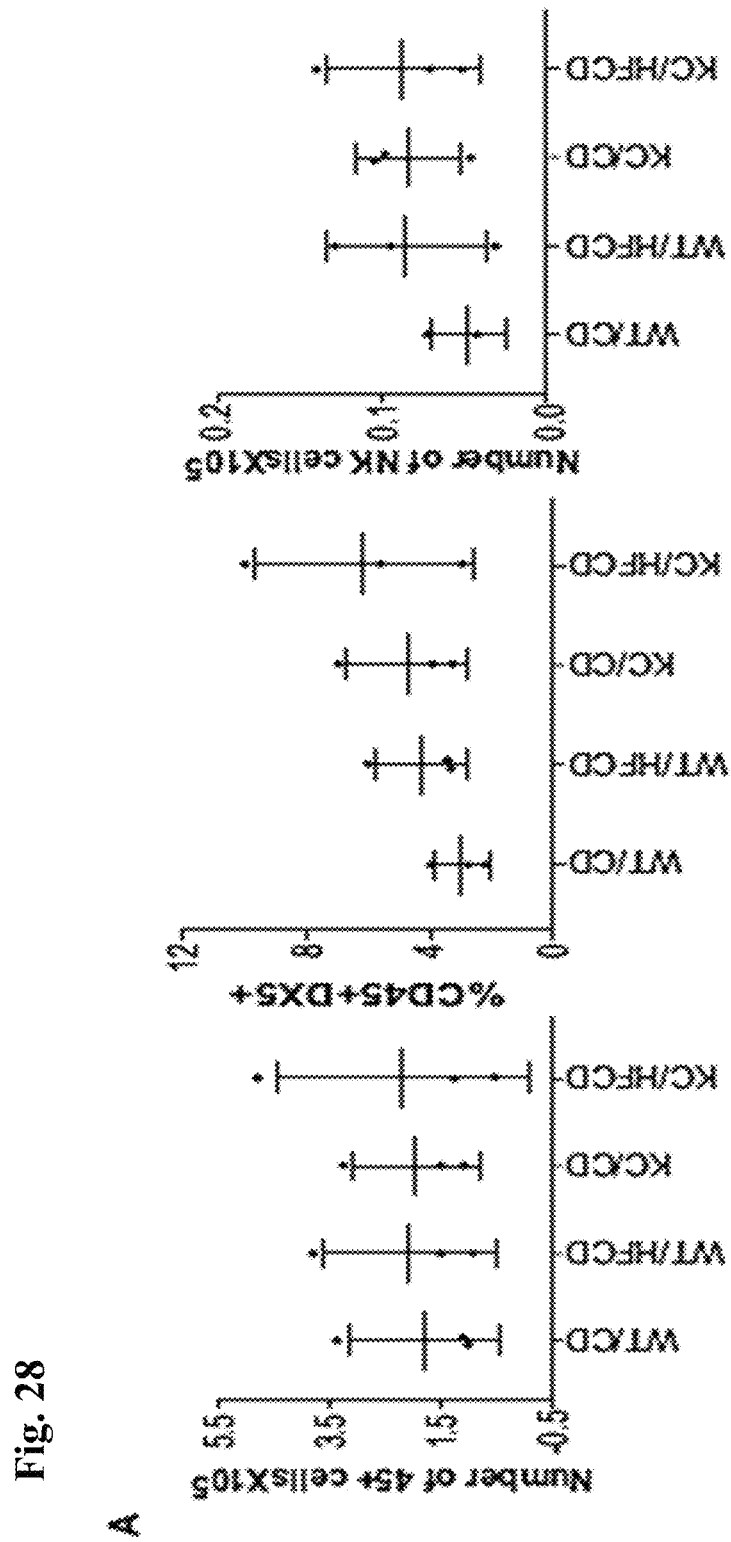
FIG. 28 shows the numbers of natural killer (NK) cells within gingiva and IFN-γ secretion in KC mice fed with CD and high-fat calorie diet after culture Gingival tissues from four groups of mice (shown in the figure) were harvested and single-cell suspensions were prepared. Percentages of CD45 and DX5 expressing immune cells within the gingival cells at the time of sacrifice were determined after staining with the respective PE- and FITC-conjugated mouse antibodies and the numbers of CD45+ immune cells, and DX5+NK cells within CD45+ immune cells were determined for each group of mice. (n=3) (FIG. 28A). Gingival cells ($5 \times 10^5$/ml) were cultured with IL-2 (10,000 U/ml) for 7 days after which the total number of cells in each were counted, the percentages of CD45 and DX5 expressing immune cells within the gingival cells were determined and the numbers of CD45+ immune cells and DX5+NK cells within CD45+ immune cells were determined for each group of mice. (n=3) (FIG. 28B). Gingival cells were cultured as described in panel (FIG. 28B) and their supernatants were harvested and IFN-γ (FIG. 28C) and IL-6 (FIG. 28D) secretion were determined using specific ELISAs.

Dynamics of NK Cell Modulation and Cytokine Secretion in the Gingiva of the WT and KC Mice Fed with CD or HFCD To evaluate the effect of KRAS mutation and high-fat calorie diet, the total numbers of CD45+ immune cells, percentage of DX5+NK cells and total numbers of NK cells in oral gingival cells of WT and KC mice were determined on day 0 (FIG. 28A) before cells were cultured for 7 days (FIG. 28B). Since it is difficult to determine the fate and number of activated NK cells in vivo in the gingival microenvironment during inflammation, possibly due to continuous recruitment of the NK cells from the circulation to the site of inflammation and/or increased proliferation and/or induction of cell death within gingival microenvironment, the cells dissociated from the gingival tissues were cultured in vitro and the fate of NK cells within the gingiva was determined. Equal numbers of cells from each group was cultured on day 0 and the total number of cells were counted on day 7 and found to be equal across different groups (FIG. 28B). On average, there were no significant differences in the numbers of CD45+ immune cells in the oral gingival tissues between the 4 groups of mice on day 0 (FIG. 28A) or day 7 of culture (FIG. 28B). Moderate increases in the DX5 expressing NK cells at time 0 (FIG. 28A) in WT mice fed with HFCD, KC mice with CD and KC mice fed with HFCD were observed when compared to WT mice fed with CD, however, the differences were not statistically significant. When the percentages of DX5+NK cells were determined after 7 days of gingiva cell culture, there was a consistent decline in the percentages of DX5+ cells within WT mice fed with HFCD or KC mice fed with CD as well as HFCD, exhibiting the following profiles (WT/CD>WT/HFCD>KC/CD>KC/HFCD) (FIG. 28B), the most severe decline was seen in KC mice fed with HFCD (FIG. 28B). When the total numbers of NK cells were determined within the populations of CD45+ gingival immune cells at time 0, similar numbers were seen in WT mice fed with HFCD or KC mice fed with CD as well as HFCD, but these three groups had moderately higher numbers of NK cells when compared to WT mice fed with CD (FIG. 28A). There was consistent decline in the numbers of NK cells within WT mice fed with HFCD or KC mice fed with CD as well as HFCD on day 7 after the cell culture, exhibiting the following profiles (WT/CD>WT/HFCD>KC/CD>KC/HFCD) (FIG. 28B). Thus, the decrease in the percentages of NK cells when gingival cells were cultured with IL-2 for 7 days was not due to the decline of total populations of CD45+ immune cells or total numbers of cells dissociated from the gingiva (FIG. 28B). By contrast to the decline of DX5+NK cells after 7 days of culture, there was an increase in IFN-γ (FIG. 28C and Table 11) and IL-6 (FIG. 28D and Table 11) secretion within the groups when compared to WT mice fed with CD and the highest secretion was obtained by immune cells cultured from the gingiva of KC mice fed with HFCD. Thus, the patterns of IFN-γ secretion within the groups were as follows (WT/CD<WT/HFCD<KC/CD<KC/HFCD). Secretion of IFN-γ is likely from both NK and T cells within the gingiva. The levels of G-CSF, MIP-1a, TNF-α, and LIX were also higher in gingival immune cells from KC mice as compared to WT mice (Table 11). The data presented here cannot rule out any contribution of minor DX5+ population of T cells in the observed results.

TABLE 11

Increased cytokines, chemokines, and growth factors and ligands secreted by the gingival cells from KC mice fed with HFCD.

| Gingiva | G-CSF Pg/ml | IL-6 Pg/ml | MCP-1 Pg/ml | MIP-1a Pg/ml | TNF-α Pg/ml | IFN-γ Pg/ml | LIX Pg/ml |
|---|---|---|---|---|---|---|---|
| WT/CD | 8 | 0 | 6 | 2 | 0 | 4 | 0 |
| WT/HFCD | 5 | 1 | 6 | 2 | 0 | 3 | 34 |
| KC/CD | 15 | 2 | 3 | 2 | 0 | 3 | ND |
| KC/HFCD | 41 | 15 | 8 | 18 | 4.2 | 22 | 59 |

Gingival tissue was harvested after the mice were sacrificed and single-cell suspensions were prepared and cultured in the presence of IL-2 (10,000 U/ml) for 7 days, after which supernatants were harvested and secretion of different cytokines, chemokines, and growth factors were determined using multiplex arrays.

Super-Charged NK Cells Restored IFN-γ and IL-8 Secretion by Gingival Immune Cells in Pancreatic Tumor-Bearing Mice Fed with and without AJ2

Figure 29:
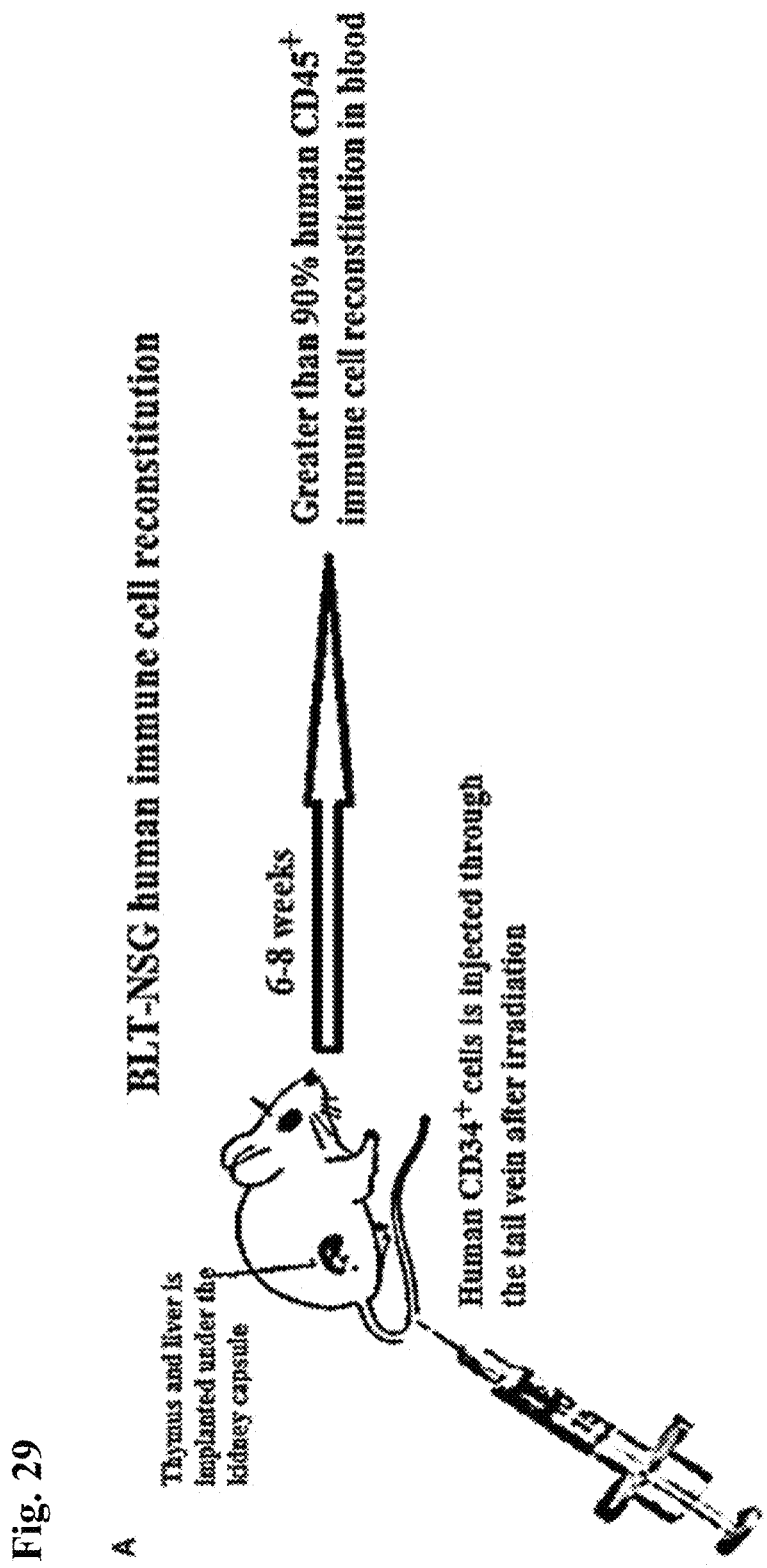
FIG. 29 shows that tail vein injection of super-charged NK cells with and without feeding with AJ2. Humanized-BLT (hu-BLT) mice were generated as shown in FIG. 29A. Reconstitution of human immune cells in blood, BM and spleen of hu-BLT mice was analyzed using human and mouse CD45 antibodies. Percentages of each of human and mouse CD45+ immune cells are shown in each respective quadrant (FIG. 29B). Gingival tissues were harvested from each group of mice and single-cell suspensions were prepared. Surface expression of human CD45, CD3, CD16, and CD56 were determined using flow cytometric analysis after staining with respective PE- and FITC-conjugated antibodies. Isotype control antibodies were used as control. One of three representative experiments is shown in the figure (FIG. 29C). Flow chart presents the experimental design using hu-BLT mice. Mice were orthotopically implanted with $1 \times 10^6$ of human oral or pancreatic tumor cells in the floor of the mouth or in the pancreas. One to two weeks after tumor implantation selected hu-BLT mice received $1.5 \times 10^6$ human or hu-BLT mice super-charged NK cells via tail vein injection. Mice were fed with AJ2 (5 billion/dose) two weeks before the tumor implantation and continued throughout the experimental period every 48 h (FIG. 29D). Four to five weeks after tumor implantation mice were sacrificed and gingival cells from tumor-bearing mice injected with NK cells and fed with and without AJ2 probiotic bacteria were dissociated and single-cell suspensions were prepared and treated with IL-2 (1,000 units/ml) and the levels of IFN-γ (n=4) were determined in supernatants harvested after 7 days of culture using specific ELISAs (FIG. 29E). The fold increase in IFN-γ secretion from the gingival cells of each mouse groups namely, control, NK injected in tumor-bearing mice or NK injected in tumor-bearing mice and fed with AJ2 was calculated based on the amounts released from cells obtained from tumor-bearing mice only (FIG. 29F). To demonstrate that autologous NK cells show the same profiles of activation as the allogeneic NK cells among groups of mice, single-cell suspensions of gingival cells from tumor-bearing hu-BLT mice injected with autologous super-charged NK cells and fed with and without AJ2 probiotic bacteria were treated with IL-2 (1,000 units/ml) and the levels of IFN-γ (n=2) from the supernatants were determined after 7 days of culture using specific ELISAs (FIG. 29G). Single-cell suspensions of gingival cells from tumor-bearing mice injected with NK cells and fed with and without AJ2 probiotic bacteria were treated with IL-2 (1,000 units/ml) and the levels of IL-8 (n=4) in the supernatants were determined after 7 days of cultures using multiplex array kit (FIG. 29H). Pancreatic tumors from tumor-bearing hu-BLT mice injected with NK cells with and without feeding with AJ2 were excised at the end of the experiment and tumor weights were determined (n=3) (FIG. 29I). Gingival cells from oral tumor-bearing mice injected with NK cells and fed with and without AJ2 were treated with IL-2 (1,000 units/ ml) and the levels of IFN-γ (n=2) were determined in supernatants after 7 days of culture using specific ELISAs (FIG. 29J).

Humanized BLT mice were reconstituted with more than 90% of human immune cells in different tissue compartments (FIGS. 29A and 29B), and had higher percentages of T cells than NK cells in oral gingiva tissue (FIG. 29C). Hu-BLT mice were fed with AJ2 probiotic bacteria 2 weeks before they were implanted with pancreatic or oral tumors in the pancreas or floor of the mouth, respectively, and after 1-2 weeks of tumor growth the super-charged NK cells were delivered through the tail vein injection and the mice were sacrificed when signs of morbidity were evident (FIG. 29D). Feeding with AJ2 continued throughout the experiment. When the gingival cells from hu-BLT mice were cultured in the presence of IL-2 and the secretion of IFN-γ and IL-8 were determined (FIGS. 29E-29J), there was a significantly lower secretion of IFN-γ from the oral gingiva cells of pancreatic tumor-bearing mice as compared to non-tumor-bearing healthy mice (FIGS. 29E-29G). Intravenous injection of human (allogeneic) super-charged NK cells (FIGS. 29E and 29F) or hu-BLT (autologous) super-charged NK cells (FIG. 29G) in pancreatic tumor-bearing mice increased IFN-γ secretion, and the levels were further increased when the mice were fed AJ2 probiotics (FIGS. 29E-29G). Similar results were obtained for the secretion of IL-8 from the gingival cells (FIG. 29H). IL-8 was tested in addition to IFN-γ to demonstrate that a chemokine in addition to a cytokine is modulated similarly in tumor-bearing hu-BLT mice in the presence and absence of NK injection with and without feeding with AJ2. Injection of super-charged NK cells in the presence and absence of feeding AJ2 resulted in substantially decreased pancreatic tumor weight (FIG. 29I).

Injection of super-charged NK cells in the presence and absence of feeding with AJ2 resulted in a similar profile of IFN-γ secretion from the gingival cells in oral tumor-bearing mice (FIG. 29J) and significant reduction in oral tumor weight in hu-BLT mice.

There was a decrease in the percentages of human CD45+ immune cells in oral tumor-bearing hu-BLT mice when compared to non-tumor-bearing healthy mice, whereas oral tumor-bearing mice injected with super-charged NK cells exhibited similar percentages of CD45+ immune cells to healthy, non-tumor bearing mice in the gingival tissues (FIG. 30A). Similarly, there was an increase in percentages of T cells in oral tumor-bearing hu-BLT mice injected with super-charged NK cells (FIGS. 30A and 30B). Oral tumor-bearing hu-BLT mice fed with AJ2 and injected with super-charged NK cells had the highest increase in the CD45+ immune cells and this increase was reflected on the increased CD3+ T cells (FIGS. 30A and 30B).

Example 6: Super-Charged NK Cells Increase Immune Cells Infiltration in the Tumors and Inhibit Growth and Metastasis of Poorly-Differentiated Pancreatic Cancer in Humanized BLT Mice Through Differentiation This Example illustrates the role of NK cells in targeting pancreatic CSCs/poorly-differentiated MiaPaCa-2 (MP2) tumors by inhibiting their aggressiveness, metastatic potential and increased susceptibility to chemotherapy. In in vivo mouse models of NSG and hu-BLT, NK cells drive selection and differentiation of pancreatic CSCs/poorly-differentiated tumors. Thus, in vivo selection and differentiation of CSCs/poorly differentiated tumors by potent NK cells which is lacking in patients is a key event in decreased aggressiveness of these tumors.

Similarly, as illustrated in previous Examples, MP2 tumors grew within 4 weeks and metastasized to both liver and lungs and killed the mice, whereas mice injected with greater numbers of PL12 generated very small tumors within 12 weeks and did not metastasize nor killed the mice. Injection of NK-supernatant-differentiated MP2 to pancreas did not exhibit growth nor metastasized to liver and lung and all mice survived at 12 weeks when the experiments were terminated. Since NK-supernatant-differentiated MP2 revert to their stem-like phenotype within 12 days of incubation after NK-supernatant removal (Tseng et al. (2015) *Oncotarget* 6:8947-8959), the reverted-MP2 cells (Diff-MP2-R) were implanted in the pancreas, resulting in increased growth and metastasis to liver within 4 weeks.

MP2 tumors were then differentiated with NK-supernatants and surgically implanted in the pancreas of hu-BLT mice. The growth dynamics and overall effect on the mice were compared to undifferentiated-MP2 tumor-bearing mice. Undifferentiated-MP2 tumors grew rapidly and formed palpable tumors in pancreas, and mice exhibited all the signs of morbidity within 4-6 weeks, and upon sacrifice at week 7, they exhibited tumors which span the entire abdomen and had enveloped spleen, stomach and a portion of intestines. When NK-supernatant-differentiated MP2 were implanted in mice, no tumors were palpable on touch or became visible at any point and the mice did not exhibit any signs of morbidity, and upon sacrifice at week 12, pancreas exhibited normal size and shape and visually no tumors could be seen.

Mice implanted with undifferentiated-MP2 tumors and injected with $1.5 \times 10^6$ super-charged NK cells with potent cytotoxic and cytokine secretion capabilities exhibited significantly smaller tumors, and no involvement of other organs or signs of morbidity could be seen. In addition, greater percentages of CD45+ immune cells in undifferentiated tumor-alone implanted mice were CD3+ T cells, whereas tumor-bearing mice which received NK cells or mice with implanted NK-differentiated tumor exhibited CD3+ T cells proportions closer to the hu-BLT control mice. About 2.0-2.7 fold more CD45+ immune cells or CD16+ CD56+NK cells within CD45+ immune cells were seen in either NK-injected tumor-bearing mice or NK-differentiated tumor implanted mice or in the control non-tumor implanted mice when compared to undifferentiated tumor-bearing mice.

When mice were fed AJ2 1-2 weeks before tumor implantation and injected with super-charged NK cells, no tumors were palpable in either NK or NK injected/AJ2 fed mice, and tumor weights remained substantially low, in contrast to the large tumors which were obtained in non-NK injected mice. Serum from NK-injected or NK injected/AJ2 fed tumor-bearing mice exhibited 2.73 and 4.8-fold more IFN-γ respectively when compared to tumor-bearing mice. Similarly, injection of NK-differentiated MP2 tumors did not demonstrate visible tumors, and blocking of MP2 differentiation with anti-IFN-γ and anti-TNF-α antibodies resulted in the formation of the large tumors. Both autologous and allogeneic NK cells were effective in blocking tumor growth and no significant differences could be found between the two.

When tumors were dissociated and cultured from mice that did not receive NK injection, tumors grew rapidly, whereas those which were injected with autologous or allogeneic NK cells did not grow or grew very slowly. Similarly, NK-differentiated tumors did not grow and blocking differentiation with anti-IFN-γ and anti-TNF-α antibodies restored tumor growth, although not to the levels which were obtained when tumors were implanted in the absence of NK injection. Tumor growth after dissociation was less in mice which were fed AJ2 and injected with NK cells in comparison to NK alone injected mice, and both were substantially less than those which only received implantation of the MP2 tumors in the absence of NK. There were 18-22 fold more infiltrating hCD45+ immune cells in tumors cultured from mice injected with tumors and NK cells in comparison to tumor-alone injected mice. The majority of CD45+ immune cells expressed CD94, CD56, NKG2D and DNAM surface receptors.

When pancreas was dissociated and the same numbers of cells were cultured with IL-2 from each group, a significant decrease in the secreted IFN-γ could be observed in mice which were implanted with stem-like/undifferentiated-MP2 tumors, as compared to control mice with no tumors. Injection of NK cells to tumor-bearing mice restored the secretion of IFN-γ and the levels exceeded those seen with the control mice with no tumors. Implantation of NK-differentiated MP2 tumors did not result in inhibition of IFN-γ and the amounts were same level those obtained from control mice with no tumors. Feeding AJ2 and injecting NK cells had the highest induction of IFN-γ which exceeded the levels seen in all other groups. In contrast IL-6 secretion was elevated in tumor-bearing mice and it substantially lower in all the other groups of mice.

The expression of B7H1 (PD-L1), MHC-class I and CD54 were significantly higher on MP2 tumors dissociated from NK-injected mice when compared to those obtained from MP2-alone implanted mice. Moreover, similar to in vitro experiments, MP2 tumors from NK-injected mice exhibited substantially decreased susceptibility to NK cell-mediated killing whereas those obtained from no NK-injected mice remained significantly more susceptible. When differentiation of tumors was blocked with antibodies to anti-IFN-γ and anti-TNF-α, increased susceptibility to NK cell-mediated cytotoxicity was restored.

Loss of NK cytotoxicity and/or secretion of IFN-γ in tumor-bearing mice within all tissue compartments, and restoration of both cytotoxicity and IFN-γ secretion with the injection of NK cells and/or feeding AJ2. Tumor-bearing mice PBMCs, like pancreatic cancer patients' PBMCs and NK cells, had significantly less PBMCs-mediated and NK-mediated cytotoxicity and exhibited decreased IFN-γ secretion from PBMCs and other tissue compartments. When PBMCs, splenocytes, enriched-NK cells from splenocytes, CD3+ T cells from splenocytes and BM-derived immune cells were assessed for NK cytotoxicity and/or secretion of IFN-γ, those from tumor-bearing mice had much lower cytotoxicity and/or secretion of IFN-γ in all tissue compartments (similar to cancer patients PBMCs, NK cells and T cells) in comparison to control mice without tumor, or those injected with NK cells, or those implanted with the NK-differentiated tumors. Blocking tumor differentiation with anti-IFN-γ and anti-TNF-α antibodies decreased IFN-γ secretion to the levels which were obtained by undifferentiated tumors. Injection of anti-PD1 in combination with NK cells similar to feeding AJ2 elevated secretion of IFN-γ in all tissue compartments.

The stage of differentiation in pancreatic tumors correlates with susceptibility to NK cell-mediated cytotoxicity. Among six pancreatic tumors at different stages of differentiation, stem-like/poorly-differentiated MP2 tumors expressed higher CD44 and lower expression of MHC-class I and CD54, and were highly susceptible to NK cell-mediated cytotoxicity whereas well-differentiated PL12 tumors had lower CD44 but higher CD54 and MHC-class I, and they were relatively resistant to NK cell-mediated cytotoxicity.

Resistance of NK-differentiated MP2 tumors to NK cell-mediated cytotoxicity is mediated by the combination of IFN-γ and TNF-α secreted from the NK cells. NK cells-mediated differentiation of MP2 tumors through the actions of IFN-γ and TNF-α.

NAC, CDDP and Paclitaxel induce significant cell death in NK-differentiated MP2 tumors.

Differentiation of MP2 with NK-supernatants resulted in a significant susceptibility to CDDP and Paclitaxel mediated cell death and blocking NK-supernatant mediated differentiation of MP2 tumors with anti-IFN-γ and anti-TNF-α antibodies substantially decreased the cell death induced by either CDDP or Paclitaxel. The addition of NAC to either poorly-differentiated MP2 in general had lower/slight effect on cell death, however, when added to well-differentiated PL12 or Capan it induced greater levels of cell death.

Monocytes or osteoclasts from tumor-bearing mice injected with NK cells or implanted with NK-differentiated MP2 tumors triggered significantly more IFN-γ from NK cells when compared to those of tumor-alone implanted mice. When purified NK cells from hu-BLT were cultured with autologous monocytes purified from BM, or allogeneic healthy NK cells cultured with hu-BLT osteoclasts and the levels of NK expansion, cytotoxicity, IFN-γ secretion by the NK cells were assessed, those cultured with monocytes or osteoclasts from mice implanted with tumor and injected with NK cells or implanted with NK-differentiated tumors had significantly higher expansion and function as compared to NK+monocyte or NK+osteoclast cultures from tumor-bearing mice in the absence of NK or NK-differentiated tumors. Similar results were obtained when osteoclasts from pancreatic-cancer patients and healthy controls were cultured with allogeneic healthy NK cells. Osteoclasts from cancer patients were less able to expand NK cells, mediate cytotoxicity or secrete IFN-γ when compared to osteoclasts from healthy individuals. When examining the surface receptor expression on cancer-patient and healthy individuals' osteoclasts, decreased expression of MHC-class I, CD54, KLRG1, KIR2/KIR3 and MICAS could be seen on patient OCs as compared to healthy OCs.

In addition, even when the same amounts of IFN-γ from the supernatants of NK cells were used to differentiate MP2 tumors, those from patient NK cells differentiated-MP2 tumors much less than NK-supernatants from healthy individuals. NK-supernatants from patients elevated MHC-class I moderately and induced only 35% resistance of MP2 tumors to NK-mediated cytotoxicity, whereas NK-supernatants from healthy individuals elevated MHC-class I substantially and induced 78% resistance of MP2 against NK-mediated cytotoxicity. Less suppression was observed by supernatants from patient T cells in differentiation of MP2 tumors than NK cells when compared to healthy individuals' T cells.

Example 7: The Potential Therapeutic Use of NK Cells and AJ2 Composition

Cytokines, primarily IFN-γ and TNF-α, secreted by the NK cells are responsible for the increase in differentiation antigens MHC class I, CD54, and B7H1 and decrease in CD44 resulting in the differentiation of both healthy and transformed stem cells, including OSCSCs. This study demonstrates that probiotic bacteria also induce significant split anergy in NK cells, thus resulting in increased cytokine secretion.

sAJ2 is a combination of 8 strains of probiotic bacteria selected for their ability to induce synergistic secretion of IFN-γ when added to IL-2 or IL-2+anti-CD16 mAb treated NK cells (Bui et al. (2015) *Front Immunol,* 6:576). This combination of bacterial strains was selected to provide bacterial diversity as well as for its optimal induction of pro- and anti-inflammatory cytokines and growth factors by the NK cells.

Although there was no significant difference observed in the NK cell cytotoxic levels of sAJ2, significantly augmented cytokine secretion was observed in NK cells treated with sAJ2 probiotic, suggesting a dissociation between cytotoxicity and cytokine secretion functions of NK cells affected by bacteria (FIGS. 1 and 2). Based on this project, sAJ2 bacteria treated split anergized NK cell supernatants also induced greater differentiation and resistance of OSCSCs to NK cell mediated cytotoxicity (another indication of differentiation, since NK cells tend to target stem/stem-like cells and not their more differentiated counterparts) (FIGS. 3 and 4). This differentiation of OSCSCs induced by split anergized NK cells treated with sAJ2 is significantly mediated through the cytokine secretion of IFN-γ and/or TNF-α (FIGS. 3-7). Thus, sAJ2 probiotic bacteria treatment of NK cells induces cytokine secretion, further resulting in tumor differentiation, and reduced tumor growth.

Applicants discovered that using osteoclasts as feeder cells in combination with IL-2+ anti-CD16 mAb+sAJ2 is the best strategy to expand large numbers of super-charged NK cells with a significant capability to target cancer stem cells when compared to a number of previous strategies (Table 2 and FIG. 11). Applicants achieved about 21,000-132,000 fold expansion on day 20, and 0.3-5.1 million on day 31, with 17-21 population doublings within 4 weeks—a much higher rate than any previously reported NK expansion method. Although cytotoxic function of expanded NK cells across studies are difficult to compare due to different types of targets used for assessment, our strategy provides expanded NK cells (which maintain their purity for a long period of time) with significant functionality to target and lyse cancer stem cells, in addition to providing larger amounts of IFN-γ secretion (FIGS. 8-10).

Since both autologous and allogeneic NK cells can be expanded using our lab's NK expansion protocol, our recent findings show promise in being translated into a therapeutic immunotherapy for cancer patients. Thus, Applicants' in vivo studies indicate that NK cells are the main immune effectors that select and differentiate CSCs, resulting in inhibition of tumor growth and resolution of chronic inflammation during disease progression. CSCs differentiated by NK cells become sensitive targets for chemotherapeutic and radio therapeutic strategies. Non-HLA matched oral, pancreatic and melanoma CSCs are able to form substantial tumors in BLT humanized mice that have a fully reconstituted human immune system. In addition, major human immune subsets including NK cells, T cells, B cells and monocytes were present in bone marrow (Table 3), blood (Table 4), spleen (Table 6), and infiltrated tumor microenvironment (Table 9). Intravenous injection of expanded NK cells inhibited tumor growth of OSCSCs by differentiating CSCs in humanized mice (Tables 8 and 10, FIG. 24-26). In addition, tumors differentiated through NK immunotherapy expressed higher levels of MHC-I (FIG. 25), were more resistant to NK cell mediated cytotoxicity (FIG. 26) and grew at a much slower rate (Tables 8 and 10, FIG. 24). These results clearly showed that NK cell induced tumor differentiation is important in the limitation of tumor growth and aggressiveness. It also showed that probiotic bacteria, combined with NK activated cytokines and osteoclasts as feeder cells provide a condition for NK cells to promote tumor differentiation.

Figure 16:
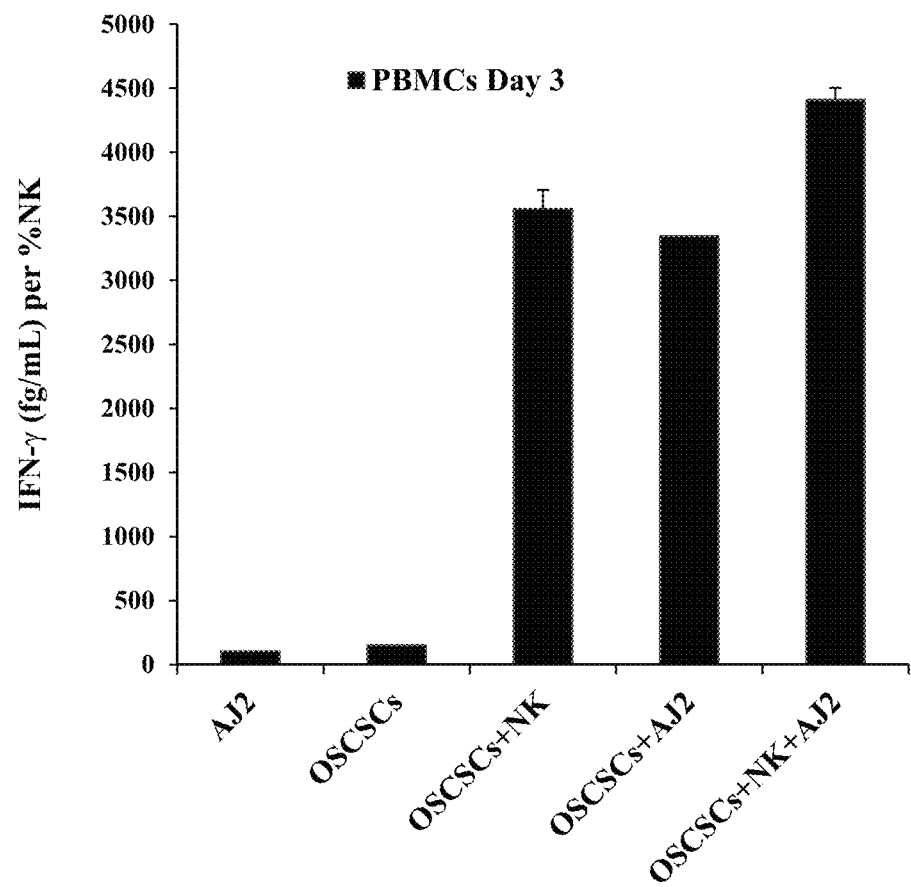
FIG. 16 shows that IFN-γ secretion of IL-2 activated PBMCs from hu-BLT mice. Hu-BLT mice were treated as described in FIG. 12. Following euthanasia, blood was collected from the mice and PBMCs were separated using Ficoll-Hypaque centrifugation. PBMCs were cultured at $0.4\times10^6$ cells/mL and supplemented with IL-2 (1000 units/mL) on day 0. Supernatants were collected at day 3 and cells were again resuspended at $0.4\times10^6$ cells/mL and supplemented with IL-2 (1000 units/mL). IFN-γ secretion levels were determined for supernatants using human IFN-γ ELISA.

The use of NK immunotherapy supplemented with AJ2 also enhanced the function of NK cells in various immune tissue compartments. Various tissue compartments of hu-BLT mice receiving NK immunotherapy secreted high levels of IFN-γ and IL-10 (FIGS. 14B, 16, 18, 19, 21-23 and Table 7). Meanwhile, with NK immunotherapy in combination with AJ2 supplementation, there was a significant increase in cytokine secretion levels as compared to the NK immunotherapy alone (FIGS. 13, 14, 18-21 and Tables 5 and 7). Mice receiving NK immunotherapy treatment had significantly improved cytotoxic function compared to tumor bearing alone condition, which demonstrated significantly reduced cytotoxic function in both cultured PBMCs (FIG. 15) and splenocytes (FIG. 17). Similar to the tumor alone condition, NK cells of cancer patients also show lack of function both in terms of cytokine secretion and cytotoxicity. Meanwhile, similar to the hu-BLT healthy control group, healthy human PBMCs, when activated with IL-2 alone, demonstrate low cytokine secretion and a high level of cytotoxicity (FIGS. 15 and 16). The tumor-bearing, probiotic supplementation control group exhibits the split anergized phenotype, in which cytotoxicity is reduced, but there is augmented IFN-γ secretion (FIGS. 15 and 16). Meanwhile, mice that receive NK immunotherapy following tumor injections demonstrate both cytotoxic as well as cytokine secretory functions (FIGS. 15 and 16). This demonstrates the continued in vivo potency of the ex vivo expanded NK cells and their ability to select and differentiate cancer stem-like tumors in BLT humanized mouse model in combination with probiotic supplementation.

As indicated above, feeding AJ2 to tumor-bearing hu-BLT mice injected with super-charged. NK cells increased both the levels of CD45+ immune cells and CD3+ T cells in gingiva. When adjusted based on percentage of CD3+ T cells, the levels of IFN-γ secretion per percentage of T cells from tumor-bearing mice fed with AJ2 and injected with NK cells were similar to non-tumor-bearing healthy mice (data not shown), therefore, feeding AJ2 not only increases the recruitment of immune cells to the gingiva but it also restores the amount of secreted UN-7 to the levels seen by gingival cells of healthy mice. Since oral cavity is an accessible route, it may be used to predict systemic tumor burden in pancreatic cancer. Presently, with the existing technologies, it is very difficult to determine the course of disease in pancreatic cancer, therefore, by the use of either saliva or cells from gingival tissues one may be able to predict disease activity and tailor treatment strategies to better target the tumors. In addition, loss of NK function within gingiva may be a predictor of oral diseases. Moreover, the data presented in this paper clearly demonstrate that both genetic and life style factors are likely to contribute to tumorigenesis as well as suppression of NK cell function in gingiva.

Expanded NK cells selected and differentiated CSCs both in in vitro and in vivo systems. The use of NK immunotherapy supplemented with AJ2 induced higher percentages of NK cells and T cells, and enhanced the functions of NK cells, especially the cytokine secretion ability. NK immunotherapy selected and differentiated oral tumors in the presence of probiotic bacteria. These findings provided a vital translational research foundation. Applicants discovered remarkable effects of NK immunotherapy in humanized mice, most notably its ability to prevent tumor growth and differentiate tumors. In view of clinical settings, e.g., through Phase I clinical trials testing the effects of NK immunotherapy, the use of probiotic supplementation includes an adjuvant therapy to cancer treatment, or as a cancer preventative measure, optionally in combination with chemotherapy or immunotherapy. NK cells, due to their unique functional ability to target, kill and differentiate CSCs, which are capable of metastasis and cancer regeneration, have therapeutic uses against cancer relapse in patients. This breakthrough method of NK expansion facilitates and optimizes adoptive NK immunotherapy.

REFERENCES

1. Palmer, J. M., et al., *Clinical relevance of natural killer cells following hematopoietic stem cell transplantation.* J Cancer, 2013. 4(1): p. 25-35.
2. Fildes, J. E., N. Yonan, and C. T. Leonard, *Natural killer cells and lung transplantation, roles in rejection, infection, and tolerance.* Transpl Immunol, 2008. 19(1): p. 1-11.
3. Farag, S. S. and M. A. Caligiuri, *Human natural killer cell development and biology.* Blood Rev, 2006. 20(3): p. 123-37.
4. Trinchieri, G., *Biology of natural killer cells.* Adv Immunol, 1989. 47: p. 187-376.
5. Lanier, L. L., *NK cell recognition.* Annu Rev Immunol, 2005. 23: p. 225-74.
6. Tseng, H. C., et al., *Increased lysis of stem cells but not their differentiated cells by natural killer cells; de-differentiation or reprogramming activates NK cells.* PLoS One, 2010. 5(7): p. e11590.

7. Jewett, A., et al., *Natural killer cells as effectors of selection and differentiation of stem cells: role in resolution of inflammation.* J Immunotoxicol, 2014. 11(4): p. 297-307.
8. Tseng, H. C., et al., *Induction of Split Anergy Conditions Natural Killer Cells to Promote Differentiation of Stem Cells through Cell-Cell Contact and Secreted Factors.* Front Immunol, 2014. 5: p. 269.
9. Bui, V. T., et al., *Augmented IFN-gamma and TNF-alpha Induced by Probiotic Bacteria in NK Cells Mediate Differentiation of Stem-Like Tumors Leading to Inhibition of Tumor Growth and Reduction in Inflammatory Cytokine Release; Regulation by IL-10.* Front Immunol, 2015. 6: p. 576.
10. Moretta, L., et al., *Human natural killer cells: origin, receptors, function, and clinical applications.* Int Arch Allergy Immunol, 2014. 164(4): p. 253-64.
11. Larsen, S. K., Y. Gao, and P. H. Basse, *NK cells in the tumor microenvironment.* Crit Rev Oncog, 2014. 19(1-2): p. 91-10$^5$.
12. Burke, S., et al., *New views on natural killer cell-based immunotherapy for melanoma treatment.* Trends Immunol, 2010. 31(9): p. 339-45.
13. Imai, K., et al., *Natural cytotoxic activity of peripheral-blood lymphocytes and cancer incidence: an 11-year follow-up study of a general population.* Lancet, 2000. 356(9244): p. 1795-9.
14. Hersey, P., et al., *Low natural-killer-cell activity in familial melanoma patients and their relatives.* Br J Cancer, 1979. 40(1): p. 113-22.
15. Castriconi, R., et al., *Transforming growth factor beta 1 inhibits expression of NKp30 and NKG2D receptors: consequences for the NK-mediated killing of dendritic cells.* Proc Natl Acad Sci USA, 2003. 100(7): p. 4120-5.
16. Balsamo, M., et al., *Melanoma-associated fibroblasts modulate NK cell phenotype and antitumor cytotoxicity.* Proc Natl Acad Sci USA, 2009. 10$^6$(49): p. 20847-52.
17. Gubbels, J. A., et al., *MUC16 provides immune protection by inhibiting synapse formation between NK and ovarian tumor cells.* Mol Cancer, 2010. 9: p. 11.
18. Pietra, G., et al., *Melanoma cells inhibit natural killer cell function by modulating the expression of activating receptors and cytolytic activity.* Cancer Res, 2012. 72(6): p. 1407-15.
19. Bruno, A., et al., *A think tank of TINK/TANKs: tumor-infiltrating/tumor-associated natural killer cells in tumor progression and angiogenesis.* J Natl Cancer Inst, 2014. 106(8): p. dju200.
20. Gallois, A., et al., *Reversal of natural killer cell exhaustion by TIM-3 blockade.* Oncoimmunology, 2014. 3(12): p. e946365.
21. Mirjacic Martinovic, K. M., et al., *Decreased expression of NKG2D, NKp46, DNAM-1 receptors, and intracellular perforin and STAT-1 effector molecules in NK cells and their dim and bright subsets in metastatic melanoma patients.* Melanoma Res, 2014. 24(4): p. 295-304.
22. Vitale, M., et al., *Effect of tumor cells and tumor microenvironment on NK-cell function.* Eur J Immunol, 2014. 44(6): p. 1582-92.
23. Magister, S., et al., *Regulation of cathepsins S and L by cystatin F during maturation of dendritic cells.* Eur J Cell Biol, 2012. 91(5): p. 391-401.
24. Tseng, H. C., N. Cacalano, and A. Jewett, *Split anergized Natural Killer cells halt inflammation by inducing stem cell differentiation, resistance to NK cell cytotoxicity and prevention of cytokine and chemokine secretion.* Oncotarget, 2015. 6(11): p. 8947-59.
25. Metchnikoff, E., *Essais optimistes.* 1907, Paris: A. Maloine. iii, 438 p.
26. Fuller, R., *PROBIOTICS IN MAN AND ANIMALS.* Journal of Applied Bacteriology, 1989. 66(5): p. 365-378.
27. Matsuzaki, T. and J. Chin, *Modulating immune responses with probiotic bacteria.* Immunology and cell biology, 2000. 78(1): p. 67-73.
28. Gill, H. S., et al., *Enhancement of immunity in the elderly by dietary supplementation with the probiotic Bifidobacterium lactis HN019.* The American journal of clinical nutrition, 2001. 74(6): p. 833-9.
29. Perdigon, G., et al., *Systemic augmentation of the immune response in mice by feeding fermented milks with Lactobacillus casei and Lactobacillus acidophilus.* Immunology, 1988. 63(1): p. 17-23.
30. Isolauri, E., et al., *Probiotics: effects on immunity.* The American journal of clinical nutrition, 2001. 73(2 Suppl): p. 444S-450S.
31. Park, J. H., et al., *Encapsulated Bifidobacterium bifidum potentiates intestinal IgA production.* Cellular immunology, 2002. 219(1): p. 22-7.
32. Fukushima, Y., et al., *Effect of a probiotic formula on intestinal immunoglobulin A production in healthy children.* International journal of food microbiology, 1998. 42(1-2): p. 39-44.
33. Rautava, S., H. Arvilommi, and E. Isolauri, *Specific probiotics in enhancing maturation of IgA responses in formula-fed infants.* Pediatric research, 2006. 60(2): p. 221-4.
34. Ustunol, Z. and J. J. Pestka, *Probiotics in health: Their immunomodulatory potential against allergic disorders.* Journal of Animal Science, 2004. 82: p. 274-274.
35. Fuccio, L., et al., *Effects of Probiotics for the Prevention and Treatment of Radiation-induced Diarrhea.* Journal of Clinical Gastroenterology, 2009. 43(6): p. 506-513.
36. Ouwehand, A. C., *Antiallergic effects of probiotics.* The Journal of nutrition, 2007. 137(3 Suppl 2): p. 794S-7S.
37. Fotiadis, C. I., et al., *Role of probiotics, probiotics and synbiotics in chemoprevention for colorectal cancer.* World Journal of Gastroenterology, 2008. 14(42): p. 6453-6457.
38. Ozdemir, O., *Various effects of different probiotic strains in allergic disorders: an update from laboratory and clinical data.* Clinical and experimental immunology, 2010. 160(3): p. 295-304.
39. Dongarra, M. L., et al., *Mucosal immunology and probiotics.* Current allergy and asthma reports, 2013. 13(1): p. 19-26.
40. Tseng, H. C., et al., *Bisphosphonate-induced differential modulation of immune cell function in gingiva and bone marrow in vivo: role in osteoclast-mediated NK cell activation.* Oncotarget, 2015. 6(24): p. 20002-25.
41. SUDA, T., N. TAKAHASHI, and T. J. MARTIN, *Modulation of Osteoclast Differentiation.* Endocrine Reviews, 1992. 13(1): p. 66-80.
42. Tanaka, Y., S. Nakayamada, and Y. Okada, *Osteoblasts and osteoclasts in bone remodeling and inflammation.* Curr Drug Targets Inflamm Allergy, 2005. 4(3): p. 325-8.
43. Feng, S., et al., *IL-15-activated NK cells kill autologous osteoclasts via LFA-1, DNAM-1 and TRAIL, and inhibit osteoclast-mediated bone erosion in vitro.* Immunology, 2015.
44. Lanier, L. L., *NK cell receptors.* Annu Rev Immunol, 1998. 16: p. 359-93.
45. London, L., B. Perussia, and G. Trinchieri, *Induction of proliferation in vitro of resting human natural killer cells: IL 2 induces into cell cycle most peripheral blood NK* cells, but only a minor subset of low density T cells. J Immunol, 1986. 137(12): p. 3845-54.
46. Perussia, B., et al., *Preferential proliferation of natural killer cells among peripheral blood mononuclear cells cocultured with B lymphoblastoid cell lines.* Nat Immun Cell Growth Regul, 1987. 6(4): p. 171-88.
47. Igarashi, T., et al., *Enhanced cytotoxicity of allogeneic NK cells with killer immunoglobulin-like receptor ligand incompatibility against melanoma and renal cell carcinoma cells.* Blood, 2004. 104(1): p. 170-7.
48. Rabinowich, H., et al., *Increased proliferation, lytic activity, and purity of human natural killer cells cocultured with mitogen-activated feeder cells.* Cell Immunol, 1991. 135(2): p. 454-70.
49. Srivastava, S., A. Lundqvist, and R. W. Childs, *Natural killer cell immunotherapy for cancer: a new hope.* Cytotherapy, 2008. 10(8): p. 775-83.
50. Miller, J. S., et al., *Role of monocytes in the expansion of human activated natural killer cells.* Blood, 1992. 80(9): p. 2221-9.
51. Gras Navarro, A., A. Bjorklund, and M. Chekenya, *Therapeutic potential and challenges of Natural killer cells in treatment of solid tumors.* Frontiers in Immunology, 2015. 6.
52. Fujisaki, H., et al., *Expansion of highly cytotoxic human natural killer cells for cancer cell therapy.* Cancer Res, 2009. 69(9): p. 4010-7.
53. Alici, E., et al., *Autologous antitumor activity by NK cells expanded from myeloma patients using GMP-compliant components.* Blood, 2008. 111(6): p. 3155-62.
54. Carlens, S., et al., *A new method for in vitro expansion of cytotoxic human CD3-CD56+ natural killer cells.* Hum Immunol, 2001. 62(10): p. 1092-8.
55. Berg, M., et al., *Clinical-grade ex vivo-expanded human natural killer cells up-regulate activating receptors and death receptor ligands and have enhanced cytolytic activity against tumor cells.* Cytotherapy, 2009. 11(3): p. 341-55.
56. Trinchieri, G., et al., *Response of resting human peripheral blood natural killer cells to interleukin 2.* J Exp Med, 1984. 160(4): p. 1147-69.
57. Garg, T. K., et al., *Highly activated and expanded natural killer cells for multiple myeloma immunotherapy.* Haematologica, 2012. 97(9): p. 1348-56.
58. Shah, N., et al., *Antigen presenting cell-mediated expansion of human umbilical cord blood yields log-scale expansion of natural killer cells with anti-myeloma activity.* PLoS One, 2013. 8(10): p. e76781.
59. Robertson, M. J., et al., *Costimulatory signals are required for optimal proliferation of human natural killer cells.* J Immunol, 1993. 150(5): p. 1705-14.
60. Lanier, L. L., et al., *Interleukin 2 activation of natural killer cells rapidly induces the expression and phosphorylation of the Leu-23 activation antigen.* J Exp Med, 1988. 167(5): p. 1572-85.
61. Imai, C., S. Iwamoto, and D. Campana, *Genetic modification of primary natural killer cells overcomes inhibitory signals and induces specific killing of leukemic cells.* Blood, 2005. 106(1): p. 376-83.
62. Lapteva, N., et al., *Large-scale ex vivo expansion and characterization of natural killer cells for clinical applications.* Cytotherapy, 2012. 14(9): p. 1131-43.
63. Shultz, L. D., et al., *Human cancer growth and therapy in immunodeficient mouse models.* Cold Spring Harb Protoc, 2014. 2014(7): p. 694-708.
64. Kozlowska, A. K., et al., *Adoptive transfer of osteoclast-expanded natural killer cells for immunotherapy targeting cancer stem-like cells in humanized mice.* Cancer Immunology, Immunotherapy, 2016. 65(7): p. 835-845.
65. McDermott, S. P., et al., *Comparison of human cord blood engraftment between immunocompromised mouse strains.* Blood, 2010. 116(2): p. 193-200.
66. Brehm, M. A., et al., *Parameters for establishing humanized mouse models to study human immunity: analysis of human hematopoietic stem cell engraftment in three immunodeficient strains of mice bearing the IL2rgamma (null) mutation.* Clin Immunol, 2010. 135(1): p. 84-98.
67. Shultz, L. D., F. Ishikawa, and D. L. Greiner, *Humanized mice in translational biomedical research.* Nat Rev Immunol, 2007. 7(2): p. 118-30.
68. Ito, A., et al., *Defucosylated anti-CCR4 monoclonal antibody exercises potent ADCC-mediated antitumor effect in the novel tumor-bearing humanized NOD/Shi-scid, IL-2Rgamma(null) mouse model.* Cancer Immunol Immunother, 2009. 58(8): p. 1195-206.
69. King, M. A., et al., *Human peripheral blood leucocyte non-obese diabetic-severe combined immunodeficiency interleukin-2 receptor gamma chain gene mouse model of xenogeneic graft-versus-host-like disease and the role of host major histocompatibility complex.* Clin Exp Immunol, 2009. 157(1): p. 104-18.
70. Shultz, L. D., et al., *Humanized mice for immune system investigation: progress, promise and challenges.* Nat Rev Immunol, 2012. 12(11): p. 786-98.
71. Shimizu, S., et al., *A highly efficient short hairpin RNA potently down-regulates CCR5 expression in systemic lymphoid organs in the hu BLT mouse model.* Blood, 2010. 115(8): p. 1534-44.
72. Vatakis, D. N., et al., *Using the BLT humanized mouse as a stem cell based gene therapy tumor model.* J Vis Exp, 2012(70): p. e4181.
73. Onoe, T., et al., *Human natural regulatory T cell development, suppressive function, and postthymic maturation in a humanized mouse model.* J Immunol, 2011. 187(7): p. 3895-903.
74. Stoddart, C. A., et al., *Superior human leukocyte reconstitution and susceptibility to vaginal HIV transmission in humanized NOD-scid IL-2Rgamma(−/−) (NSG) BLT mice.* Virology, 2011. 417(1): p. 154-60.
75. Ito, M., et al., *NOD/SCID/gamma(c)(null) mouse: an excellent recipient mouse model for engraftment of human cells.* Blood, 2002. 100(9): p. 3175-82.
76. Traggiai, E., et al., *Development of a human adaptive immune system in cord blood cell-transplanted mice.* Science, 2004. 304(5667): p. 104-7.
77. Ishikawa, F., et al., *Development of functional human blood and immune systems in NOD/SCID/IL2 receptor {gamma} chain(null) mice.* Blood, 2005. 10$^6$(5): p. 1565-73.
78. Strowig, T., et al., *Human NK cells of mice with reconstituted human immune system components require preactivation to acquire functional competence.* Blood, 2010. 116(20): p. 4158-67.
79. Olesen, R., et al., *Immune reconstitution of the female reproductive tract of humanized BLT mice and their susceptibility to human immunodeficiency virus infection.* J Reprod Immunol, 2011. 88(2): p. 195-203.
80. Denton, P. W., et al., *Generation of HIV latency in humanized BLT mice.* J Virol, 2012. 86(1): p. 630-4.
81. Vatakis, D. N., et al., *Antitumor activity from antigen-specific CD8 T cells generated in vivo from genetically engineered human hematopoietic stem cells.* Proc Natl Acad Sci USA, 2011. 108(51): p. E1408-16.

82. Deng, X., et al., *Synergistic cytotoxicity of ex vivo expanded natural killer cells in combination with monoclonal antibody drugs against cancer cells.* Int Immunopharmacol, 2012. 14(4): p. 593-605.
83. Luhm, J., et al., *Large-scale generation of natural killer lymphocytes for clinical application.* J Hematother Stem Cell Res, 2002. 11(4): p. 651-7.
84. Parkhurst, M. R., et al., *Adoptive transfer of autologous natural killer cells leads to high levels of circulating natural killer cells but does not mediate tumor regression.* Clin Cancer Res, 2011. 17(19): p. 6287-97.
85. Harada, H., et al., *Selective expansion of human natural killer cells from peripheral blood mononuclear cells by the cell line, HFWT.* Jpn J Cancer Res, 2002. 93(3): p. 313-9.
86. Voskens, C. J., et al., *Ex-vivo expanded human NK cells express activating receptors that mediate cytotoxicity of allogeneic and autologous cancer cell lines by direct recognition and antibody directed cellular cytotoxicity.* J Exp Clin Cancer Res, 2010. 29: p. 134.
87. Yang, H., et al., *A New Ex Vivo Method for Effective Expansion and Activation of Human Natural Killer Cells for Anti-Tumor Immunotherapy.* Cell Biochem Biophys, 2015. 73(3): p. 723-9.
88. Chang, Y. H., et al., *A chimeric receptor with NKG2D specificity enhances natural killer cell activation and killing of tumor cells.* Cancer Res, 2013. 73(6): p. 1777-86.
89. Fujisaki, H., et al., *Replicative potential of human natural killer cells.* Br J Haematol, 2009. 145(5): p. 606-13.
90. Spanholtz, J., et al., *High log-scale expansion of functional human natural killer cells from umbilical cord blood CD34-positive cells for adoptive cancer immunotherapy.* PLoS One, 2010. 5(2): p. e9221.
91. Spanholtz, J., et al., *Clinical-grade generation of active NK cells from cord blood hematopoietic progenitor cells for immunotherapy using a closed-system culture process.* PLoS One, 2011. 6(6): p. e20740.
92. Tam, Y. K., et al., *Ex vivo expansion of the highly cytotoxic human natural killer-92 cell-line under current good manufacturing practice conditions for clinical adoptive cellular immunotherapy.* Cytotherapy, 2003. 5(3): p. 259-72.
93. Tseng, H.-C., et al., *Induction of Split Anergy Conditions Natural Killer Cells to Promote Differentiation of Stem Cells through Cell-Cell Contact and Secreted Factors.* Frontiers in immunology, 2014. 5: p. 269-269.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the World Wide Web at ncbi.nlm.nih.gov.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A method of treating cancer or a cancer-related disease or disorder in a subject having or suspected of having a cancer or cancer-related disease or disorder, comprising administering to the subject
   (a) a therapeutically effective amount of a composition comprising bacterial strains of: *Streptococcus thermophilus, Bifidobacterium longum, Bifidobacterium breve, Bifidobacterium infantis, Lactobacillus acidophilus, Lactobacillus plantarum*, and *Lactobacillus paracasei*; and
   (b) a therapeutically effective amount of a composition comprising:
      (i) at least one NK cell; and/or
      (ii) at least one non-NK cell that is capable of activating an NK cell.
2. The method of claim 1, wherein the composition further comprises *L. casei* KE99 and/or *Lactobacillus bulgaricus*.
3. The method of claim 1, wherein the composition
   i) induces and/or increases differentiation of the cancer cells in the subject;
   ii) induces and/or increases resistance to NK-cell-mediated cytotoxicity of the cancer cells in the subject;
   iii) decreases or inhibits tumor growth in the subject; and/or
   iv) decreases or inhibits proliferation of a cancer cell in the subject.
4. The method of claim 1, wherein the composition induces and/or increases the production, secretion, and/or function of at least one cytokine or chemokine in the subject, optionally wherein the at least one cytokine and/or chemokine is one of those listed in Table 1.
5. The method of claim 4, wherein the at least one cytokine or chemokine is selected from: IL-6, IL-1Ra, TNF-α, IL-12p70, G-CSF, IL-8, RANTES, Eotaxin, MCP-1, IL-17, IL-10, IL-12, IFN-γ, TGF-α, GM-CSF, IL-13, IL-17A, IL-1β, IL-2, IL-21, IL-4, IL-23, IL-5, IL-7, FRACTALKINE, MIP-3α, MIP-1α, and MIP-1β.
6. The method of claim 1, wherein the composition is administered via systemic administration, oral administration, or rectal administration.
7. The method of claim 1, wherein the cancer is an oral cancer or a pancreatic cancer.
8. The method of claim 1, wherein the subject is a human.
9. The method of claim 1, wherein the method further comprises administering to the subject an anti-PD1 antibody and/or at least one chemotherapeutic agent.
10. The method of claim 9, wherein the at least one chemotherapeutic agent is cisplatin (CDDP), Paclitaxel (PTX), and/or N-acetylcysteine (NAC).
11. The method of claim 1, wherein the at least one non-NK cell is an osteoclast cell.
12. The method of claim 9, wherein the composition
   i) induces and/or increases differentiation of the cancer cells in the subject;
   ii) induces and/or increases resistance to NK-cell-mediated cytotoxicity of the cancer cells in the subject;
   iii) decreases or inhibits tumor growth in the subject; and/or
   iv) decreases or inhibits proliferation of a cancer cell in the subject.
13. The method of claim 9, wherein the composition induces and/or increases the production, secretion, and/or function of at least one cytokine or chemokine in the subject, optionally wherein the at least one cytokine and/or chemokine is one of those listed in Table 1.

14. The method of claim 13, wherein the at least one cytokine or chemokine is selected from: IL-6, IL-1Ra, TNF-α, IL-12p70, G-CSF, IL-8, RANTES, Eotaxin, MCP-1, IL-17, IL-10, IL-12, IFN-γ, TGF-α, GM-CSF, IL-13, IL-17A, IL-1β, IL-2, IL-21, IL-4, IL-23, IL-5, IL-7, FRACTALKINE, MIP-3α, MIP-1α, and MIP-1β.

15. The method of claim 9, wherein the composition is administered via systemic administration, oral administration, or rectal administration.

16. The method of claim 9, wherein the cancer is an oral cancer or a pancreatic cancer.

17. The method of claim 9, wherein the subject is a human.

18. The method of claim 1, wherein the at least one NK cell has been co-cultured with an osteoclast cell prior to the at least one NK cell being administered to the subject.

* * * * *